(12) United States Patent
Yim et al.

(10) Patent No.: US 8,703,814 B1
(45) Date of Patent: Apr. 22, 2014

(54) PHARMACEUTICAL AND FOOD COMPOSITIONS FOR PREVENTING OR TREATING DIABETES OR OBESITY

(71) Applicant: Korea Ocean Research and Development Institute, Incheon (KR)

(72) Inventors: Joung Han Yim, Gyeonggi-do (KR); Il Chan Kim, Gyeonggi-do (KR); Doc Kyu Kim, Incheon (KR); Se Jong Han, Gyunggi-do (KR); Hyoung Seok Lee, Seoul (KR); Bhattarai Hari Datta, Incheon (KR); Jung Eun Kim, Incheon (KR); Tai Kyoung Kim, Incheon (KR); Hyun Cheol Oh, Busan (KR); Dong-Gyu Jo, Gyeonggi-do (KR); Cheolsoon Lee, Incheon (KR); Keun-Sik Kim, Jeollanam-do (KR); Pyung Cheon Lee, Gyeonggi-do (KR); Mi Ra Park, Incheon (KR); Yu-Kyung Park, Incheon (KR); Sung Jin Kim, Incheon (KR); Pil-Sung Kang, Incheon (KR); Heeyong Park, Gyeonggi-do (KR); Ha Ju Park, Gyeonggi-do (KR)

(73) Assignee: Korea Ocean Research and Development Institute, Incheon (KR)

( * ) Notice: Subject to any disclaimer, the term of this patent is extended or adjusted under 35 U.S.C. 154(b) by 0 days.

(21) Appl. No.: 13/900,361

(22) Filed: May 22, 2013

Related U.S. Application Data

(62) Division of application No. 13/878,196, filed as application No. PCT/KR2011/004836 on Jul. 1, 2011.

(30) Foreign Application Priority Data

| Oct. 7, 2010 | (KR) | 10-2010-0097677 |
| Oct. 7, 2010 | (KR) | 10-2010-0097678 |
| Apr. 26, 2011 | (KR) | 10-2011-0039155 |

(51) Int. Cl.
*A61K 31/343* (2006.01)
*C07D 307/88* (2006.01)

(52) U.S. Cl.
USPC .......................................... 514/470; 549/310

(58) Field of Classification Search
USPC .................................. 514/470; 549/268, 310
See application file for complete search history.

(56) References Cited

U.S. PATENT DOCUMENTS

| 2009/0048332 A1 | 2/2009 | Choudhary et al. |
| 2009/0143279 A1 | 6/2009 | Mootha et al. |
| 2013/0261174 A1 | 10/2013 | Yim et al. |

OTHER PUBLICATIONS

Huneck, S., "The Significance of Lichens and Their Metabolites", "Naturwissenschaffen", 1999, pp. 559-570, vol. 86.
Ingolfsdottir, K., "Molecules of Interest: Usnic acid", "Phytochemistry", 2002, pp. 729-736, vol. 61.
Koren, S., et al., "Inhibition of the protein tyrosine phosphatase PTP1B: potential therapy for obesity, insulin resistance and type-2 diabetes mellitus", "Best Practice & Research Clinical Endocrinology & Metabolism", 2007, pp. 621-640, vol. 21, No. 4.
Kumar, S., et al., "Lichen Metabolites. 1. Inhibitory Action Against Leukotriene B4 Biosynthesis by a Non-Redox Mechanism", "J. Nat. Prod.", 1999, pp. 817-820, vol. 62.
Liu, S., et al., "Targeting Inactive Enzyme Conformation: Aryl Diketoacid Derivatives as a New Class of PTP1B Inhibitors", "J. Am. Chem. Soc.", Nov. 14, 2008, pp. 17075-17084, vol. 130.
Seo, C., et al., "Protein tyrosine phosphatase 1B inhibitory effects of depsidone and pseudodepsidone metabolites from the Antarctic lichen Stereocaulon alpinum", "Bioorganic & Medicinal Chemistry Letters", Mar. 26, 2009, pp. 2801-2803, vol. 19.
Dec. 17, 2013 Office Action issued in U.S. Appl. No. 13/878,196 by Kristin Ann Vajda.
Dec. 24, 2013 Notice of Allowance issued in U.S. Appl. No. 13/900,155 by Kristin Ann Vajda.
Unpublished U.S. Appl. No. 13/900,155, filed May 22, 2013.

*Primary Examiner* — Kristin Vajda
(74) *Attorney, Agent, or Firm* — Hultquist, PLLC; Steven J. Hultquist

(57) ABSTRACT

The present invention relates to pharmaceutical and food compositions for preventing or treating diabetes or obesity, and more particularly to pharmaceutical compositions and functional foods for preventing or treating diabetes or obesity, which contain, as an active ingredient, a novel compound synthesized from a compound separated from an extract of the *Stereocaulon alpinum*. The novel compounds of the invention have very excellent PTP-1b (protein tyrosine phosphatase-1b) inhibitory activities, act selectively only on PTP-1b among protein tyrosine phosphatases, and are substantial PTP-1b inhibitors which are effective in preventing or treating diabetes or obesity.

9 Claims, 42 Drawing Sheets

| Filename | = Lobaric_Na_Salt(2)-H- |
|---|---|
| Author | = SU_NMR |
| Experiment | = single_pulse.exp |
| Sample_id | = Lobaric_Na_Salt(2) |
| Solvent | = DMSO-D6 |
| Creation_time | = 5-OCT-2010 11:12:12 |
| Revision_time | = 5-OCT-2010 16:37:48 |
| Current_time | = 5-OCT-2010 16:38:18 |
| Comment | = Single Pulse Experime |
| Data_format | = 1D COMPLEX |
| Dim_size | = 16384 |
| Dim_title | = 1H |
| Dim_units | = [ppm] |
| Dimensions | = X |
| Site | = Eclipse + 400 |
| Spectrometer | = DELTA_NMR |

| Field_strength | = 9.389766[T] (400 [MHz]) |
|---|---|
| X_acq_duration | = 2.7312128[s] |
| X_domain | = 1H |
| X_freq | = 399.78219838[MHz] |
| X_offset | = 5[ppm] |
| X_points | = 16384 |
| X_prescans | = 0 |
| X_resolution | = 0.36613771[Hz] |
| X_sweep | = 5.99880024[kHz] |
| Mod_return | = 1 |
| Scans | = 16 |
| Total_Scans | = 16 |
| X_90_width | = 8.8[us] |
| X_acq_time | = 2.7312128[s] |
| X_angle | = 45[deg] |
| X_pulse | = 4.4[us] |
| Initial_wait | = 1[s] |
| Phase_preset | = 3[us] |
| Recvr_gain | = 14 |
| Relaxation_delay | = 2[s] |
| Temp_get | = 22.7[dC] |
| Unblank_time | = 2[us] |

| Filename | = Lobaric_Na_Salt(2)-C- |
| Author | = SU_NMR |
| Experiment | = single_pulse_dec |
| Sample_id | = Lobaric_Na_Salt(2) |
| Solvent | = DMSO-D6 |
| Creation_time | = 5-OCT-2010 14:37:22 |
| Revision_time | = 5-OCT-2010 16:38:59 |
| Current_time | = 5-OCT-2010 16:39:12 |
| Comment | = Single Pulse with Bro |
| Data_format | = 1D COMPLEX |
| Dim_size | = 32768 |
| Dim_title | = 13C |
| Dim_units | = [ppm] |
| Dimensions | = X |
| Site | = Eclipse + 400 |
| Spectrometer | = DELTA_NMR |

| Field_strength | = 9.389766[T] (400 [MHz] |
| X_acq_duration | = 1.3008896[s] |
| X_domain | = 13C |
| X_freq | = 100.52530333[MHz] |
| X_offset | = 100[ppm] |
| X_points | = 32768 |
| X_prescans | = 4 |
| X_resolution | = 0.76870474[Hz] |
| X_sweep | = 25.18891688[kHz] |
| Irr_domain | = 1H |
| Irr_freq | = 399.78219838[MHz] |
| Irr_offset | = 5[ppm] |
| Mod_return | = 1 |
| Scans | = 3204 |
| Total_Scans | = 3204 |
| X_90_width | = 9.8[us] |
| X_acq_time | = 1.3008896[s] |
| X_angle | = 30[deg] |
| X_pulse | = 3.26666667[us] |
| Initial_wait | = 1[s] |
| Phase_preset | = 3[us] |
| Recvr_gain | = 28 |
| Relaxation_delay | = 1[s] |
| Temp_get | = 24.8[dC] |
| Unblank_time | = 2[us] |

FIG.3B

| FIG.3A | FIG.3B | FIG.3

| Filename | = Lobaric_No_Salt(2)-QC | Field_strength | = 9.389766[T] (400 [MHz]) | X_acq_time | = 0.303616[s] |
|---|---|---|---|---|---|
| Author | = SU_NMR | X_acq_duration | = 0.303616[s] | X_pulse | = 5.8[us] |
| Experiment | = hsqc_pfg_m_phase | X_domain | = 1H | Y_acq_time | = 12.032[ms] |
| Sample_id | = Lobaric_No_Salt(2) | X_freq | = 399.78219838[MHz] | Y_pulse | = 19[us] |
| Solvent | = DMSO-D6 | X_offset | = 4.23669[ppm] | Delay1 | = 1.2136[ms] |
| Creation_time | = 5-OCT-2010 15:35:26 | X_points | = 1024 | Grad_1 | = 1[ms] |
| Revision_time | = 5-OCT-2010 16:04:24 | X_prescans | = 4 | Grad_1_amp | = 40[%] |
| Current_time | = 5-OCT-2010 16:40:07 | X_resolution | = 3.29363406[Hz] | Grad_2 | = 1[ms] |
|  |  | X_sweep | = 3.37268128[kHz] | Grad_2_amp | = 10[%] |
| Comment | = HSQC 2d with X-decoup | Y_domain | = 13c | Grad_3 | = 1[ms] |
| Data_format | = 2D COMPLEX COMPLEX | Y_freq | = 100.52530333[MHz] | Grad_3_amp | = −10[%] |
| Dim_size | = 1024, 512 | Y_offset | = 105.81513[ppm] | Grad_recover | = 0.2[ms] |
| Dim_title | = 1H 13C | Y_points | = 256 | Grad_selection | = 13c = 4:1 |
| Dim_units | = [ppm] [ppm] | Y_prescans | = 0 | Grad_shape | = square |
| Dimensions | = X Y | Y_resolution | = 83.11170213[Hz] | Grad_type | = 0 |
| Site | = Eclipse + 400 | Y_sweep | = 21.27659574[kHz] | Initial_wait | = 0.1[s] |
| Spectrometer | = DELTA_NMR | Mod_return | = 1 | J_constant | = 140[Hz] |
|  |  | Scans | = 2 | Phase_preset | = 3[us] |
|  |  | Total_Scans | = 512 | Purge | = 2[ms] |
|  |  |  |  | Recvr_gain | = 30 |
|  |  |  |  | Refocus_comp | = 0.78571429[ms] |
|  |  |  |  | Relaxation_delay | = 2[s] |
|  |  |  |  | T1 | = 1[us] |
|  |  |  |  | Temp_get | = 24.1[dC] |
|  |  |  |  | Unblank_time | = 2[us] |

FIG.4B

| FIG.4A | FIG.4B |
|---|---|

FIG.4

| | | | | |
|---|---|---|---|---|
| Filename | = Lobaric_Na_Salt(2)-BC | Field_strength | = 9.39766[T] (400 [MHz] | X_acq_time | = 0.303616[s] |
| Author | = SU_NMR | X_acq_duration | = 0.303616[s] | X_pulse | = 5.8[us] |
| Experiment | = hmbc_pfg_m.exp | X_domain | = 1H | Y_acq_time | = 12.032[ms] |
| Sample_id | = Lobaric_Na_Salt(2) | X_freq | = 399.78219838[MHz] | Y_pulse | = 19[us] |
| Solvent | = DMSO-D6 | X_offset | = 4.23669[ppm] | Grad_1 | = 1[ms] |
| Creation_time | = 5-OCT-2010 16:42:20 | X_points | = 1024 | Grad_1_amp | = 60[%] |
| Revision_time | = 5-OCT-2010 16:58:19 | X_prescans | = 4 | Grad_2 | = 1[ms] |
| Current_time | = 5-OCT-2010 18:42:32 | X_resolution | = 3.29363406[Hz] | Grad_2_amp | = 60[%] |
| | | X_sweep | = 3.37268128[kHz] | Grad_3 | = 1[ms] |
| Comment | = gradient enhanced HMB | Y_domain | = 13c | Grad_3_amp | = 30[%] |
| Data_format | = 2D REAL REAL | Y_freq | = 100.52530333[MHz] | Grad_recover | = 1[ms] |
| Dim_size | = 1024, 1024 | Y_offset | = 105.81513[ppm] | Grad_selection | = 13c = 2:2:1 |
| Dim_title | = 1H 13C | Y_points | = 256 | Grad_shape | = square |
| Dim_units | = [ppm] [ppm] | Y_prescans | = 0 | Grad_type | = 0 |
| Dimensions | = X Y | Y_resolution | = 83.11170213[Hz] | Initial_wait | = 1[s] |
| Site | = Eclipse + 400 | Y_sweep | = 21.27659574[kHz] | J_constant | = 140[Hz] |
| Spectrometer | = DELTA_NMR | Mod_return | = 1 | Long_range_j | = 8[Hz] |
| | | Scans | = 4 | Phase_preset | = 3[us] |
| | | Total_Scans | = 1024 | Recvr_gain | = 30 |
| | | | | Relaxation_delay | = 2[s] |
| | | | | T1 | = 1[us] |
| | | | | Temp_get | = 22.7[dC] |
| | | | | Unblank_time | = 2[us] |

| FIG.5A | FIG.5B |
|---|---|

FIG.5

| Filename | = Lobaric_1N_NaOH-MC-2- | X_90_width | = 8.9[us] |
| Experiment | = single_pulse.exp | X_acq_time | = 2.7312128[s] |
| Sample_id | = Lobaric_1N NaOH-MC-2 | X_angle | = 45[deg] |
| Solvent | = DMSO-D6 | X_pulse | = 4.45[us] |
| Creation_time | = 11-JUN-2010 18:34:19 | Initial_wait | = 1[s] |
| Revision_time | = 1-OCT-2010 17:39:52 | Phase_preset | = 3[us] |
| Current_time | = 1-OCT-2010 18:18:39 | Recvr_gain | = 16 |
| | | Relaxation_delay | = 4[s] |
| Comment | = Single Pulse Experime | Temp_get | = 21.8[dC] |
| Data_format | = 1D COMPLEX | | |
| Dim_size | = 16384 | | |
| Dim_title | = 1H | | |
| Dim_units | = [ppm] | | |
| Dimensions | = X | | |
| Site | = ECP400 | | |
| Spectrometer | = DELTA_NMR | | |
| Field_strength | = 9.389766[T] (400 [MHz]) | | |
| X_acq_duration | = 2.7312128[s] | | |
| X_domain | = 1H | | |
| X_freq | = 399.78219838[MHz] | | |
| X_offset | = 5[ppm] | | |
| X_points | = 16384 | | |
| X_prescans | = 0 | | |
| X_resolution | = 0.36613771[Hz] | | |
| X_sweep | = 5.99880024[kHz] | | |
| Mod_return | = 1 | | |
| Scans | = 32 | | |

FIG.13B
FIG.13

| FIG.13A | FIG.13B |

| | |
|---|---|
| Filename | = Lobaric_1N_NaOH-MC-2- |
| Experiment | = single_pulse_dec |
| Sample_id | = Lobaric_1N NaOH-MC-2- |
| Solvent | = DMSO-D6 |
| Creation_time | = 12-JUN-2010 07:27:58 |
| Revision_time | = 1-OCT-2010 17:19:58 |
| Current_time | = 1-OCT-2010 18:18:55 |
| Comment | = Single Pulse with Bro |
| Data_format | = 1D COMPLEX |
| Dim_size | = 32768 |
| Dim_title | = 13C |
| Dim_units | = [ppm] |
| Dimensions | = X |
| Site | = ECP400 |
| Spectrometer | = DELTA_NMR |
| Field_strength | = 9.389766[T] (400 [MHz] |
| X_acq_duration | = 1.3008896[s] |
| X_domain | = 13C |
| X_freq | = 100.52530333[MHz] |
| X_offset | = 100[ppm] |
| X_points | = 32768 |
| X_prescans | = 4 |
| X_resolution | = 0.76870474[Hz] |
| X_sweep | = 25.1891688[kHz] |
| Irr_domain | = 1H |
| Irr_freq | = 399.78219838[MHz] |
| Irr_offset | = 5[ppm] |
| Mod_return | = 1 |
| Scans | = 20095 |
| X_90_width | = 9.4[us] |
| X_acq_time | = 1.3008896[s] |
| X_angle | = 30[deg] |
| X_pulse | = 3.13333333[us] |
| Initial_wait | = 1[s] |
| Phase_preset | = 3[us] |
| Recvr_gain | = 24 |
| Relaxation_delay | = 1[s] |
| Temp_get | = 23.1[dC] |

| | | | | |
|---|---|---|---|---|
| Filename | = Lobaric_1N NaOH-MC-2- | Field_strength | = 9.389766[T] (400 [MHz]) | X_acq_time | = 0.2409472[s] |
| Author | = Administrator | X_acq_duration | = 0.2409472[s] | X_pulse | = 5.8[us] |
| Experiment | = hsqc_pfg_m_phase | X_domain | = 1H | Y_acq_time | = 13.4144[ms] |
| Sample_id | = Lobaric_1N NaOH-MC-2 | X_freq | = 399.78219838[MHz] | Y_pulse | = 19[us] |
| Solvent | = DMSO-D6 | X_offset | = 5.29874[ppm] | Delay1 | = 1.2136[ms] |
| Creation_time | = 19-JUN-2010 23:04:03 | X_points | = 1024 | Grad_1 | = 1[ms] |
| Revision_time | = 1-OCT-2010 17:23:30 | X_prescans | = 4 | Grad_1_amp | = 40[%] |
| Current_time | = 1-OCT-2010 18:19:16 | X_resolution | = 4.15028687[Hz] | Grad_2 | = 1[ms] |
| | | X_sweep | = 4.24989375[kHz] | Grad_2_amp | = 10[%] |
| Comment | = HSQC 2d with X-decoup | Y_domain | = 13c | Grad_3 | = 1[ms] |
| Data_format | = 2D COMPLEX COMPLEX | Y_freq | = 100.52530333[MHz] | Grad_3_amp | = -10[%] |
| Dim_size | = 1024, 512 | Y_offset | = 98.20031[ppm] | Grad_recover | = 0.2[ms] |
| Dim_title | = 1H 13C | Y_points | = 256 | Grad_selection | = 13c = 4:1 |
| Dim_units | = [ppm] [ppm] | Y_prescans | = 0 | Grad_shape | = square |
| Dimensions | = X Y | Y_resolution | = 74.54675573[Hz] | Grad_type | = 0 |
| Site | = Eclipse + 400 | Y_sweep | = 19.08396947[kHz] | Initial_wait | = 0.1[s] |
| Spectrometer | = DELTA_NMR | Mod_return | = 1 | J_constant | = 140[Hz] |
| | | Scans | = 64 | Phase_preset | = 3[us] |
| | | Total_Scans | = 16384 | Purge | = 2[ms] |
| | | | | Recvr_gain | = 30 |
| | | | | Refocus_comp | = 0.78571429[ms] |
| | | | | Relaxation_delay | = 2[s] |
| | | | | T1 | = 1[us] |
| | | | | Temp_get | = 24.8[dC] |
| | | | | Unblank_time | = 2[us] |

FIG. 15B

| FIG.15A | FIG.15B |
|---|---|

FIG. 15

| | | | |
|---|---|---|---|
| Filename | = Lobaric_1N_NaOH-MC-2- | Field_strength | = 9.389766[T] (400 [MHz] |
| Experiment | = hmbc_pfg_m.exp | X_acq_duration | = 0.2167808[s] |
| Sample_id | = Lobaric_1N NaOH-MC-2 | X_domain | = 1H |
| Solvent | = DMSO-D6 | X_freq | = 399.78219838[MHz] |
| Creation_time | = 13-JUN-2010 07:39:10 | X_offset | = 5.85382[ppm] |
| Revision_time | = 1-OCT-2010 17:26:17 | X_points | = 1024 |
| Current_time | = 1-OCT-2010 18:19:34 | X_prescans | = 4 |
| | | X_resolution | = 4.61295465[Hz] |
| Comment | = _hmbc | X_sweep | = 4.72366556[kHz] |
| Data_format | = 2D REAL REAL | Y_domain | = 13c |
| Dim_size | = 1024, 1024 | Y_freq | = 100.52530333[MHz] |
| Dim_title | = 1H 13C | Y_offset | = 112.9641[ppm] |
| Dim_units | = [ppm] [ppm] | Y_points | = 256 |
| Dimensions | = X Y | Y_prescans | = 0 |
| Site | = ECP400 | Y_resolution | = 88.37769683[Hz] |
| Spectrometer | = DELTA_NMR | Y_sweep | = 22.62443439[kHz] |
| | | Mod_return | = 1 |
| | | Scans | = 102 |

| | |
|---|---|
| X_acq_time | = 0.2167808[s] |
| X_pulse | = 5.7[us] |
| Y_acq_time | = 11.3152[ms] |
| Y_pulse | = 23.5[us] |
| Grad_1 | = 1[ms] |
| Grad_1_amp | = 60[%] |
| Grad_2 | = 1[ms] |
| Grad_2_amp | = 60[%] |
| Grad_3 | = 1[ms] |
| Grad_3_amp | = 30.4[%] |
| Grad_recover | = 1[ms] |
| Grad_selection | = |
| Grad_shape | = |
| Grad_type | = 2 |
| Initial_wait | = 1[s] |
| J_constant | = 140[Hz] |
| Long_range_j | = 8[Hz] |
| Phase_preset | = 3[us] |
| Recvr_gain | = 30 |
| Relaxation_delay | = 2[s] |
| T1 | = 1[us] |
| Temp_get | = 21.7[dC] |

| FIG.16A | FIG.16B |
|---|---|

| | | | |
|---|---|---|---|
| Filename | = M11-A-H-5.jdf | Field_strength | = 9.389766[T] (400 [MHz]) |
| Author | = SU_NMR | X_acq_duration | = 2.7312128[s] |
| Experiment | = single_pulse.exp | X_domain | = 1H |
| Sample_id | = M-11A | X_freq | = 399.78219838[MHz] |
| Solvent | = DMSO-D6 | X_offset | = 5[ppm] |
| Creation_time | = 15-OCT-2010 19:25:33 | X_points | = 16384 |
| Revision_time | = 25-FEB-2011 15:24:31 | X_prescans | = 0 |
| Current_time | = 25-FEB-2011 15:24:58 | X_resolution | = 0.36613771[Hz] |
| | | X_sweep | = 5.99880024[kHz] |
| Comment | = Single Pulse Experime | Mod_return | = 1 |
| Data_format | = 1D COMPLEX | Scans | = 32 |
| Dim_size | = 16384 | Total_Scans | = 32 |
| Dim_title | = 1H | | |
| Dim_units | = [ppm] | X_90_width | = 5.8[us] |
| Dimensions | = X | X_acq_time | = 2.7312128[s] |
| Site | = Eclipse + 400 | X_angle | = 45[deg] |
| Spectrometer | = DELTA_NMR | X_pulse | = 2.9[us] |
| | | Initial_wait | = 1[s] |
| | | Phase_preset | = 3[us] |
| | | Recvr_gain | = 18 |
| | | Relaxation_delay | = 2[s] |
| | | Temp_get | = 22.4[dC] |
| | | Unblank_time | = 2[us] |

| FIG.24A | FIG.24B | FIG.24 |

| | | |
|---|---|---|
| Filename | = | M-11-A-C-4.jdf |
| Author | = | SU_NMR |
| Experiment | = | single_pulse_dec |
| Sample_id | = | M-11-A |
| Solvent | = | DMSO-D6 |
| Creation_time | = | 18-OCT-2010 10:19:05 |
| Revision_time | = | 25-FEB-2011 15:26:06 |
| Current_time | = | 25-FEB-2011 15:26:22 |
| Comment | = | Single Pulse with Bro |
| Data_format | = | 1D COMPLEX |
| Dim_size | = | 32768 |
| Dim_title | = | 13C |
| Dim_units | = | [ppm] |
| Dimensions | = | X |
| Site | = | Eclipse + 400 |
| Spectrometer | = | DELTA_NMR |

| | | |
|---|---|---|
| Field_strength | = | 9.389766[T] (400 [MHz] |
| X_acq_duration | = | 1.3008896[s] |
| X_domain | = | 13C |
| X_freq | = | 100.52530333[MHz] |
| X_offset | = | 100[ppm] |
| X_points | = | 32768 |
| X_prescans | = | 4 |
| X_resolution | = | 0.76870474[Hz] |
| X_sweep | = | 25.1891688[kHz] |
| Irr_domain | = | 1H |
| Irr_freq | = | 399.78219838[MHz] |
| Irr_offset | = | 5[ppm] |
| Mod_return | = | 1 |
| Scans | = | 19387 |
| Total_Scans | = | 19387 |
| X_90_width | = | 9.8[us] |
| X_acq_time | = | 1.3008896[s] |
| X_angle | = | 30[deg] |
| X_pulse | = | 3.26666667[us] |
| Initial_wait | = | 1[s] |
| Phase_preset | = | 3[us] |
| Recvr_gain | = | 28 |
| Relaxation_delay | = | 1[s] |
| Temp_get | = | 24.9[dC] |
| Unblank_time | = | 2[us] |

| FIG.25A | FIG.25B |

| | | |
|---|---|---|
| Filename | = | M11-A-COSY-2.jdf |
| Author | = | SU_NMR |
| Experiment | = | cosy_pfg_m.exp |
| Sample_id | = | M-11-A |
| Solvent | = | DMSO-D6 |
| Creation_time | = | 16-OCT-2010 12:35:18 |
| Revision_time | = | 26-FEB-2011 09:34:26 |
| Current_time | = | 26-FEB-2011 09:36:01 |
| Comment | = | gradient absolute val |
| Data_format | = | 2D REAL REAL |
| Dim_size | = | 1024, 1024 |
| Dim_title | = | 1H 1H |
| Dim_units | = | [ppm] [ppm] |
| Dimensions | = | X Y |
| Site | = | Eclipse + 400 |
| Spectrometer | = | DELTA_NMR |

| | | |
|---|---|---|
| Field_strength | = | 9.389766[T] (400 [MHz] |
| X_acq_duration | = | 0.219648[s] |
| X_domain | = | 1H |
| X_freq | = | 399.78219838[MHz] |
| X_offset | = | 5.60605[ppm] |
| X_points | = | 1024 |
| X_prescans | = | 4 |
| X_resolution | = | 4.55273893[Hz] |
| X_sweep | = | 4.66200466[kHz] |
| Y_domain | = | 1H |
| Y_freq | = | 399.78219838[MHz] |
| Y_offset | = | 5.60605[ppm] |
| Y_points | = | 256 |
| Y_prescans | = | 0 |
| Y_resolution | = | 18.21095571[Hz] |
| Y_sweep | = | 4.66200466[kHz] |
| Mod_return | = | 1 |
| Scans | = | 16 |
| Total_Scans | = | 4096 |

| | | |
|---|---|---|
| X_90_width | = | 5.8[us] |
| X_acq_time | = | 0.219648[s] |
| X_pulse | = | 5.8[us] |
| Y_acq_time | = | 54.912[ms] |
| Grad_1 | = | 1[ms] |
| Grad_1_amp | = | 50[%] |
| Grad_2 | = | 1[ms] |
| Grad_2_amp | = | 50[%] |
| Grad_recover | = | 1[ms] |
| Grad_selection | = | 1:1 |
| Grad_shape | = | square |
| Grad_type | = | 0 |
| Initial_wait | = | 0.1[s] |
| Phase_preset | = | 3[us] |
| Pulse_1 | = | 5.8[us] |
| Pulse_2 | = | 5.8[us] |
| Pulse_angle_1 | = | 90[deg] |
| Pulse_angle_2 | = | 90[deg] |
| Recvr_gain | = | 18 |
| Relaxation_delay | = | 1[s] |
| T1 | = | 1[us] |
| Temp_get | = | 22.3[dC] |
| Unblank_time | = | 2[us] |

| FIG.26A | FIG.26B |
|---|---|

FIG.26

| | |
|---|---|
| Filename | = M-11-A-QC-2.jdf |
| Author | = SU_NMR |
| Experiment | = hsqc_pfg_m_phase |
| Sample_id | = M-11-A |
| Solvent | = DMSO-D6 |
| Creation_time | = 16-OCT-2010 11:09:40 |
| Revision_time | = 25-FEB-2011 15:26:54 |
| Current_time | = 25-FEB-2011 15:28:22 |
| Comment | = HSQC 2d with X-decoup |
| Data_format | = 2D COMPLEX COMPLEX |
| Dim_size | = 1024, 512 |
| Dim_title | = 1H 13C |
| Dim_units | = [ppm] [ppm] |
| Dimensions | = X Y |
| Site | = Eclipse + 400 |
| Spectrometer | = DELTA_NMR |
| Field_strength | = 9.389766[T] (400 [MHz]) |
| X_acq_duration | = 0.219648[s] |
| X_domain | = 1H |
| X_freq | = 399.78219838[MHz] |
| X_offset | = 5.60605[ppm] |
| X_points | = 1024 |
| X_prescans | = 4 |
| X_resolution | = 4.55273893[Hz] |
| X_sweep | = 4.66200466[kHz] |
| Y_domain | = 13c |
| Y_freq | = 100.52530333[MHz] |
| Y_offset | = 100[ppm] |
| Y_points | = 256 |
| Y_prescans | = 0 |
| Y_resolution | = 98.64267677[Hz] |
| Y_sweep | = 25.25252525[kHz] |
| Mod_return | = 1 |
| Scans | = 48 |
| Total_Scans | = 12288.0 |
| X_acq_time | = 0.219648[s] |
| X_pulse | = 5.8[us] |
| Y_acq_time | = 10.1376[ms] |
| Y_pulse | = 19[us] |
| Delay1 | = 1.2136[ms] |
| Grad_1 | = 1[ms] |
| Grad_1_amp | = 40[%] |
| Grad_2 | = 1[ms] |
| Grad_2_amp | = 10[%] |
| Grad_3 | = 1[ms] |
| Grad_3_amp | = -10[%] |
| Grad_recover | = 0.2[ms] |
| Grad_selection | = 13c = 4:1 |
| Grad_shape | = square |
| Grad_type | = 0 |
| Initial_wait | = 0.1[s] |
| J_constant | = 140[Hz] |
| Phase_preset | = 3[us] |
| Purge | = 2[ms] |
| Recvr_gain | = 30 |
| Refocus_comp | = 0.78571429[ms] |
| Relaxation_delay | = 2[s] |
| T1 | = 1[us] |
| Temp_get | = 23.5[dC] |
| Unblank_time | = 2[us] |

| Filename | = Lobaric_1N_NaOH-MC-2- | Field_strength | = 9.389766[T] (400 [MHz] | X_acq_time | = 0.2167808[s] |
| Experiment | = hmbc_pfg_m.exp | X_acq_duration | = 0.2167808[s] | X_pulse | = 5.7[us] |
| Sample_id | = Lobaric_1N NaOH-MC-2 | X_domain | = 1H | Y_acq_time | = 11.3152[ms] |
| Solvent | = DMSO-D6 | X_freq | = 399.78219838[MHz] | Y_pulse | = 23.5[us] |
| Creation_time | = 13-JUN-2010 07:39:10 | X_offset | = 5.85382[ppm] | Grad_1 | = 1[ms] |
| Revision_time | = 1-OCT-2010 17:26:17 | X_points | = 1024 | Grad_1_amp | = 60[%] |
| Current_time | = 1-OCT-2010 18:19:34 | X_prescans | = 4 | Grad_2 | = 1[ms] |
| | | X_resolution | = 4.61295465[Hz] | Grad_2_amp | = 60[%] |
| Comment | = _hmbc | X_sweep | = 4.72366556[kHz] | Grad_3 | = 1[ms] |
| Data_format | = 2D REAL REAL | Y_domain | = 13c | Grad_3_amp | = 30.4[%] |
| Dim_size | = 1024, 1024 | Y_freq | = 100.52530333[MHz] | Grad_recover | = 1[ms] |
| Dim_title | = 1H 13C | Y_offset | = 112.9641[ppm] | Grad_selection | |
| Dim_units | = [ppm] [ppm] | Y_points | = 256 | Grad_shape | |
| Dimensions | = X Y | Y_prescans | = 0 | Grad_type | = 2 |
| Site | = ECP400 | Y_resolution | = 88.37669683[Hz] | Initial_wait | = 1[s] |
| Spectrometer | = DELTA_NMR | Y_sweep | = 22.62443439[kHz] | J_constant | = 140[Hz] |
| | | Mod_return | = 1 | Long_range_j | = 8[Hz] |
| | | Scans | = 102 | Phase_preset | = 3[us] |
| | | | | Recvr_gain | = 30 |
| | | | | Relaxation_delay | = 2[s] |
| | | | | T1 | = 1[us] |
| | | | | Temp_get | = 21.7[dC] |

| FIG.28A | FIG.28B |

| | | | |
|---|---|---|---|
| Filename | = M-11A-NOESY-2.jdf | Field_strength | = 9.389766[T] (400 [MHz]) |
| Author | = SU_NMR | X_acq_duration | = 0.1707008[s] |
| Experiment | = noesy_ps_pfg_m.e | X_domain | = 1H |
| Sample_id | = M-11A | X_freq | = 399.78219838[MHz] |
| Solvent | = DMSO-D6 | X_offset | = 5[ppm] |
| Creation_time | = 11-FEB-2011 21:57:02 | X_points | = 1024 |
| Revision_time | = 25-FEB-2011 15:32:19 | X_prescans | = 4 |
| Current_time | = 25-FEB-2011 15:32:29 | X_resolution | = 5.85820336[Hz] |
| | | X_sweep | = 5.99880024[kHz] |
| Comment | = gradient phase sensit | Y_domain | = 1H |
| Data_format | = 2D REAL REAL | Y_freq | = 399.78219838[MHz] |
| Dim_size | = 1024, 1024 | Y_offset | = 5[ppm] |
| Dim_title | = 1H 1H | Y_points | = 256 |
| Dim_units | = [ppm] [ppm] | Y_prescans | = 0 |
| Dimensions | = X Y | Y_resolution | = 23.43281344[Hz] |
| Site | = Eclipse + 400 | Y_sweep | = 5.99880024[kHz] |
| Spectrometer | = DELTA_NMR | Mod_return | = 1 |
| | | Scans | = 72 |
| | | Total_Scans | = 18432 |

| | |
|---|---|
| X_acq_time | = 0.1707008[s] |
| X_pulse | = 6[us] |
| Y_acq_time | = 42.6752[ms] |
| Grad_1 | = 2[ms] |
| Grad_1_amp | = 50[%] |
| Grad_recover | = 0.1[ms] |
| Grad_selection | = 1(1) |
| Grad_shape | = square |
| Grad_type | = 0 |
| Initial_wait | = 1[s] |
| Mix_time | = 0.5[s] |
| Phase_preset | = 3[us] |
| Recvr_gain | = 18 |
| Relaxation_delay | = 2[s] |
| T1 | = 10[us] |
| Temp_get | = 23.3[dC] |
| Unblank_time | = 2[us] |

PHARMACEUTICAL AND FOOD COMPOSITIONS FOR PREVENTING OR TREATING DIABETES OR OBESITY

CROSS-REFERENCE TO RELATED APPLICATIONS

This application is a divisional of U.S. patent application Ser. No. 13/878,196 filed on Apr. 5, 2013, which claims priority under the provisions of 35 U.S.C. §371 of International Patent Application No. PCT/KR2011/004836 filed Jul. 1, 2011 and published on Apr. 12, 2012 as International Patent Application Publication No. WO2012/046945, which in turn claims priority of Korean Patent Application No. 10-2010-0097677 filed Oct. 7, 2010, Korean Patent Application No. 10-2010-0097678 filed Oct. 7, 2010, and Korean Patent Application No. 10-2011-0039155 filed Apr. 26, 2011. The disclosures of all of the foregoing applications are hereby incorporated herein by reference in their respective entireties, for all purposes.

TECHNICAL FIELD

The present invention relates to pharmaceutical and food compositions for preventing or treating diabetes or obesity, and more particularly to pharmaceutical compositions and functional foods for preventing or treating diabetes or obesity, which contain, as an active ingredient, a novel compound synthesized from a compound separated from an extract of the Antarctic lichens *Stereocaulon alpinum*.

BACKGROUND ART

Antarctic lichens are known to produce unique secondary metabolites different from those produced by higher plants (Ingolfsdottir, K., *Phytochemistry*, 61:729, 2002). The secondary metabolites produced by these lichens mostly belong to the chemical classes of depsides, depsidones, and dibenzofurans, and these compounds are supposed to be associated with the low growth rate of lichens (Kumar, K. C. S. et al., *J. Nat. Prod.*, 62:817, 1999; Huneck, S., *Naturwissenschaften*, 86:559, 1999). In addition, the various biological activities of lichens, including antibiotic, antimycobacterial, antiviral, pain-killing, and antipyretic activities, and so on were found in screening processes (Ingolfsdottir, K., *Phytochemistry*, 61:729, 2002; Kumar, K. C. S. et al., *J. Nat. Prod.*, 62:817, 1999). Thus, Interest has grown in the development of medical drugs using lichen metabolites.

Meanwhile, diabetes is metabolic disorder symptom, including hyperglycemia, which results from defects in insulin action, insulin secretion, or both. Also, diabetes is more likely to cause vascular complications in the future and can be mostly divided into type 1 diabetes and type 2 diabetes. The type 1 (insulin-dependent) diabetes is caused by immune-mediated destruction of beta cells in the pancreas and the absolute deficiency of insulin accordingly, and the type 2 (non-insulin-dependent) diabetes is developed when the body produces insulin but not enough or cannot use it properly. In the state of insulin resistance in which the body's cells do not respond to insulin properly, the utilization of energy sources, particularly sugars, in the body, is insufficient so that energy required for the body is deficient, and excess sugars accumulate in blood and are released with urine. Thus, diabetes is one of chronic degenerative diseases that are difficult to be cured by the roots.

The World Health Organization (WHO) and the United Nations (UN) emphasize that the number of diabetic patients in the world would reach about 246 millions at the end of the year 2007, and that the prevention of the onset of diabetes, strict regulation of blood glucose levels, and prevention of complications resulting from diabetes are important as the number of deaths caused by diabetes increases gradually year by year. In addition, the Korean Diabetes Association and the Korean Health Insurance Review Assessment Service reported that the total number of diabetic patients in 2003 in Korea was 4.01 millions and that the number of diabetic patients in Korea will reach 7.2 millions in 2030, which correspond to one out of every seven people of the Korean population. Especially, a rapid increase in medical expenses has a close connection with an explosive increase in the number of diabetic patients as well as a continuous increase in diabetic complications and an increase in the life expectancy of diabetic patients. Chronic degenerative diseases such as diabetes are increasing whereas the life expectancy of people is being extended due to the change in eating habits resulting from rapid economic development.

In Korea, type 2 diabetes cases account for more than 99% of total diabetes cases, and type 1 diabetes cases account for less than about 1, which are different from those in foreign counties in which type 2 diabetes cases account for about 90% and type 1 diabetes cases account for about 10%. Diabetes is caused by a variety of factors, including heredopathia (family disease history accounts for about 20% of the cases) and circumstance, ages (40-49 years old occupy about 60%), obesity, reduced immunity, drug abuse, and stress. Although the mechanism of onset of diabetes has not been clearly found, it is known that diabetes is caused by multiple genetic factors, except for several types of diabetes (e.g., MODY), and there is a limit to find genes which are consistently involved in diabetes. In other words, the onset of diabetes is associated with various genes, and many new genes involved in the onset of diabetes are currently being found.

Because diabetes is caused by various mechanisms, various methods are used to treat diabetes. In addition, conventional methods for treating diabetes do not exhibit satisfactory effects in many cases, and thus a new method for treating diabetes is required. Studies on diabetes therapeutic agents have been made mainly to develop agents for treating type 2 diabetes accounting for more than 90% of diabetes cases (see Tables 1 and 2).

TABLE 1

Status of development of diabetes-associated drugs in Korea

| Name of company | Subject of Development | Phase | Remarks |
|---|---|---|---|
| Samjin Pharm Co., Ltd. | Development of diabetes therapeutic agent from natural substances | Preclinical | New drug development |
| | Differentiation of embryonic stem cells into pancreatic beta-cells | Investigation | New drug development |
| SK Co., Ltd. | Diabetes | Application | New drug development |
| Yuyu Pharm Co., Ltd. | YYGG | Investigation | New drug development |
| Yuhan Pharm Co., Ltd. | Biochip | Application | Improvement, diagnosis |
| Chong Kun Dang Pharmaceutical Co., Ltd. | Genetic recombinant human insulin | Phase III | Improved new drug |
| | Neomary tablet | Marketed | Improved new drug |

TABLE 1-continued

Status of development of diabetes-associated drugs in Korea

| Name of company | Subject of Development | Phase | Remarks |
|---|---|---|---|
| Hanmi Pharm Co. Ltd. | HM80200 | Development | Pharmaceutical ingredient |

Excerpt: 2004-Pharmaceutical Industry White Paper, Korea Health Industry Development Institute, Dec, 2004

There have been many studies on insulin secretion stimulators (pirogliride, linogliride, 2,4-diamino-5-cyano-dibromopyridine, incretin, repaglinide, nateglinide), insulin action enhancers (troglitazone), insulin resistance improvers, drugs exhibiting insulin-like effects in target tissue (pirogliride, linogliride, dichloroacetate, insulin lispro, insulin aspart), luconeogenesis inhibitors (lipase inhibitors, carnitine transferase inhibitors, beta-oxidation inhibitors), agents delaying carbohydrate absorption (dietary fiber, alpha-glucosidase inhibitors), and amylin analogues (pramlintide).

Some of these substances are currently being marketed, but a significant number of these substances are in experimental stages or toxicity test stages. Particularly, it is expected that fast-acting insulin secretion stimulators and insulin resistance improvers, developed in view of biorhythm, will be one of the effective treatment methods of diabetes and that the development of these drugs will be active in the future.

In addition, studies on the causes of diabetes have been conducted for past ten years under the presumption that insulin resistance results from defects in insulin receptors. Currently, studies are being directed toward insulin signaling systems.

TABLE 2

Status of development of new drugs for treating diabetes

| Mechanisms of Action | Clinical Phases | | | | | Leading companies |
|---|---|---|---|---|---|---|
| | L | III | II | I | P | |
| α-Glucosidase inhibitor | 3 | | | | 1 | Bayer, Takeda, Chong Kun Dang |
| Insulin agonist | 13 | 5 | 11 | 4 | 27 | Chiron, Eli Lilly, IDEA Zymo-Genetics, Aventis, Novo Nordisk, Akzo Nobel, Biobras, Alkermes, Merk KGaA |
| Glucagon like peptide-1 agonist | | 1 | 4 | 1 | 4 | Amylin, Eli Lilly, Novo Nordisk, Restoragen, Zealand Pharmaceuticals |
| β3-Adrenoreceptor agonist | | | 1 | 2 | 1 | Dainippon, Asahi Kasei, GlaxoSmithKline |
| Dipeptidyl peptide IV inhibitor | | | 2 | | 1 | Bristol-Myers Squibb, Novatis |
| Peroxisome proliferator activated receptor α agonist | | 2 | 2 | | 6 | Novatis, Kyorin, BMS, GlaxoSmithKline |
| Protein tyrosine phosphatase-1B inhibitor | | | 1 | | 7 | Wyeth, ISIS Pharmaceutical |
| Leptin stimulator | | | 1 | | 1 | Amgen, Tularik |
| Melanocortin-4 agonist | | | | | 1 | Neurocrine Biosciences |
| AMPK stimulant | 2 | 2 | 1 | | 1 | Andrx, Merck KGaA, Flamel Technologies |
| Peroxisome proliferator activated receptor γ agonist | 3 | | 4 | | 9 | GlaxoSmithKline, Samchundang, BMS, Japan Tabacco, Dr Reddy's Kyorin |

Excerpt:
Trends in Health Industry & Technology, "Recent Trends in Studies on Diabetes Therapeutic Agents", 2003

It was reported that, when the activities of PTP-1b (protein tyrosine phosphatase-1b) in the adipocytes of persons with obese type 2 and non-obese type 2 diabetes were examined, the expression levels of the protein were 3 times and 5.5 times, respectively, than that in the normal group, and that the activities of the protein were 71% and 88% of that in the normal group, respectively. Recently, it was reported that PTP-1b knockout mice showed increased sensitivity to insulin and resistance to high-fat diets. In addition, based on a number of studies reported recently, it appears that a substance which inhibits the activity of PTP-1b can increase sensitivity to insulin in target cells to overcome insulin resistance. In the Korea Chemical Bank, high-throughput random screening has been carried out in order to develop PTP-1b inhibitors from tens of thousands of compounds which have not yet been developed into drugs.

Meanwhile, leptin is released from adipocytes into blood, passes through the brain-blood barrier and then acts as a receptor in the central nervous system to suppress food intake, reduce bodyweight and promote energy consumption. Thus, based on the new finding that PTP-1b regulates the activity of leptin itself, it is expected that PTP-1b will exhibit a synergistic effect with a leptin agonist (Koren, S., *Best Pract. Res. Clin. Endocrinol. Metab.*, 21:621, 2007).

Thus, the importance of PTP-1b inhibitors in the development of agents for treating obesity or obese type 2 diabetes is increasing. In recent years, pioneer compounds of PTP-1b inhibitor found by HTS (high-throughput screening) were reported. Until now, studies on PTP-1b and the development of PTP-1b inhibitors have not been clinically successful. However, as shown in Table 3 below, PTP-1b inhibitors are being developed by many research groups and companies.

TABLE 3

| | PTB-1b inhibitors being developed | | | |
|---|---|---|---|---|
| Mechanisms | Names of Medical drugs | Development Companies | Phases | Others |
| Protein tyrosine phosphatase 1B inhibitor | Ertiprotafib | Wyeth | Phase II | Benzenepropanoic acid (discontinued) |
| | SIS-113718 | ISIS Pharmaceuticals | preclinical | $2^{nd}$-generation antisense PTP-1b inhibitor |
| | OS-86839 | Ontogen | preclinical | Selective non-peptide inhibitor of PTP-1b |
| | PTP-1b inhibitor | Abbott | preclinical | Phosphastase-1B inhibitor |
| | PTP-1b inhibitor | Array BioPharma | preclinical | PTP-1b inhibitor |
| | PTP-1b inhibitor | Structural Bioinformatics | preclinical | Orally-active selective PTP-1b inhibitor |
| | PTP-1b inhibitor | Kaken Pharmaceuticals | preclinical | Orally-active PTPase inhibitor |

Excerpt: Pharmaproject, 2002

However, most PTP-1b inhibitors were developed as non-hydrolyzable phosphotyrosine mimetics targeting the active sites of positively charged PTP-1b, and thus have low selectivity and bioavailability (Liu, S. et al., *J. Am. Chem. Soc.*, 130:17075, 2008).

Accordingly, the present inventors have made extensive efforts to develop agents effective for treating obesity and diabetes, and as a result, found that sodium lobarate, which is a salt of lobaric acid separated from an extract of the Antarctic lichen *Stereocaulon alpinum*, is water-soluble and can be easily applied, and in addition to this sodium lobarate, newly synthesized Lobarin and Lobarstin inhibit PTP-1b more effectively than lobaric acid, and act selectively only on PTP-1b among protein tyrosine phosphatases, and also show anti-diabetic effects when they are administered to disease model animals, thereby completing the present invention.

SUMMARY OF INVENTION

It is an object of the present invention to provide a pharmaceutical composition and a functional food for preventing or treating diabetes or obesity, which contains, as an active ingredient, a novel compound synthesized from a compound separated from an extract of *Stereocaulon alpinum*.

Another object of the present invention is to provide a method for preventing or treating diabetes or obesity, the method comprising a step of administering a novel compound synthesized from a compound separated from an extract of *Stereocaulon alpinum*.

Still another object of the present invention is to provide a method for inhibiting the activity of PTP-1b (protein tyrosine phosphatase-1b), the method comprising a step of administering a novel compound synthesized from a compound separated from an extract of *Stereocaulon alpinum*.

Yet another object of the present invention is to provide the use of a novel compound, synthesized from a compound separated from an extract of *Stereocaulon alpinum*, for prevention or treatment of diabetes or obesity.

To achieve the above objects, the present invention provides a compound represented by the following Formula 1:

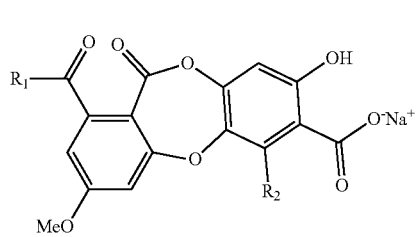

[Formula 1]

wherein $R_1$ and $R_2$ are independently selected from the group consisting of H, an alkyl group, an aryl group, an allyl group, an arylalkyl group, and an acyl group.

The present invention also provides a pharmaceutical composition for preventing or treating diabetes or obesity, which comprises, as an active ingredient, the compound represented by the above Formula 1.

The present invention also provides a functional food for preventing or alleviating diabetes or obesity, which comprises, as an active ingredient, the compound represented by the above Formula 1.

The present invention also provides a compound represented by the following Formula 2:

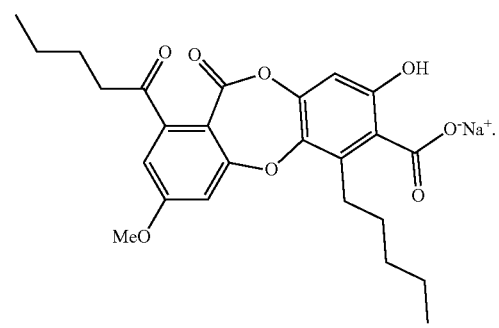

[Formula 2]

Chemical Formula: $C_{25}H_{27}NaO_8$
Molecular Weight: 478.47

The present invention also provides a method for preparing a compound represented by the above Formula 2, the method comprising the steps of:

(a) extracting *Stereocaulon alpinum* with methanol;
(b) eluting the *Stereocaulon alpinum* extract, obtained in step (a), with an aqueous solution of methanol or acetonitrile ($CH_3CN$) by column chromatography;
(c) eluting a fraction, eluted in step (b), with an aqueous solution of acetonitrile ($CH_3CN$) or methanol by reverse-phase high-performance liquid chromatography to obtain a lobaric acid-containing fraction; and
(d) dissolving the lobaric acid-containing fraction in a solvent, adding $NaHCO_3$, $Na_2CO_3$ or $NaH_2PO_4$ thereto, stirring the mixture, and collecting the compound of the above Formula 2 from the mixture.

The present invention also provides a pharmaceutical composition for preventing or treating diabetes or obesity, the composition comprising the compound of the above Formula 2 as an active ingredient.

The present invention also provides a functional food for preventing or alleviating diabetes or obesity, the food comprising the compound of the above Formula 2 as an active ingredient.

The present invention also provides a compound represented by the following Formula 3:

[Formula 3]

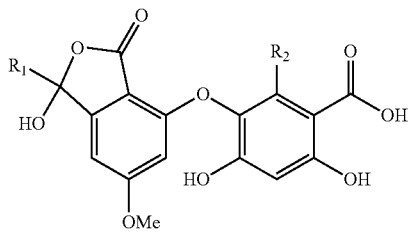

wherein $R_1$ and $R_2$ are independently selected from the group consisting of H, an alkyl group, an aryl group, an allyl group, an arylalkyl group, and an acyl group.

The present invention also provides a pharmaceutical composition for preventing or treating diabetes or obesity, which comprises, as an active ingredient, the compound represented by the above Formula 3 or a pharmaceutically acceptable salt thereof.

The present invention also provides a functional food for preventing or alleviating diabetes or obesity, which comprises, as an active ingredient, the compound represented by the above Formula 3.

The present invention also provides a compound represented by the following Formula 4:

[Formula 4]

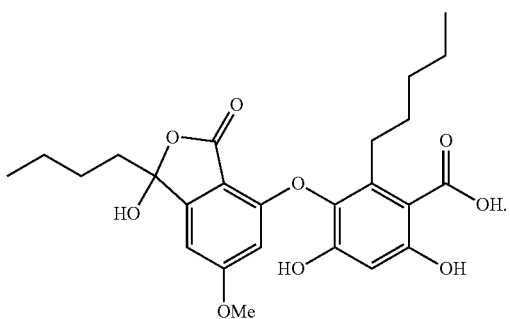

Chemical Formula: $C_{25}H_{30}O_9$
Molecular Weight: 474.5

The present invention also provides a method for preparing the compound represented by Formula 4, the method comprising the steps of:
(a) extracting *Stereocaulon alpinum* with methanol;
(b) eluting the *Stereocaulon alpinum* extract, obtained in step (a), with an aqueous solution of methanol or acetonitrile ($CH_3CN$) by column chromatography;
(c) eluting a fraction, eluted in step (b), with an aqueous solution of acetonitrile ($CH_3CN$) or methanol by reverse-phase high-performance liquid chromatography to obtain a lobaric acid-containing fraction; and
(d) dissolving the lobaric acid-containing fraction in a solvent, adding a base thereto, stirring the mixture to react, adding an acidic solution to the mixture to stop the reaction, and then collecting the compound of Formula 4 from the mixture.

The present invention also provides a pharmaceutical composition for preventing or treating diabetes or obesity, which comprises, as an active ingredient, the compound of the above Formula 4 or a pharmaceutically acceptable salt thereof.

The present invention also provides a functional food for preventing or alleviating diabetes or obesity, which comprises the compound of the above Formula 4 as an active ingredient.

The present invention also provides a compound represented by the following Formula 5:

[Formula 5]

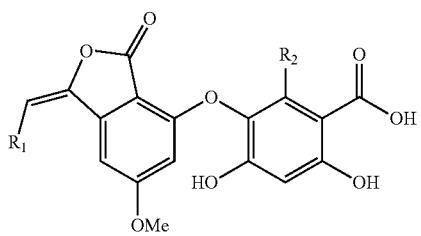

wherein $R_1$ and $R_2$ are independently selected from the group consisting of H, an alkyl group, an aryl group, an allyl group, an arylalkyl group, and an acyl group.

The present invention also provides a pharmaceutical composition for preventing or treating diabetes or obesity, which comprises, as an active ingredient, the compound of the above Formula 5 or a pharmaceutically acceptable salt thereof.

The present invention also provides a functional food for preventing or alleviating diabetes or obesity, which comprises the compound of the above Formula 5 as an active ingredient.

The present invention also provides a compound represented by the following Formula 6:

[Formula 6]

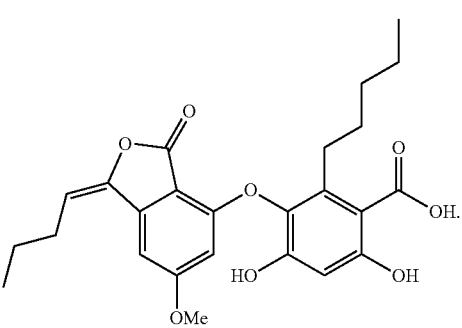

Chemical Formula: $C_{25}H_{28}O_8$
Molecular Weight: 456.49

The present invention also provides a method for preparing the compound represented by the above Formula 6, the method comprising the steps of:
(a) extracting *Stereocaulon alpinum* with methanol;
(b) eluting the *Stereocaulon alpinum* extract, obtained in step (a), with an aqueous solution of methanol or acetonitrile ($CH_3CN$) by column chromatography;
(c) eluting a fraction, eluted in step (b), with an aqueous solution of acetonitrile ($CH_3CN$) or methanol by reverse-phase high-performance liquid chromatography to obtain a lobaric acid-containing fraction; and
(d) dissolving the lobaric acid-containing fraction in a solvent, adding water and a base thereto, stirring the mixture to react, adding an acidic solution to the reaction mixture to stop the reaction, and then collecting the compound of the above Formula 6 from the reaction solution.

The present invention also provides a pharmaceutical composition for preventing or treating diabetes or obesity, comprising, as an active ingredient, the compound of the above Formula 6 or a pharmaceutically acceptable salt thereof.

The present invention also provides a functional food for preventing or alleviating diabetes or obesity, comprising the compound of Formula 6 as an active ingredient.

The present invention also provides a method for preventing or treating diabetes or obesity, comprising a step of administering a compound of Formula 1, 2, 3, 4, 5 or 6, which is a novel compound synthesized from a compound extracted from an extract of *Stereocaulon alpinum*.

The present invention also provides the use of a compound of Formula 1, 2, 3, 4, 5 or 6, which is a novel compound synthesized from a compound extracted from an extract of *Stereocaulon alpinum*, for prevention or treatment of diabetes or obesity.

The present invention also provides a method of inhibiting the activity of PTP-1b using a compound of Formula 1, 2, 3, 4, 5 or 6, which is a novel compound synthesized from a compound extracted from an extract of *Stereocaulon alpinum*.

The present invention also provides a composition for inhibiting the activity of PTP-1b, the composition comprising the compound of Formula 1, 2, 3, 4, 5 or 6, which is a novel compound synthesized from a compound extracted from an extract of *Stereocaulon alpinum*.

Other features and embodiments of the present invention will be more apparent from the following detailed descriptions and the appended claims.

BEST MODE FOR CARRYING OUT THE INVENTION

Figure 1:
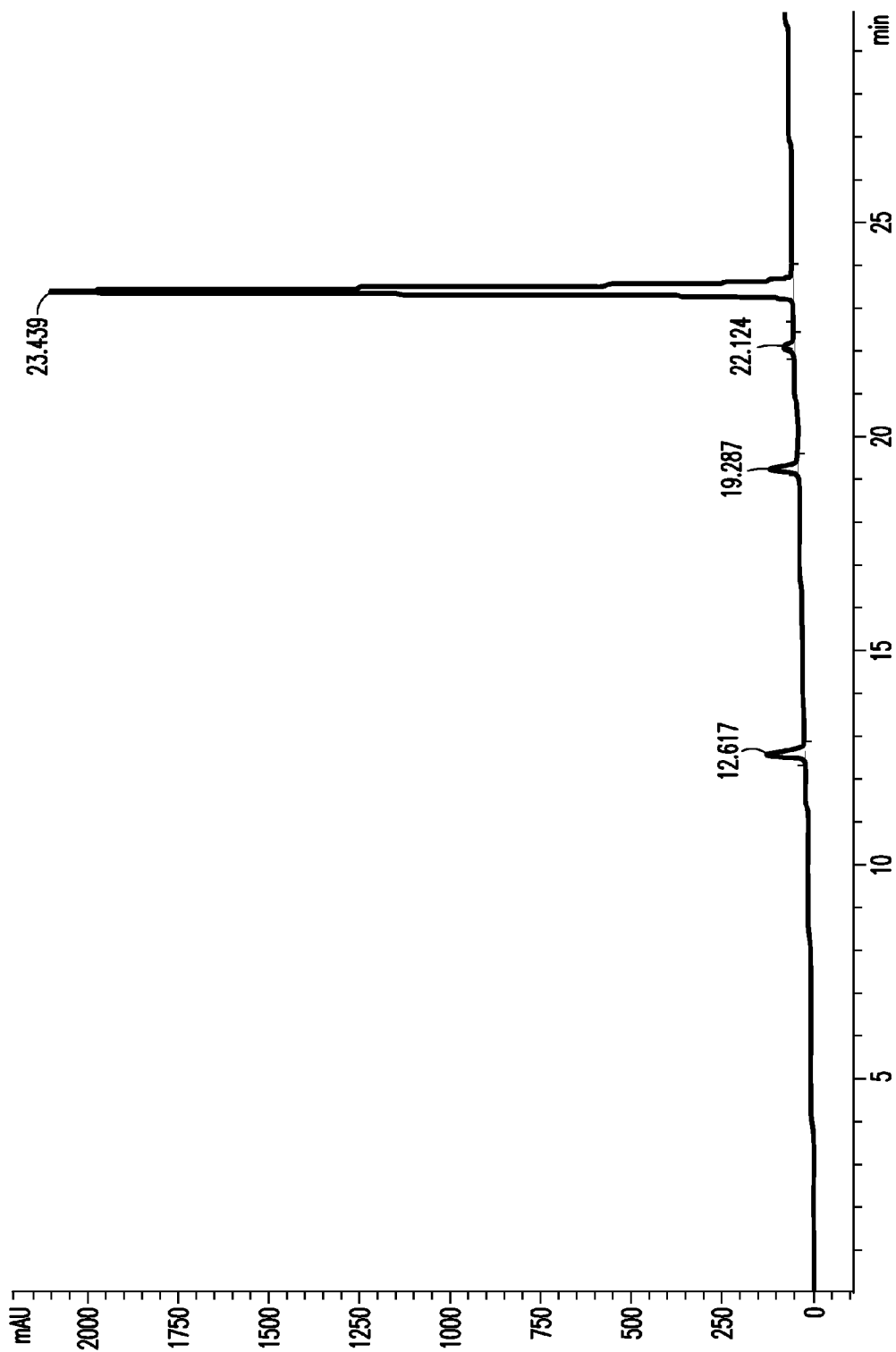
FIG. 1 shows the results of HPLC analysis conducted to examine the purity of sodium lobarate.
Figure 2A:
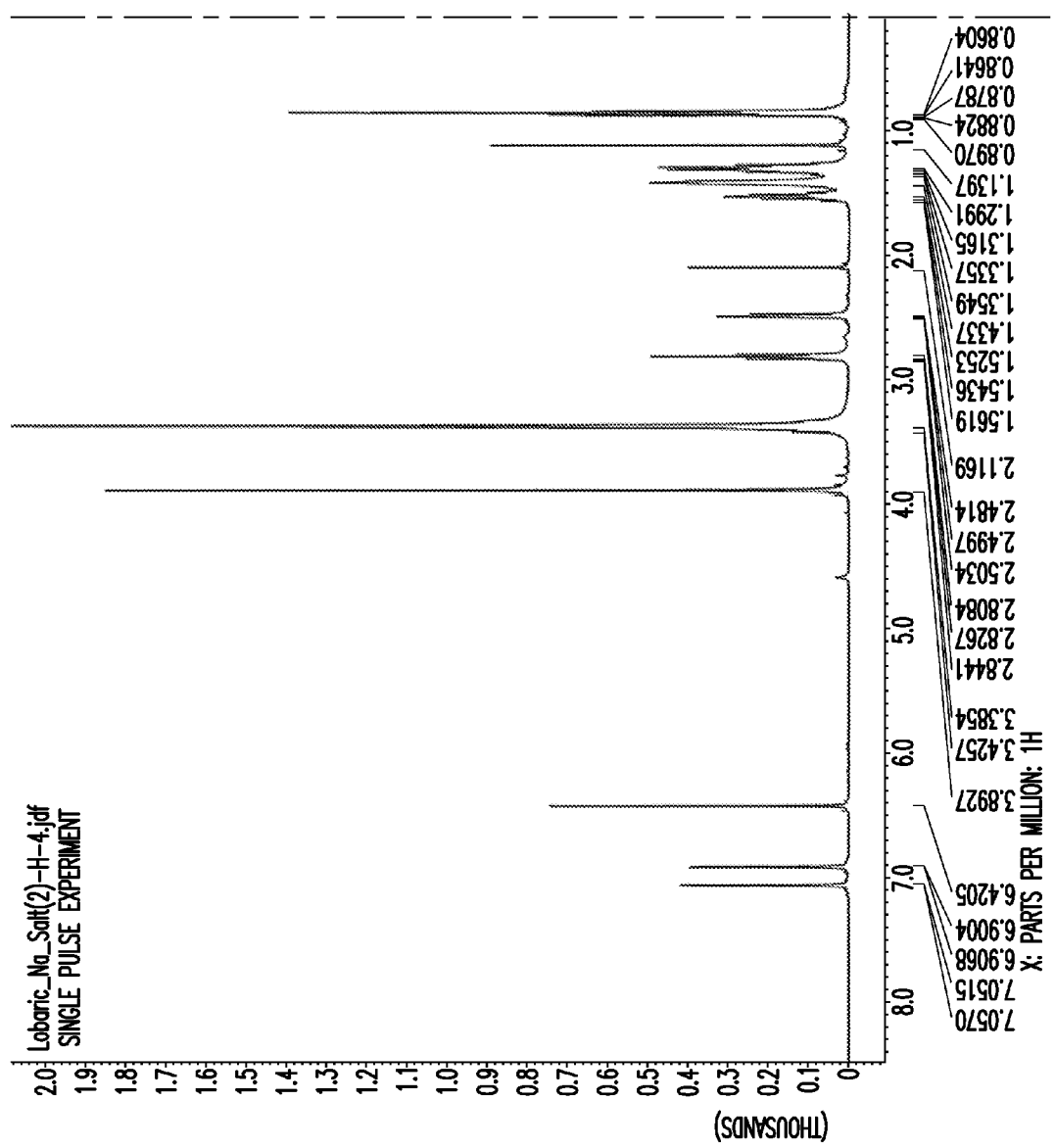
FIG. 2 shows the $^1$H NMR spectrum (400 MHz, DMSO-$d_6$) of sodium lobarate.
Figure 3A:
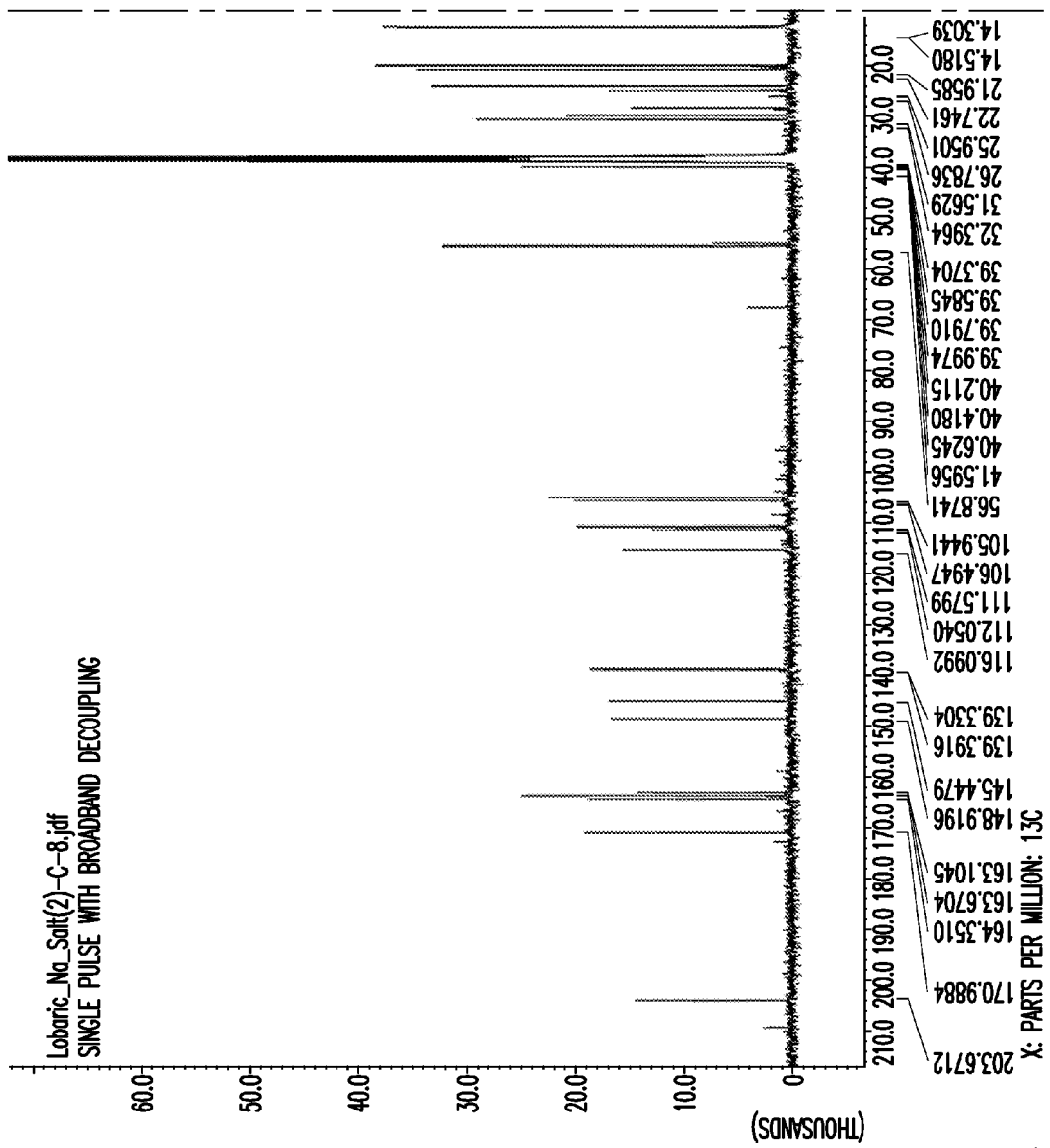
FIG. 3 shows the $^{13}$C NMR spectrum (100 MHz, DMSO-$d_6$) of sodium lobarate.
Figure 4A:
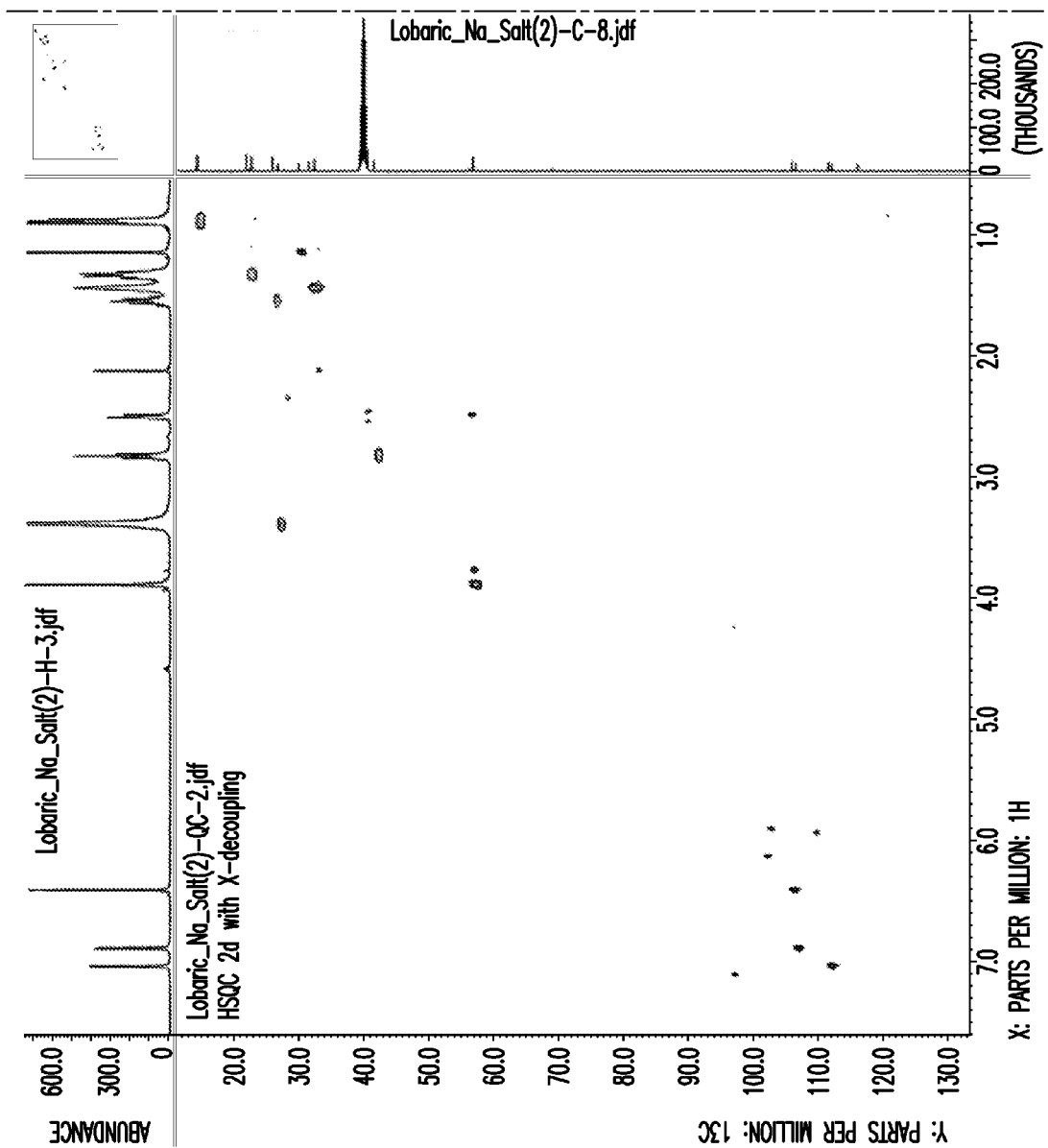
FIG. 4 shows HSQC data (400 MHz, DMSO-$d_6$) for sodium lobarate.
Figure 5A:
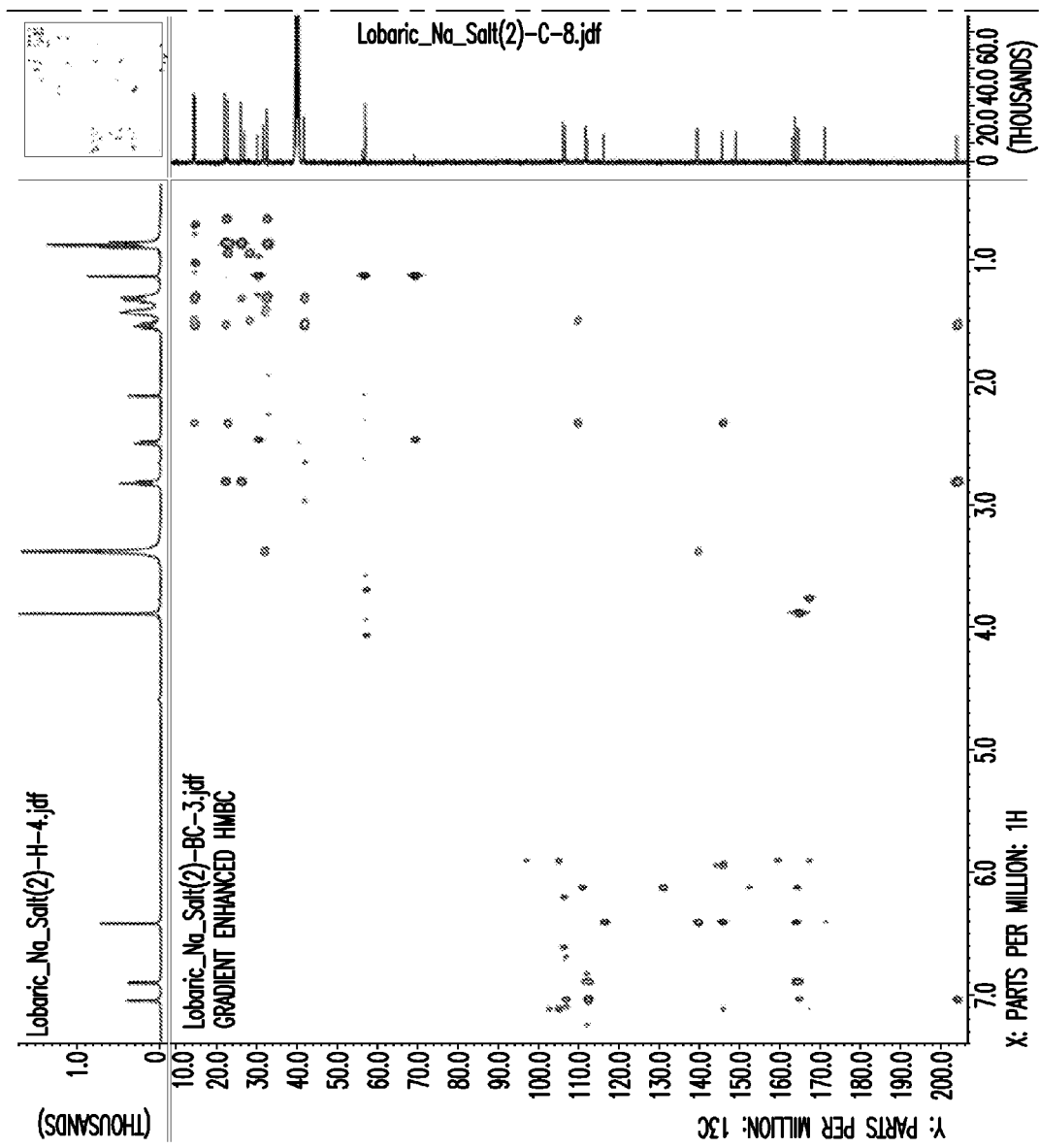
FIG. 5 shows HMBC data (400 MHz, DMSO-$d_6$) for sodium lobarate.

Unless defined otherwise, all technical and scientific terms used herein have the same meaning as commonly understood by one of ordinary skill in the art to which the invention pertains. Generally, the nomenclature used herein and the experimental methods which will be described later are those well known and commonly employed in the art.

In the present invention, a sodium lobarate represented by the following Formula 2, which is a salt of lobaric acid, was obtained from the lobaric acid separated from an extract of *Stereocaulon alpinum*:

[Formula 2]

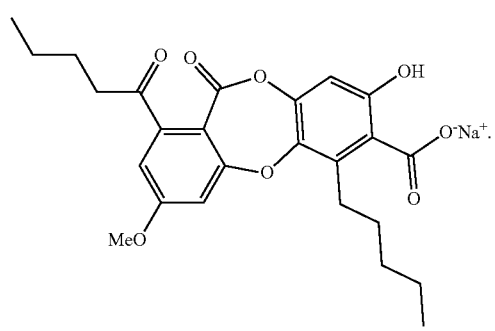

Chemical Formula: $C_{25}H_{27}NaO_8$
Molecular Weight: 478.47

Preferably, the sodium lobarate represented by the above Formula 2 may be prepared by a method comprising the following steps of:
(a) extracting *Stereocaulon alpinum* with methanol;
(b) eluting the *Stereocaulon alpinum* extract, obtained in step (a), with an aqueous solution of methanol or acetonitrile ($CH_3CN$) by column chromatography;
(c) eluting a fraction, eluted in step (b), with an aqueous solution of acetonitrile ($CH_3CN$) or methanol by reverse-phase high-performance liquid chromatography to obtain a lobaric acid-containing fraction; and
(d) dissolving the lobaric acid-containing fraction in a solvent, adding $NaHCO_3$, $Na_2CO_3$ or $NaH_2PO_4$ thereto, stiffing the mixture, and collecting the compound of the above Formula 2 from the mixture.

Preferably, the step (d) of the method may be performed by dissolving the lobaric acid-containing fraction in acetone, adding $NaHCO_3$, $Na_2CO_3$ or $NaH_2PO_4$ thereto, stiffing the mixture, filtering the solid precipitated on adding the $NaHCO_3$, $Na_2CO_3$ or $NaH_2PO_4$, and concentrating the filtrate, thereby obtaining the compound of Formula 2.

In one embodiment of the present invention, the Antarctic lichen *Stereocaulon alpinum* (*Stereocaulon alpinum* (Hedw.) G.L. Sm.) used in the present invention was collected from the area around the King Sejong Station (S 62°13.3°, W58°47.0°) located on Barton Peninsula on King George Island, Antarctica, in January 2003. Lobaric acid was obtained by extracting dried *Stereocaulon alpinum* with methanol for 24 hours, evaporating the solvent to obtain the extract, loading the extract onto a flash column chromatography (5×25 cm) packed with silica gel ($C_{18}$), sequentially injecting 10%, 20%, 30%, 40%, 50%, 60%, 70%, 80%, 90% and 100% (v/v) methanol (MeOH) onto the column, collecting the respective methanol fractions, selecting a fraction showing excellent PTP-1b inhibitory activity from the collected fractions, and separating a lobaric acid of the following Formula 7, which has excellent PTP-1b inhibitory activity, from the selected fraction.

[Formula 7]

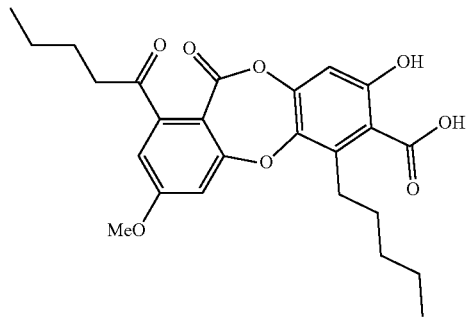

Chemical Formula: $C_{25}H_{28}O_8$
Molecular Weight: 456.49

Lobaric acid can be obtained by extracting *Stereocaulon alpinum* with methanol, eluting the *Stereocaulon alpinum* extract in an aqueous methanol solution by column chromatography, and eluting the eluted fraction with an aqueous acetonitrile ($CH_3CN$) solution by reverse-phase high-performance liquid chromatography. Sodium lobarate can be obtained by dissolving the obtained lobaric acid in acetone, adding $NaHCO_3$, $Na_2CO_3$ or $NaH_2PO_4$ thereto, stirring the mixture, filtering the solid precipitated on adding the $NaHCO_3$, $Na_2CO_3$ or $NaH_2PO_4$, and completely concentrating the filtrate by a rotary evaporator, thereby obtaining a sodium lobarate of the following Formula 2.

[Formula 2]

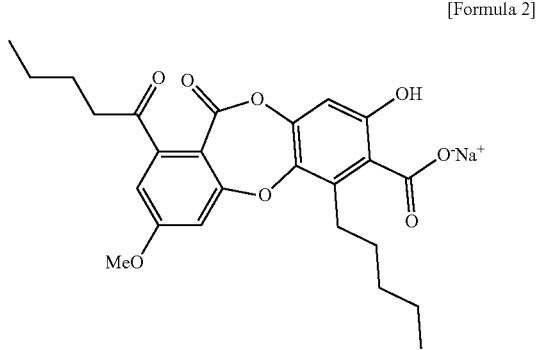

Chemical Formula: $C_{25}H_{27}NaO_8$
Molecular Weight: 478.47

The PTP-1b inhibitory activity of the sodium lobarate has not yet been reported and the effects of the sodium lobarate on the treatment of diabetes or obesity have not yet been reported.

In addition, derivatives of the sodium lobarate of Formula 2, obtained by modifying some of the alkyl groups, will also fall within the scope of the present invention. In this aspect, the present invention is directed to a compound represented by the following Formula 1:

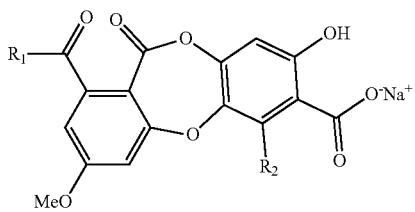

[Formula 1]

wherein $R_1$ and $R_2$ are independently selected from the group consisting of H, an alkyl group, an aryl group, an allyl group, an arylalkyl group, and an acyl group.

The alkyl, aryl, allyl, arylalkyl and acyl groups may, for example, contain 1-20 carbon atoms or 1-10 carbon atoms, wherein examples of the alkyl group include substituted or unsubstituted alkyl and cycloalkyl groups.

It will be obvious to those skilled in the art to obtain a compound of Formula 1 from the sodium lobarate of Formula 2 by a chemical synthesis or modification thereof known in the art. For example, it may be obtained derivatives of the compound of Formula 1 by the modification of the number of carbon atom of R and coupling structures. For example, the sodium lobarate of Formula 2 can be reacted with sodium pentanoate to provide a compound of Formula 1 wherein $R_1$ and $R_2$ are propyl chains. In addition, the sodium lobarate of Formula 2 can be reacted with sodium butyrate, sodium propionate, sodium hexanoate or the like, which has different number of carbon atoms compared to sodium pentanoate, thereby synthesizing various derivatives.

In the present invention, it is found that a sodium lobarate, a salt of the lobaric acid separated from an extract of Stereocaulon alpinum, has excellent PTP-1b (protein tyrosine phosphatase-1b) inhibitory activity compared to lobaric acid, and thus is effective in preventing or treating diabetes or obesity. Accordingly, in another aspect, the present invention is directed to a pharmaceutical composition for preventing or treating diabetes or obesity, which comprises the sodium lobarate as an active ingredient. In addition, the present invention may provide a functional food comprising the sodium lobarate as an active ingredient. Thus, in another aspect, the present invention is directed to a functional food for preventing or alleviating diabetes or obesity, which comprises the sodium lobarate as an active ingredient.

Moreover, the sodium lobarate of Formula 2, and the compound of Formula 1, obtained by modifying some of alkyl groups, or a pharmaceutically acceptable salt thereof, will exhibit the same or similar effects, and thus these can provide pharmaceutical compositions or functional foods for preventing or treating diabetes or obesity.

In one Example of the present invention, the inhibitory activity of sodium lobarate against PTP-1b was analyzed comparatively with that of lobaric acid. As a result, it was found that the $IC_{50}$ of lobaric acid was 870 nM, whereas the $IC_{50}$ of sodium lobarate was 350 nM, suggesting that sodium lobarate has very excellent effect on the inhibition of PTP-1b. Thus, it was found that sodium lobarate is a compound capable of treating and preventing diabetes or obesity.

In one Example of the present invention, selectivities of sodium lobrate for a group of protein tyrosine phosphatases were examined.

In other Examples of the present invention, the relationship of sodium lobarate with insulin resistance was examined by administering sodium lobarate to the diabetic animal model db/db mice and measuring the change in the blood glucose levels and blood insulin level of the mice. As a result, it was demonstrated that sodium lobarate has anti-diabetic effects.

Moreover, in the present invention, a novel compound represented by the following Formula 4 was separated from an extract of Stereocaulon alpinum, and was named "Lobarin".

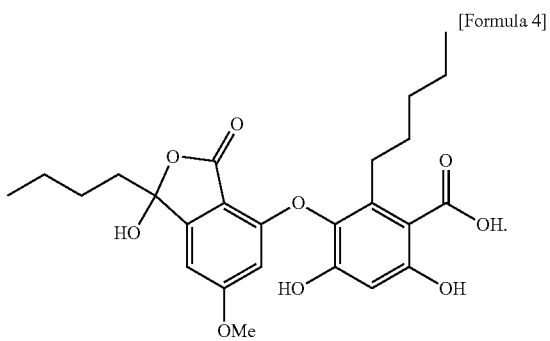

[Formula 4]

Chemical Formula: $C_{25}H_{30}O_9$
Molecular Weight: 474.5

Preferably, the Lobarin represented by the above Formula 4 may be prepared by a method comprising the following steps of:

(a) extracting Stereocaulon alpinum with methanol;

(b) eluting the Stereocaulon alpinum extract, obtained in step (a), with an aqueous solution of methanol or acetonitrile ($CH_3CN$) by column chromatography;

(c) eluting a fraction, eluted in step (b), with an aqueous solution of acetonitrile ($CH_3CN$) or methanol by reverse-phase high-performance liquid chromatography to obtain a lobaric acid-containing fraction; and (d) dissolving the lobaric acid-containing fraction in a solvent, adding a base thereto, stirring the mixture to react, adding an acidic solution to the mixture to stop the reaction, and then collecting the compound of the above Formula 4 from the mixture.

Herein, the acidic solution that is used in step (d) may be any acidic solution which can neutralize an aqueous solution. Preferably, in step (d), the solvent may be acetone, the base may be NaOH or KOH, and the acidic solution may be a HCl solution, a $H_2SO_4$ solution or a $HNO_3$ solution. In step (d), the compound may be collected by concentrating the acidic solution-containing mixture, partitioning the concentrate between methylene chloride, chloroform or ethylene chloride or an aqueous solution to obtain a methylene chloride, chloroform or ethylene chloride layer, and concentrating the obtained layer.

In one embodiment of the present invention, Lobarin can be obtained by dissolving lobaric acid in acetone, adding NaOH thereto, stirring the mixture to react, adding a HCl solution to the reaction mixture to stop the reaction, concentrating the reaction mixture, partitioning the concentrate between methylene chloride and an aqueous solution (pH=2), and collecting the methylene chloride layer, thereby Lobarin of the following Formula 4.

[Formula 4]

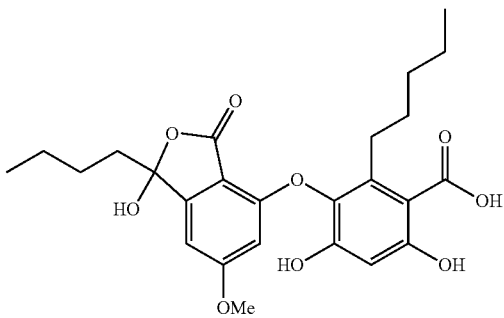

Chemical Formula: C$_{25}$H$_{30}$O$_9$
Molecular Weight: 474.5

In addition, derivatives of Lobarin of Formula 4, obtained by modifying some of the alkyl groups, will also fall within the scope of the present invention. In this aspect, the present invention is directed to a compound represented by the following Formula 3:

[Formula 3]

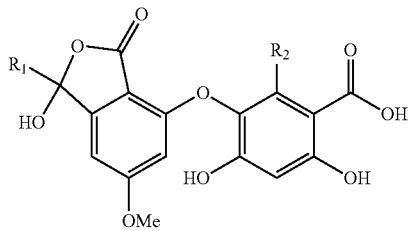

wherein R$_1$ and R$_2$ are independently selected from the group consisting of H, an alkyl group, an aryl group, an allyl group, an arylalkyl group, and an acyl group.

The alkyl, aryl, allyl, arylalkyl and acyl groups may, for example, contain 1-20 carbon atoms or 1-10 carbon atoms, wherein examples of the alkyl group include substituted or unsubstituted alkyl and cycloalkyl groups.

It will be obvious to those skilled in the art to obtain a compound of Formula 3 from Lobarin of Formula 4 by a chemical synthesis or modification method known in the art. For example, Lobarin of Formula 4 can be modified to provide compounds of Formula 3 wherein R$_1$ and R$_2$ have various carbon atoms and structures. For example, Lobarin of Formula 4 can be reacted with sodium pentanoate to provide a compound of Formula 3 wherein R$_1$ and R$_2$ are propyl chains. In addition, Lobarin of Formula 4 can be reacted with sodium butyrate, sodium propionate, sodium hexanoate or the like, which has a carbon atom different from that that of sodium pentanoate, thereby synthesizing various derivatives.

In the present invention, it was found that Lobarin, a novel derivative of the lobaric acid separated from an extract of Stereocaulon alpinum, has excellent PTP-1b inhibitory activity, and thus is effective in preventing or treating diabetes or obesity. Thus, in another aspect, the present invention is directed to a pharmaceutical composition for preventing or treating diabetes or obesity, which comprises Lobarin of Formula 4 or a pharmaceutically acceptable salt thereof as an active ingredient. Moreover, the present invention may provide a functional food comprising Lobarin as an active ingredient. Thus, in another aspect, the present invention is directed to a functional food for preventing or alleviating diabetes or obesity, which comprises Lobarin as an active ingredient.

Moreover, Lobarin of Formula 4, and the compound of Formula 3, obtained by modifying some of alkyl groups, or a pharmaceutically acceptable salt thereof, will exhibit the same or similar effects, and thus these can provide pharmaceutical compositions or functional foods for preventing or treating diabetes or obesity.

In one Example of the present invention, the inhibitory activity of Lobarin against PTP-1b was measured. As a result, it was found that the IC$_{50}$ of Lobarin was 149 nM, suggesting that Lobarin has a very excellent effect on the inhibition of PTP-1b. Thus, it was found that a novel compound Lobarin is a compound capable of treating and preventing diabetes or obesity.

In one Example of the present invention, the selectivity of Lobarin for protein tyrosine phosphatases was examined. As a result, it was found that Lobarin acts selectively only on PTP-1b among protein tyrosine phosphatases, including TC-PTP (PTPN2), which is known to be most similar to PTP-1b in terms of the amino acid sequence and the 3D structure, induces embryonic lethality, has enzymatic characteristics similar to PTP-1b, and has active sites (including a second aryl-phosphate binding site) similar to those of TC-PTP. Such test results suggest that Lobarin which is the compound according to the present invention is a PTP-1b inhibitor which can be used to treat diabetes.

In other Examples of the present invention, the relationship of Lobarin with insulin resistance was examined by administering Lobarin to the diabetic animal model db/db mice and measuring the change in the blood glucose levels and blood insulin level of the mice. As a result, it was demonstrated that Lobarin has anti-diabetic effects.

Meanwhile, in the present invention, Lobarin of Formula 4 may be in the form of a pharmaceutically acceptable salt. Pharmaceutically acceptable salts of Lobarin can be prepared by a conventional method in the art, and examples thereof include salts with inorganic salts with inorganic acids, such as hydrochloric acid, hydrobromide, sulfuric acid, sodium hydrogen sulfate, phosphoric acid or carbonic acid; salts with organic acids, such as formic acid, acetic acid, oxalic acid, benzoic acid, citric acid, tartaric acid, gluconic acid, gentisic acid, fumaric acid, lactobionic acid, salicylic acid, or acetyl-salicyclic acid (aspirin); salts with alkali metal ions, such as sodium or potassium ions; and salts with ammonium.

In addition, a novel compound represented by the following Formula 6 was separated from the lobaric acid separated from an extract of Stereocaulon alpinum, and was named "Lobarstin".

[Formula 6]

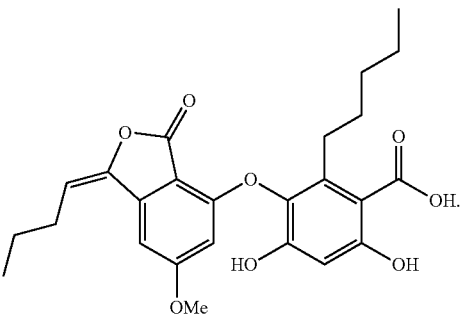

Chemical Formula: C$_{25}$H$_{28}$O$_8$
Molecular Weight: 456.49

The novel compound Lobarstin represented by the above Formula 6 may be prepared by a method comprising the following steps of:

(a) extracting *Stereocaulon alpinum* with methanol;

(b) eluting the *Stereocaulon alpinum* extract, obtained in step (a), with an aqueous solution of methanol or acetonitrile ($CH_3CN$) by column chromatography;

(c) eluting a fraction, eluted in step (b), with an aqueous solution of acetonitrile ($CH_3CN$) or methanol by reverse-phase high-performance liquid chromatography to obtain a lobaric acid-containing fraction; and (d) dissolving the lobaric acid-containing fraction in a solvent, adding water and a base added thereto, stirring the mixture to react, adding an acidic solution to the reaction mixture to stop the reaction, and then collecting the compound of the above Formula 6 from the reaction solution.

Herein, the acidic solution that is used in step (d) may be any acidic solution which can neutralize an aqueous solution. Preferably, in step (d), the solvent may be acetone, the base may be NaOH or KOH, and the acidic solution may be a HCl solution, a $H_2SO_4$ solution or a $HNO_3$ solution. In step (d), the compound may be collected by concentrating the acidic solution-containing mixture, partitioning the concentrate between methylene chloride, chloroform or ethylene chloride or an aqueous solution to obtain a methylene chloride, chloroform or ethylene chloride layer, and concentrating the obtained layer.

In one embodiment of the present invention, Lobarstin can be obtained by dissolving lobaric acid in acetone, adding NaOH thereto, stirring the mixture to react, adding a HCl solution to the reaction mixture to stop the reaction, concentrating the reaction mixture, partitioning the concentrate between methylene chloride and an aqueous solution (pH=2), and collecting the methylene chloride layer, thereby Lobarin of the following Formula 6.

[Formula 6]

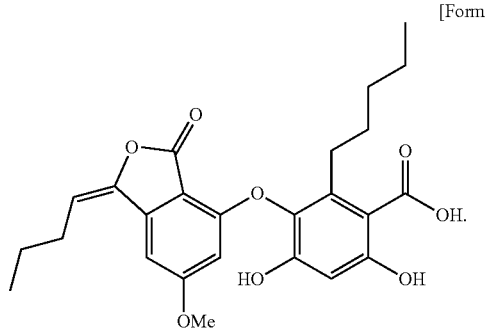

Chemical Formula: $C_{25}H_{28}O_8$
Molecular Weight: 456.49

Moreover, derivatives of Lobarstin of Formula 6, obtained by modifying some of the alkyl groups, will also fall with the scope of the present invention. In this aspect, the present invention is directed to a compound of the following Formula 5:

[Formula 5]

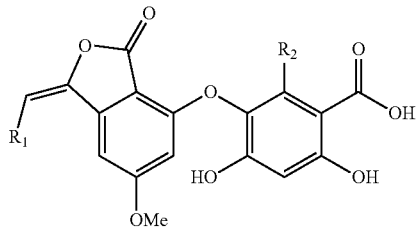

wherein $R_1$ and $R_2$ are independently selected from the group consisting of H, an alkyl group, an aryl group, an allyl group, an arylalkyl group, and an acyl group.

The alkyl, aryl, allyl, arylalkyl and acyl groups may, for example, contain 1-20 carbon atoms or 1-10 carbon atoms, wherein examples of the alkyl group include substituted or unsubstituted alkyl and cycloalkyl groups.

It will be obvious to those skilled in the art to obtain the compound of Formula 5 from Lobarstin of Formula 6 by a chemical synthesis or modification method known in the art. For example, the compound of Formula 5 can be modified to provide compounds of Formula 5 wherein $R_1$ and $R_2$ have various carbon atoms and structures. For example, Lobarstin of Formula 6 can be reacted with sodium pentanoate to provide a compound of Formula 5 wherein $R_1$ and $R_2$ are propyl chains. In addition, Lobarstin of Formula 6 can be reacted with sodium butyrate, sodium propionate, sodium hexanoate or the like, which has a carbon atom different from that that of sodium pentanoate, thereby synthesizing various derivatives.

In the present invention, it was found that Lobarstin, a novel derivative of the lobaric acid separated from an extract of *Stereocaulon alpinum*, has excellent PTP-1b inhibitory activity, and thus is effective in preventing or treating diabetes or obesity. Thus, in another aspect, the present invention is directed to a pharmaceutical composition for preventing or treating diabetes or obesity, which comprises Lobarstin of Formula 6 or a pharmaceutically acceptable salt thereof as an active ingredient. Moreover, the present invention may provide a functional food comprising Lobarstin as an active ingredient. Thus, in another aspect, the present invention is directed to a functional food for preventing or alleviating diabetes or obesity, which comprises Lobarstin as an active ingredient.

Moreover, Lobarstin of Formula 6, and the compound of Formula 5, obtained by modifying some of alkyl groups, or a pharmaceutically acceptable salt thereof, will exhibit the same or similar effects, and thus these can provide pharmaceutical compositions or functional foods for preventing or treating diabetes or obesity.

In one Example of the present invention, the inhibitory activity of Lobarstin against PTP-1b was measured. As a result, it was found that the $IC_{50}$ of Lobarin was 154.6 nM, suggesting that Lobarstin has a very excellent effect on the inhibition of PTP-1b. Thus, it was found that a novel compound Lobarstin is a compound capable of treating and preventing diabetes or obesity.

In one Example of the present invention, the selectivity of Lobarin for protein tyrosine phosphatases was examined. As a result, it was found that Lobarin acts selectively only on PTP-1b among protein tyrosine phosphatases, including TC-PTP (PTPN2), which is known to be most similar to PTP-1b in terms of the amino acid sequence and the 3D structure, induces embryonic lethality, has enzymatic characteristics similar to PTP-1b, and has active sites (including a second aryl-phosphate binding site) similar to those of TC-PTP. Such test results suggest that Lobarin which is the compound according to the present invention is a PTP-1b inhibitor which can be used to treat diabetes.

In other Examples of the present invention, the relationship of Lobarstin with insulin resistance was examined by administering Lobarstin to the diabetic animal model db/db mice and measuring the change in the blood glucose levels and blood insulin level of the mice. As a result, it was demonstrated that Lobarstin has anti-diabetic effects.

Meanwhile, in the present invention, Lobarstin of Formula 6 may be in the form of a pharmaceutically acceptable salt. Pharmaceutically acceptable salts of Lobarin can be prepared by a conventional method in the art, and examples thereof include salts with inorganic salts with inorganic acids, such as hydrochloric acid, hydrobromide, sulfuric acid, sodium hydrogen sulfate, phosphoric acid or carbonic acid; salts with organic acids, such as formic acid, acetic acid, oxalic acid, benzoic acid, citric acid, tartaric acid, gluconic acid, gentisic acid, fumaric acid, lactobionic acid, salicylic acid, or acetylsalicyclic acid (aspirin); salts with alkali metal ions, such as sodium or potassium ions; and salts with ammonium.

The pharmaceutical composition comprising the compound according to the present invention can be formulated according to a conventional method. For example, it may be formulated in the form of powders, granules, tablets, capsules, suspensions, emulsions, syrups, aerosols, agents for Oral administration, external applications, suppositories, and sterile injection solutions. Carriers, excipients and diluents that can be contained in the composition comprising the compound according to the present invention include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, and mineral oil.

A pharmaceutical composition comprising the compound according to the present invention is formulated using diluents or excipients, such as fillers, extenders, binders, wetting agents, disintegrants or surfactants, which are commonly used. Solid Formulations for oral administration include tablets, pills, powders, granules, capsules, etc. Such Formulations are prepared by mixing the compound of present invention with at least one excipient, such as starch, calcium carbonate, sucrose, lactose, gelatin, etc. In addition to simple expedients, lubricants such as magnesium stearate, talc, etc. may also be added. Liquid Formulations for oral administration, such as suspensions, internal solutions, emulsions, syrups, etc., may comprise simple diluents, e.g., water and liquid paraffin, as well as various excipients, e.g., wetting agents s, sweeteners, aromatics, preservatives, etc. Formulations for parenteral administration include sterilized aqueous solutions, non-aqueous solvents, suspensions, emulsions, lyophilized agents, suppositories, etc. Non-aqueous solvents and suspensions may be prepared using propylene glycol, polyethylene glycol, vegetable oils such as olive oil, or injectable esters such as ethyloleate. As a base for suppositories, Witepsol, Macrogol, Tween 61, cacao fat, laurin fat, glycerogelatin, etc. may be used.

Examples of the functional food of the present invention include various foods, candies, chocolates, beverages, gums, teas, vitamin complexes, health supplement foods, and the like, and the functional food can be used in the form of powders, granules, tablets, capsules or beverages.

The compound of the present invention may be added to foods or beverages for prevention of diabetes and obesity. With respect to the content of the compound in food or a beverage, the compound of the present invention may generally be added in an amount of 0.01-50 wt %, and preferably 0.1-20 wt %, based on the total weight of the health functional food of the present invention, and the compound of the present invention may be added in an amount of 0.02-10 g, and preferably 0.3-1 g, based on 100 ml of the health beverage composition of the present invention.

Providing that the health beverage composition of the present invention comprises the compound of the present invention as an essential ingredient, there is no particular limitation in other liquid components of the beverage composition, and the composition may further comprise one or more additives, such as various flavors or natural carbohydrates which are commonly used in beverages. Examples of natural carbohydrates for such purposes include common sugars such as monosaccharides, for example, glucose, fructose and the like; disaccharides, for example, maltose, sucrose and the like; and polysaccharides, for example, dextrine, cyclodextrine and the like, and sugar alcohols such as xylitol, sorbitol, erythritol and the like. In addition to the foregoing, as the flavors, natural flavors (thaumatin, stevia extract (for example, Rebaudioside A, glycyrrhizin and the like), and synthetic flavors (saccharine, aspartame and the like) may be advantageously used. The content of the natural carbohydrate in the composition of the present invention is about 1-20 g, and preferably about 5-12 g, based on 100 ml of the composition. In addition, the composition of the present invention may further contain various nutrients, vitamins, minerals (electrolytes), seasonings (artificial seasonings and natural seasonings), coloring agents and improving agents (cheese, chocolate and the like), pectic acid and salts thereof, alginic acid and salts thereof, organic acids, protective colloid thickeners, pH controllers, stabilizers, preservatives, glycerin, alcohols, carbonating agents used in carbonated beverages, and the like. In addition, the composition of the present invention may further contain fruit fresh for preparation of natural fruit juice beverages, fruit juice beverages and vegetable beverages. These additives may be used independently or in combination. Although the content of these additives in the composition of the present invention is not particularly important to the present invention, it is generally selected within the range of 0-20 parts by weight based on 100 parts by weight of the composition of the present invention.

In another aspect, the present invention is directed to a method for preventing or treating diabetes or obesity, comprising a step of administering a compound of Formula 1, 2, 3, 4, 5 or 6, which is a novel compound synthesized from a compound extracted from an extract of *Stereocaulon alpinum*.

The preferred dosage of the novel compound of Formula 1, 2, 3, 4, 5 or 6 according to the present invention can vary depending on various factors, including the patient's condition and weight, the severity of disease, dosage form, the route of administration and the time of administration, and can be suitably determined by a person skilled in the art. In order to achieve the desired effects, however, the compound of the present invention may be administered at a daily dose of from 0.1 to 1,000 µg/kg, and preferably 1-100 µg/kg. The compound may be administered in a single dose per day or in multiple doses per day. The dosage is not intended to limit the present invention in any way.

In another aspect, the present invention is directed to the use of a compound of Formula 1, 2, 3, 4, 5 or 6, which is a novel compound synthesized from a compound extracted from an extract of *Stereocaulon alpinum*, for prevention or treatment of diabetes or obesity.

In the present invention, sodium lobarate, Lobarin and Lobarstin, synthesized from the compound separated from an extract of *Stereocaulon alpinum* according to the present invention, show excellent PTP-1b inhibitory activities. Thus, the present invention is directed to methods of inhibiting the activity of PTP-1b using sodium lobarate, Lobarin and Lobarstin. Specifically, the present invention is directed to a method for inhibiting the activity of PTP-1b, comprising a step of administering, to a subject, a compound of Formula 1, 2, 3, 4, 5 or 6, which is a novel compound synthesized from a compound extracted from an extract of *Stereocaulon alpinum*.

The present invention is also directed to a composition for inhibiting the activity of PTP-1b, the composition comprising the compound of Formula 1, 2, 3, 4, 5 or 6, which is a novel compound synthesized from a compound extracted from an extract of *Stereocaulon alpinum*.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Preparation of Lobaric Acid from the Extract of Antarctic Lichen *Stereocaulon alpinum*

1-1: Preparation of an Extract of Antarctic Lichen *Stereocaulon alpinum*

The Antarctic lichen *Stereocaulon alpinum* (*Stereocaulon alpinum* (Hedw.) G.L. Sm.) used in the present invention was collected from the area around the King Sejong Station (S 62°13.3°, W58°47.0°) located on Barton Peninsula on King George Island, Antarctica, in January 2003.

50 g of dried *Stereocaulon alpinum* was extracted twice with 1 L of methanol for 24 hours to obtain 3.6 g of a methanol extract. The obtained extract was loaded onto flash column chromatography (5×25 cm) packed with silica gel ($C_{18}$) and was subjected to concentration gradient of 10%, 20%, 30%, 40%, 50%, 60%, 70%, 80%, 90% and 100% (v/v) methanol (MeOH) stepwise, and each methanol fraction was collected.

1-2: Preparation of Lobaric Acid from the Extract of Antarctic Lichen *Stereocaulon alpinum*

204.6 mg of the fraction, obtained by elution with 80% methanol in Example 1-1, was loaded onto flash column chromatography (2.5×30 cm) packed with silica gel ($C_{18}$), and 200 Ml of each solution of 1%, 2%, 3%, 4%, 5%, 6%, 7%, 8%, 9% and 10% and 100% (v/v) methanol in $CH_2Cl_2$ was injected into the column in order to obtain 8 main fractions shown in TLC analysis, and each fraction was collected.

59 mg of the fraction eluted with 9% methanol was loaded onto semi-preparative reverse-phase HPLC, and then eluted for 30 minutes or more by a concentration gradient of 75-83% using an aqueous acetonitrile ($CH_3CN$) solution containing 0.1% formic acid, thereby separating a lobaric acid of the following Formula 7 from the fraction (22.9 mg; $t_R$=39 min).

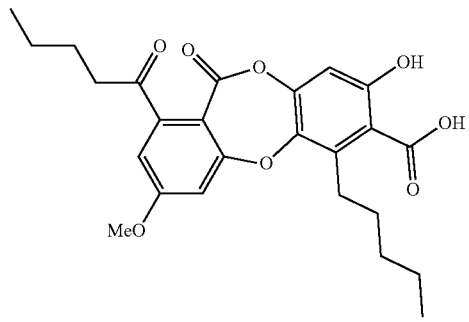

[Formula 7]

Chemical Formula: $C_{25}H_{28}O_8$
Molecular Weight: 456.49

Example 2

Synthesis of Sodium Lobarate 2-1: Preparation of Sodium Lobarate from Lobaric Acid 10 mg (22 umol) of the lobaric acid obtained in Example 1-2 was dissolved in 3 ml of acetone, and 50 ul of 1M $NaHCO_3$ was added thereto, followed by stiffing for 1-2 minutes. The solid precipitated on adding the $NaHCO_3$ was filtered out, immediately after which it was completely concentrated by a rotary evaporator. After completion of the concentration, sodium lobarate (<10 mg) could be obtained as a white solid. Then, in order to remove excess salt from the product to increase the purity, the product was analyzed by reverse phase HPLC using Agilent Eclipse XDB-C18 column (4.6×150 mm, USA). The solvent system used in the analysis was composed of line A and line B which supplied 0.1% formic acid-containing water and 0.1% formic acid-containing acetonitrile, respectively. The elution conditions were as follows: 40% to 50% acetonitrile for 5 min; 50% to 80% acetonitrile for 15 min; and 80% to 90% acetonitrile for 10 min. The final purity was 92.1% (see FIG. 1). The obtained sodium lobarate was dissolved in water, suggesting that it is water-soluble.

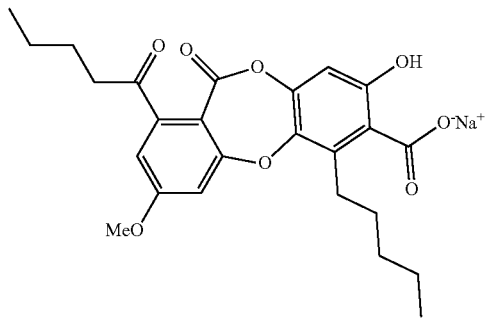

[Formula 2]

Chemical Formula: $C_{25}H_{27}NaO_8$
Molecular Weight: 478.47

2-2: Structural Analysis of Sodium Lobarate

The structure of sodium lobarate was confirmed by comparing the NMR data thereof with the NMR data of lobaric acid. The NMR data of both compounds were measured using JEOL ECP-400 spectrometer (JEOL, Japan) after dissolving each sample in DMSO-$d_6$ solvent, and the chemical shift values ($\delta$C/$\delta$H=40.0/2.50 ppm) of the solvent DMSO-$d_6$ were used as reference points. For HMQC (1H-detected heteronuclear multiple-quantum coherence) analysis, 1JCH was set at 140 Hz, and for HMBC (heteronuclear multiple-bond coherence) analysis, nJCH was set at 8 Hz.

[Formula 8]

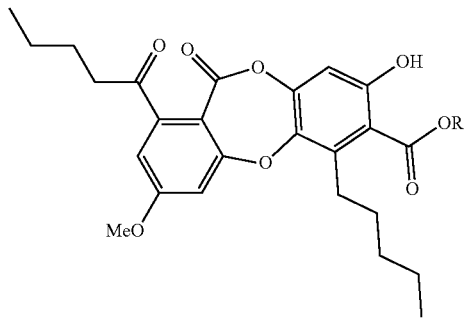

1: R = H
2: R = Na

1: lobaric acid, and 2: sodium lobarate

The NMR data of lobaric acid and sodium lobarate are shown in Table 4 below.

TABLE 4

The NMR data of lobaric acid and sodium lobarate

| position | Lobaric acid (1) | | Sodium lobarate (2) | |
| --- | --- | --- | --- | --- |
| | $\delta_C$ | $\delta_H$, mult.(J in Hz) | $\delta_C$ | $\delta_H$, mult.(J in Hz) |
| 1 | | | | |
| 2 | 112.0 | — | 112.1 | — |
| 3 | 163.2 | — | 163.7 | — |
| 4 | 106.6 | 6.99, d(2.2) | 106.5 | 6.90, d(2.2) |
| 5 | 111.5 | 7.11, d(2.2) | 111.6 | 7.05, d(2.2) |
| 6 | 141.1 | — | 139.4 | — |
| 7 | 162.5 | — | 163.1 | — |
| 8 | 203.6 | — | 203.7 | — |
| 9 | 41.5 | 2.86, t(7.3) | 41.6, | 2.83, t(7.0) |
| 10 | 25.9 | 1.48-1.57, m | 25.9 | 1.48-1.59, m |
| 11 | 22.4 | 1.28-1.36 m | 22.7 | 1.25-1.37, m |
| 12 | 14.3 | 0.89, t(6.9) | 14.3 | 0.882, t(6.9) |
| 1' | 120.9 | — | 116.1 | — |
| 2' | 153.1 | — | 163.7 | — |
| 3' | 106.3 | 6.70, s | 105.9 | 6.42, s |
| 4' | 149.0 | — | 148.9 | — |
| 5' | 144.7 | — | 145.4 | — |
| 6' | 134.4 | — | 139.3 | — |
| 7' | 168.6 | — | 170.1 | — |
| 8' | 27.7 | 2.79, m | 26.7 | 3.38, m |
| 9' | 30.8 | 1.47-1.54, m | 31.5 | 1.39-1.46, m |
| 10' | 31.7 | 1.34-1.43, m | 32.4 | 1.39-1.46, m |
| 11' | 21.9 | 1.28-1.36, m | 22.0 | 1.25-1.37, m |
| 12' | 14.3 | 0.88. t(6.9) | 14.5 | 0.878, t(6.9) |
| 4-OCH$_3$ | 57.0 | 3.90, s | 56.9 | 3.89, s |

As can be seen in Table 4 above, the change in chemical shift value resulting from the change of a functional group at C-7' from carboxylic acid to carboxylate anion, and the change in chemical shift values of the surrounding carbon atoms were observed. This shift is evidently useful for the structure identification of compound 2 (sodium lobarate). FIGS. 2 to 5 show the $^1$H NMR spectrum, (400 MHz, DMSO-$d_6$), $^{13}$C NMR spectrum (100 MHz, DMSO-$d_6$), HMQC data (400 MHz, DMSO-$d_6$) and HMBC data (400 MHz, DMSO-$d_6$) of sodium lobarate, respectively.

Example 3

Analysis of PTP-1b Inhibitory Activity of Sodium Lobarate

In order to analyze the PTP-1b (protein tyrosine phosphatase-1b) inhibitory activity of sodium lobarate, the activity of the enzyme was spectroscopically measured.

Specifically, to 0.5 mg/Ml of PTP-1b (Bioneer, Korea) in PTP-1b buffer (20 mM Tris-HCl, pH 8.0, 0.75 mM NaCl, 0.5 mM EDTA, 5 mM β-mercaptoethanol, 50% glycerol), 0, 1, 3, 10, 30, 100, 300, 1,000 and 3,000 nM of sodium lobarate and the substrate [pTyr1146] insulin receptor (1142-1153, Sigma, USA) were added. Each mixture was allowed to react at room temperature for 10-30 minutes, and malachite green-molybdate dye solution was added thereto and reacted at room temperature for 10 minutes. After completion between PTP-1b, sodium lobarate and the substrate, the absorbance at 620 nm was measured.

Figure 6:
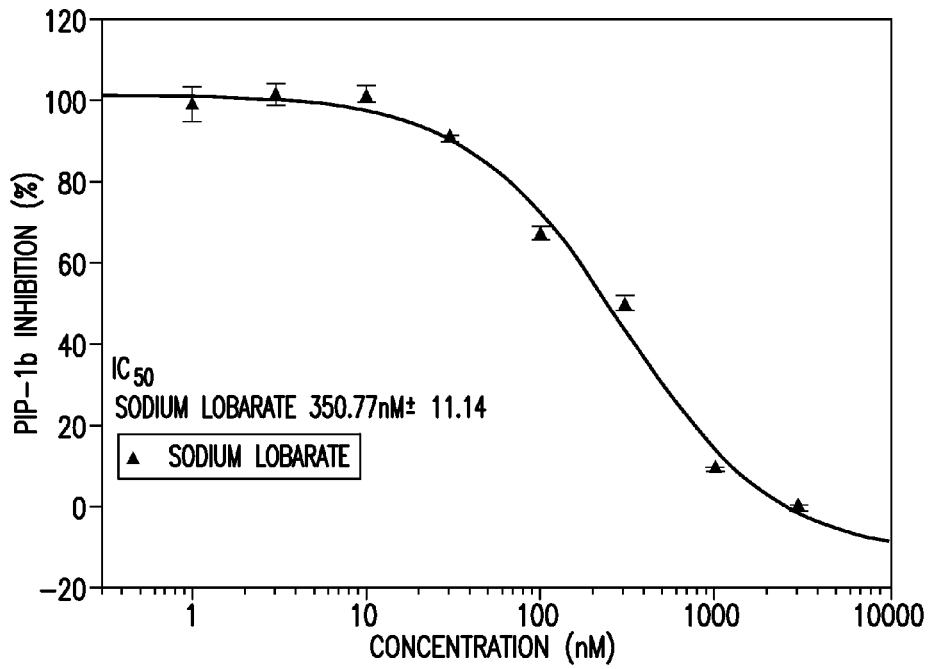
FIG. 6 is a graph showing the PTP-1b inhibitory activity of sodium lobarate.

As a result, as can be seen in FIG. 6, when the inhibitory activity of sodium lobarate against PTP-1b was analyzed, sodium lobarate showed an IC$_{50}$ of 350 nM, suggesting that it has excellent PTP-1b inhibitory effect. In addition, the inhibition (%) of PTP-1b increased as increasing the concentration of sodium lobarate.

Meanwhile, the PTP-1b inhibitory activity of lobaric acid as a control was measured. PTP-1b used in the test was purchased from BIOMOL (USA). In order to spectroscopically measure the activity of the enzyme, about 0.2 μg/Ml of PTP-1b, PTP-1b buffer (50 mM citrate, pH 6.0, 0.1M NaCl, 1 mM EDTA, 1 mM DTT), lobaric acid, 4 mM pNPP were mixed, shaken lightly, and then reacted at 37° C. for 30 minutes, after which the absorbance at 405 nm was measured. As a result, it was found that lobaric acid showed an IC$_{50}$ of 0.87 μM (870 nM).

Thus, it was confirmed that sodium lobarate according to the present invention has excellent PTP-1b inhibitory effects compared to lobaric acid and that this sodium lobarate is a pharmaceutical compound capable of preventing or treating diabetes and obesity.

Example 4

Analysis of Selectivity of Sodium Lobarate for Protein Tyrosine Phosphatases

In order to examine the selectivity of sodium lobarate for protein tyrosine phosphatases, the inhibitory activities of sodium lobarate against PTP-1b, PTPN2, PTPN5, PTPN6, PTPN7 and PTPN13 were examined by spectroscopically measuring the activities of the enzymes.

Specifically, to 0.5 mg/Ml of PTP-1b, PTPN2, PTPN5, PTPN6, PTPN7 or PTPN13 (Bioneer, Korea) in protein tyrosine phosphatase buffer (20 mM Tris-Hcl, pH 8.0, 0.75 mM NaCl, 0.5 mM EDTA, 5 mM β-mercaptoethanol, 50% glycerol), 0, 50, 100 or 200 nM sodium lobarate and the substrate [pTyr1146] insulin receptor (1142-1153, Sigma, USA) were added. Then, each of the mixtures was allowed to react at room temperature for 10-30 minutes, and then malachite green-molybdate dye solution (Sigma, USA) was added thereto and reacted at room temperature for 10 minutes. After completion of the reaction with the substrate, the absorbance at 620 nm was measured.

Figure 7:
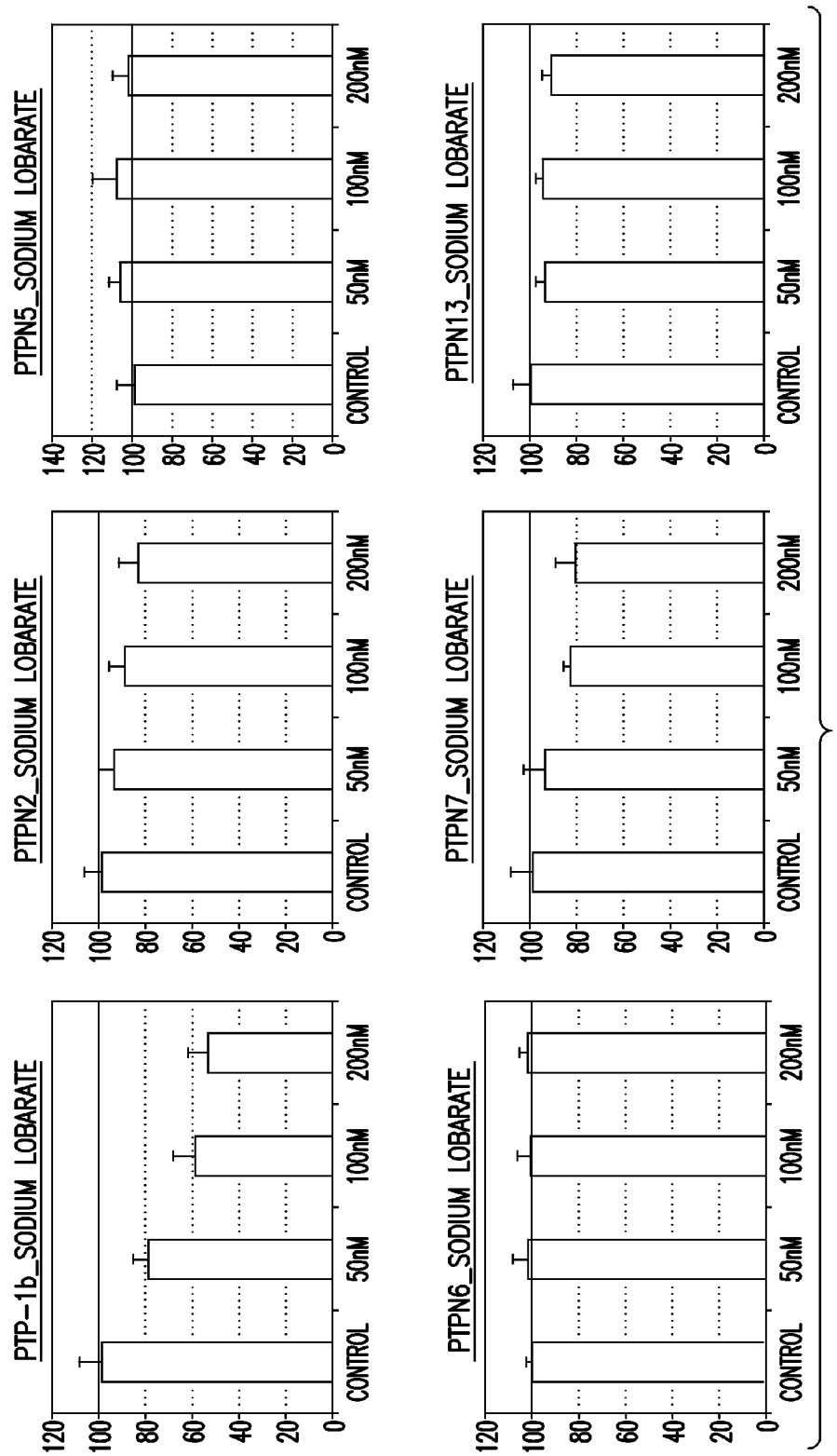
FIG. 7 is a set of graphs showing inhibitory activities against PTP-1b, PTPN2, PTPN5, PTPN6, PTPN7 and PTPN13, determined by measuring absorbance at 620 nm.

The selectivity of sodium lobarate for protein tyrosine phosphatases was examined as described above. As a result, as can be seen in FIG. 7, sodium lobarate showed an inhibition rate of 50.0% against PTP-1b at a concentration of 200 uM (IC$_{50}$), whereas it showed an inhibition rate of 83.7% against TC-PTP (PTPN2), protein tyrosine phosphatases, known to be most similar to PTP-1b.

It is known that the protein tyrosine phosphatases, TC-PTP (PTPN2) is most similar to PTP-1b in terms of the amino acid sequence and the 3D structure, induces embryonic lethality, has enzymatic characteristics and active site (containing the second aryl-phosphate binding site similar to those of PTP-1b. Although 757 compounds targeting PTP-1b were registered, the PTP-1b targeting compound that entered the clinical phase has not been reported, and plant extracts that target various enzymes, including PTP-1b, are only being marketed or in the clinical trial phase.

Accordingly, the above test results indicate that the compound sodium lobarate according to the present invention acts selectively only on PTP-1b among protein tyrosine phosphatases and that sodium lobarate is a PTP-1b inhibitor which can be used to treat diabetes.

Example 5

Verification of Effects of Sodium Lobrate on Disease Model Animals 5-1: Observation of Change in Blood Glucose Level after Intraperitoneal Administration of Sodium Lobarate Based on pre-tests, effectiveness tests and toxicity tests for sodium lobarate, dose (expressed as test compound amount (mg)/test animal's weight (kg)) was determined. To 7-week-old male db/db mice (type 2 diabetic model animals, C57/BLKS/J-db/db, the Korea Research Institute of Bioscience and Biotechnology), 200 µl of PBS for a control group and 10 mg/kg of sodium lobarate (PTP-1b activity inhibitory compound) for a test group was administered, respectively, intraperitoneally daily, and the blood glucose levels of the animals were measured twice a week.

Figure 8:
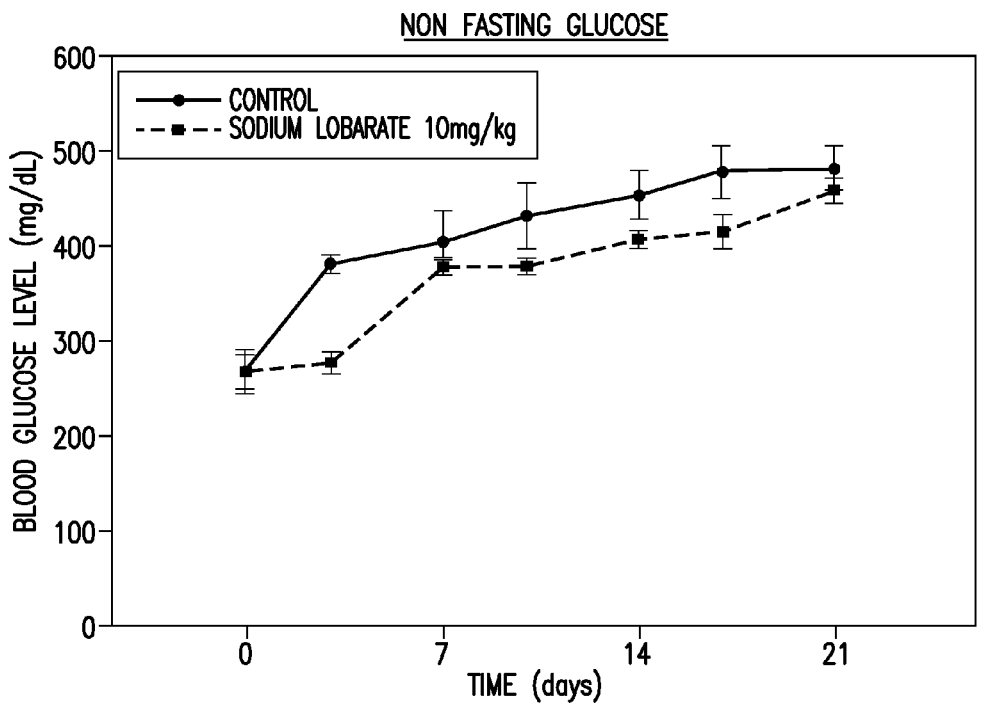
FIG. 8 is a graphic diagram showing the results of measuring the change in blood glucose levels after intraperitoneal administration of sodium lobarate.

Specifically, sodium lobarate (PTP-1b activity inhibitory compound) was administered by intraperitoneal injection to 7-week-old male db/db mice (type 2 diabetic model animals, C57/BLKS/J-db/db, the Korea Research Institute of Bioscience and Biotechnology), and the change in the blood glucose level of the animals was measured. As a result, it was found that the average blood glucose level was 267 mg/dL at day 0, 276 mg/dL at day 3, 378 mg/dL at day 7, 378 mg/dL at day 10, 407 mg/dL at day 14, 415 mg/dL at day 17, and 459 mg/dL at day 21 in the test group (n=6) administered with 10 mg/kg, as can be seen in FIG. 8, and that the increase in the blood glucose level was less than that in the control group.

5-2: Observation of Change in Blood Glucose Level Following 6 Hours of Fasting after Intraperitoneal Administration of Sodium Lobrate In order to more accurately measure the anti-diabetic effect of sodium lobarate, 200 µl of PBS for a control group and 10 mg/kg of sodium lobarate (PTP-1b activity inhibitory compound) for a test group was administered, respectively, intraperitoneally daily to 7-week-old male db/db mice (type 2 diabetic model animals, C57/BLKS/J-db/db, the Korea Research Institute of Bioscience and Biotechnology), and the blood glucose levels of the animals were measured twice a week. Herein, measurement of the blood glucose level was performed after 6 hours of fasting after intraperitoneal injection of sodium lobarate.

Figure 9:
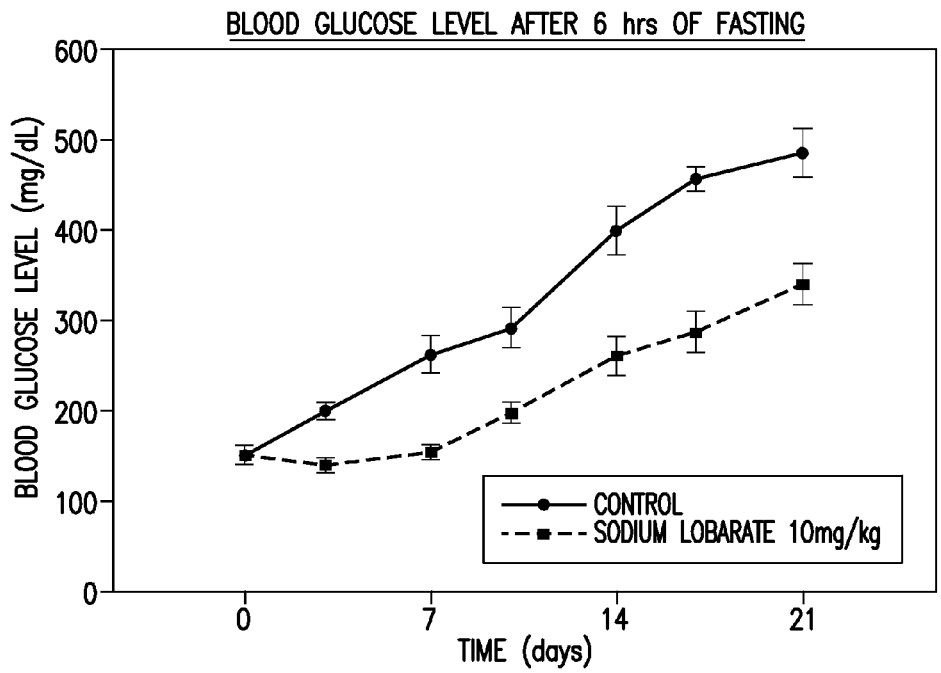
FIG. 9 is a graphic diagram showing the results of measuring the blood glucose level following 6 hours of fasting after intraperitoneal administration of sodium lobarate.

As a result, it was found that the average blood glucose level was 141 mg/dL at day 0, 142 mg/dL at day 3, 185 mg/dL at day 7, 206 mg/dL at day 10, 232 mg/dL at day 14, 236 mg/dL at day 17, and 313 mg/dL at day 21 in the test group (n=6) injected intraperitoneally with 10 mg/kg of sodium lobarate, as can be seen in FIG. 9 and that the increase in the blood glucose level was less than that in the control group, as Example 5-1.

5-3: Intraperitoneal Glucose Tolerance Test (IPGTT) 28 Days after Intraperitoneal Administration of Sodium Lobarate An intraperitoneal glucose tolerance test (IPGTT) in the animal model of sodium lobarate was performed in the following manner.

To 7-week-old male db/db mice (type 2 diabetic model animals, C57/BLKS/J-db/db, the Korea Research Institute of Bioscience and Biotechnology), physiological saline for a control group and 10 mg/kg of sodium lobarate for a test group was injected, respectively, intraperitoneally every day for 28 days. Then, the animals were fasted for 16 hours without administering physiological saline or sodium lobarate, after which glucose (500 mg/Ml; injection volume of 200 µl) was injected intraperitoneally into the animals. 0, 15, 30, 60, 90 and 120 min after injection of glucose, blood was sampled from the tail vein, and the changes in the blood glucose levels of the samples were measured.

Figure 10:
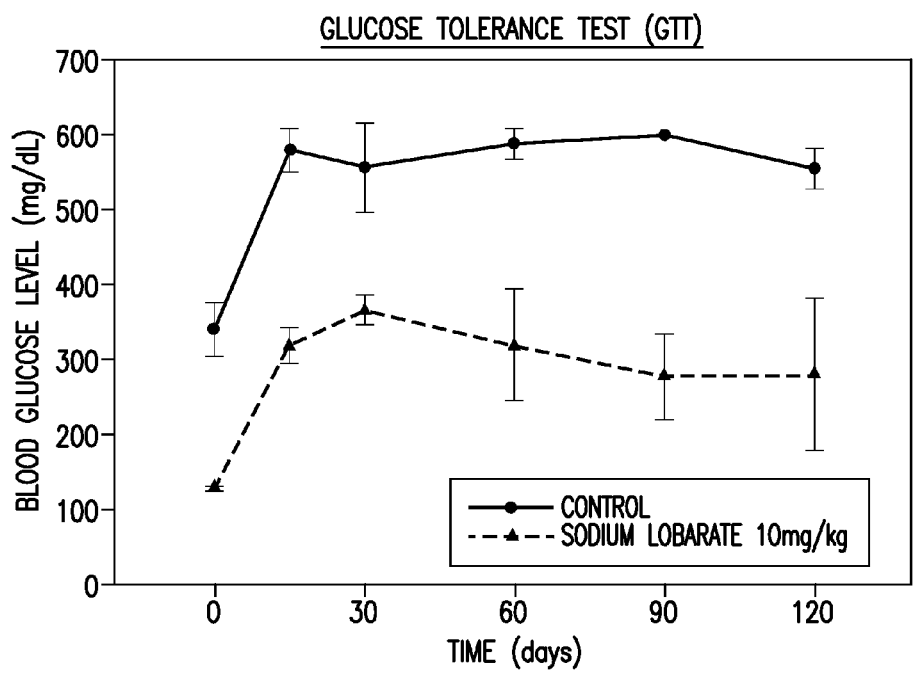
FIG. 10 is a graphic diagram showing the results of measuring the change in the blood glucose level 28 days after intraperitoneal administration of sodium lobarate.

As described above, the changes in glucose tolerance resulting from intraperitoneal injection of glucose into the type 2 diabetic model animals were measured. As a result, it was found that the blood glucose level after injection of glucose was 341 mg/dL at 0 min, 579 mg/dL at 15 min, 557 mg/dL at 30 min, 589 mg/dL at 60 min, 600 mg/dL at 90 min, and 555 mg/dL at 120 min and that the increase in the blood glucose level was very rapid and the decrease in the blood glucose level was very slow in the control group (injected with physiological saline), as can be seen in FIG. 10. On the other hand, in the test group administered intraperitoneally with 10 mg/kg of sodium lobarate for 28 days, the blood glucose level after injection of glucose was 153 mg/dL at 0 min, 291 mg/dL at 15 min, 361 mg/dL at 30 min, 385 mg/dL at 60 min, 335 mg/dL at 90 min, and 290 mg/dL at 120 min, and thus a low increase and a fast decrease in the blood glucose level were observed, suggesting that the blood glucose level was returned to normal.

The results of Examples 5-1 to 5-3 indicate that sodium lobarate according to the present invention has a very excellent anti-diabetic effect.

Example 6

Preparation of Novel Compound Lobarin from Lobaric Acid 50 mg of the lobaric acid obtained in Example 1-2 was dissolved in 5 mL of acetone, and 1 ml of 0.5 N NaOH was added thereto. The mixture was stirred to react at room temperature for 5 minutes, and 0.5 mL of 1N HCl solution was added to the mixture to stop the reaction. The reaction mixture was concentrated and partitioned between methylene chloride and an aqueous solution (pH=2), and the methylene chloride layer was collected and concentrated, thereby obtaining 50 mg of a novel compound of the following Formula 4. The obtained compound was named "Lobarin."

[Formula 4]

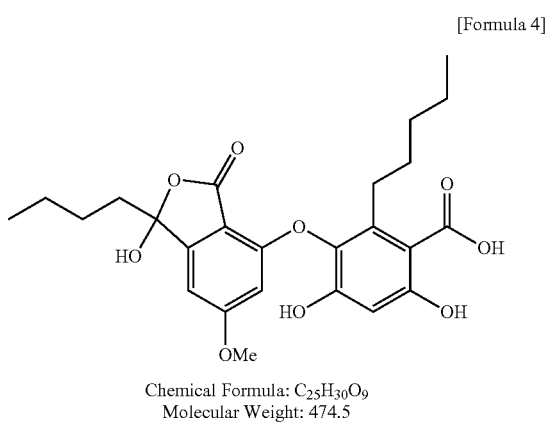 [SMILES: CCCCCc1c(Oc2cc(OC)cc3c2C(=O)OC3(O)CCCC)c(O)cc(O)c1C(=O)O]

Chemical Formula: $C_{25}H_{30}O_9$
Molecular Weight: 474.5

Figure 11:
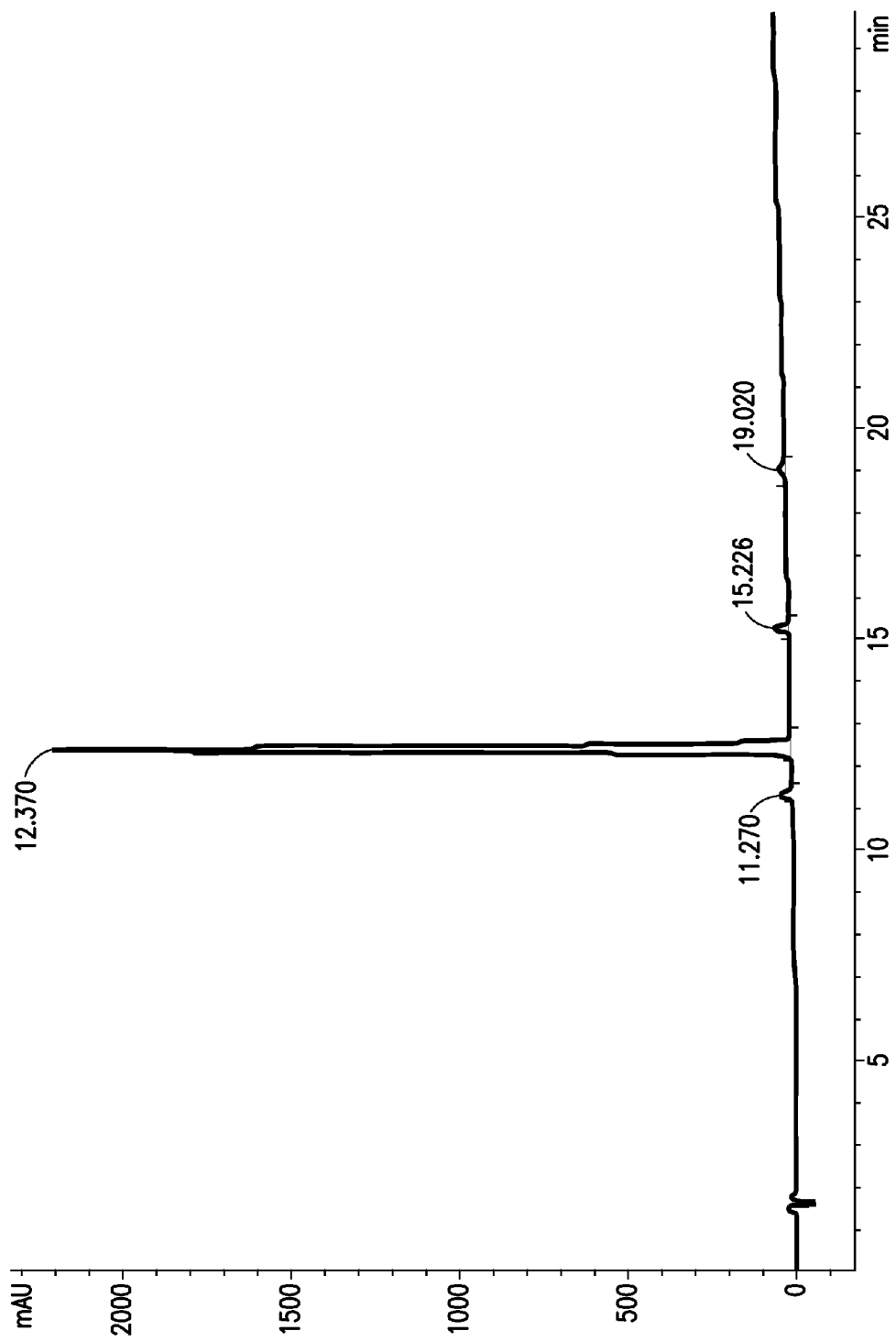
FIG. 11 shows the results of HPLC analysis conducted to examine the purity of Lobarin.

Meanwhile, in order to increase the purity of the obtained compound, the compound was analyzed by reverse phase HPLC using Agilent Eclipse XDB-C18 column (4.6×150 mm, USA). The solvent system used in the analysis was composed of line A and line B which supplied 0.1% formic acid-containing water and 0.1% formic acid-containing acetonitrile, respectively. The elution conditions were as follows: 40% to 50% acetonitrile for 5 min; 50% to 80% acetonitrile for 15 min; and 80% to 90% acetonitrile for 10 min. The final purity was 96.1% (see FIG. 11).

Example 7

Structural Analysis of Novel Compound Lobarin

The molecular structure of Lobarin synthesized in Example 6 was analyzed by high-resolution electrospray ionization mass spectrometry (HRESIMS) and NMR spectrometry.

Figure 12:
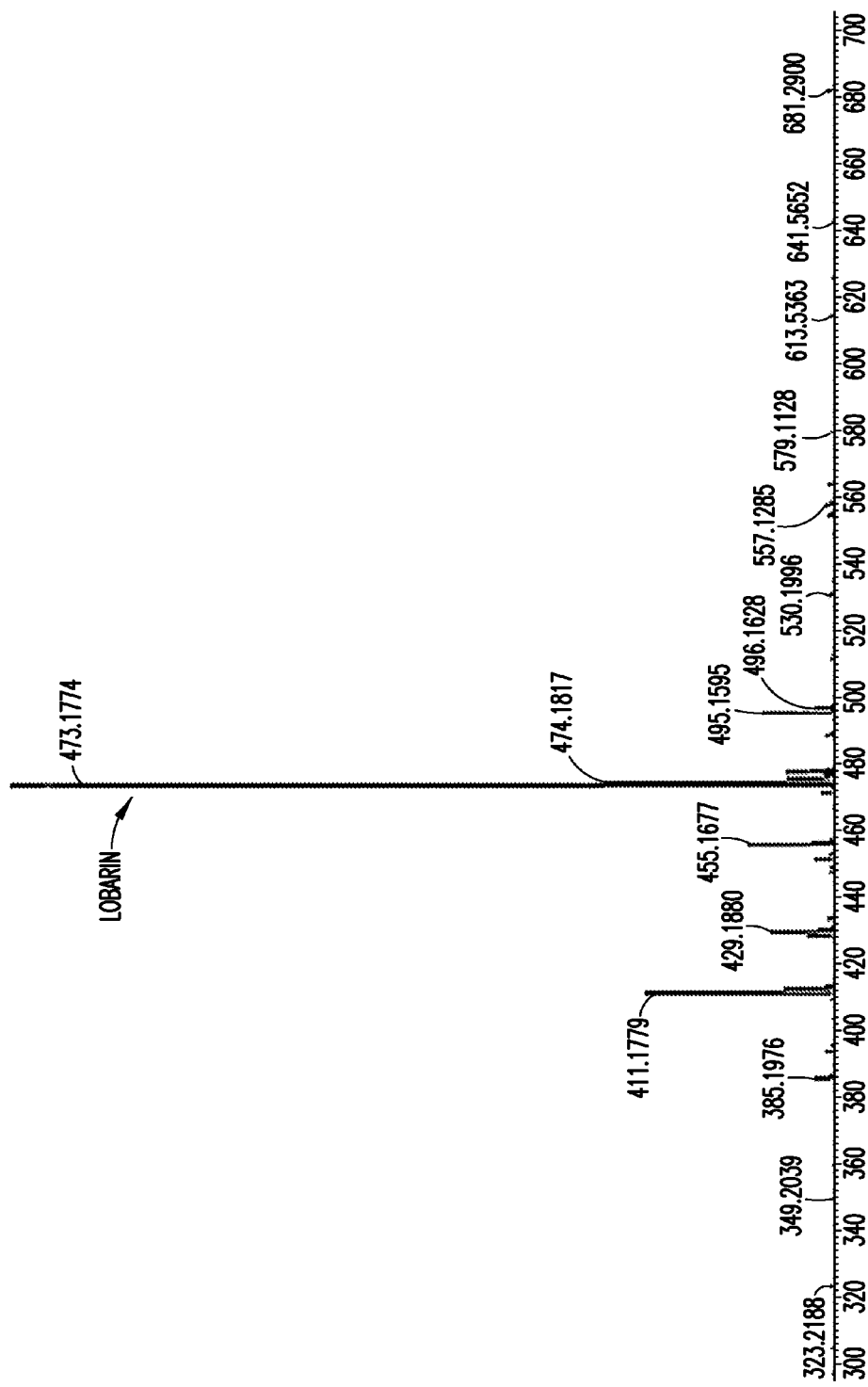
FIG. 12 shows the results of HRESIMS analysis of Lobarin.

The analysis of anions by HRESIMS was carried out using Q-TOF micro LC-MS/MS instrument (Waters, USA). As can be seen in FIG. 12, Lobarin showed a molecular ion peak of m/z 473.1774, suggesting that Lobarin has a molecular formula of $C_{25}H_{30}O_9$.

The NMR spectra of Lobarin were measured using JEOL ECP-400 spectrometer (JEOL, Japan) after dissolving Lobarin in DMSO-$d_6$ solvent, and the chemical shift values ($\delta C/\delta H$=40.0/2.50 ppm) of the solvent DMSO-$d_6$ were used as reference points. For HMQC (1H-detected heteronuclear multiple-quantum coherence) measurement, 1JCH was set at 140 Hz, and for HMBC (heteronuclear multiple-bond coherence) measurement, nJCH was set at 8 Hz. The mass spectroscopic analysis of Lobarin was performed using Q-TOF micro LC-MS/MS.

Figure 13A:
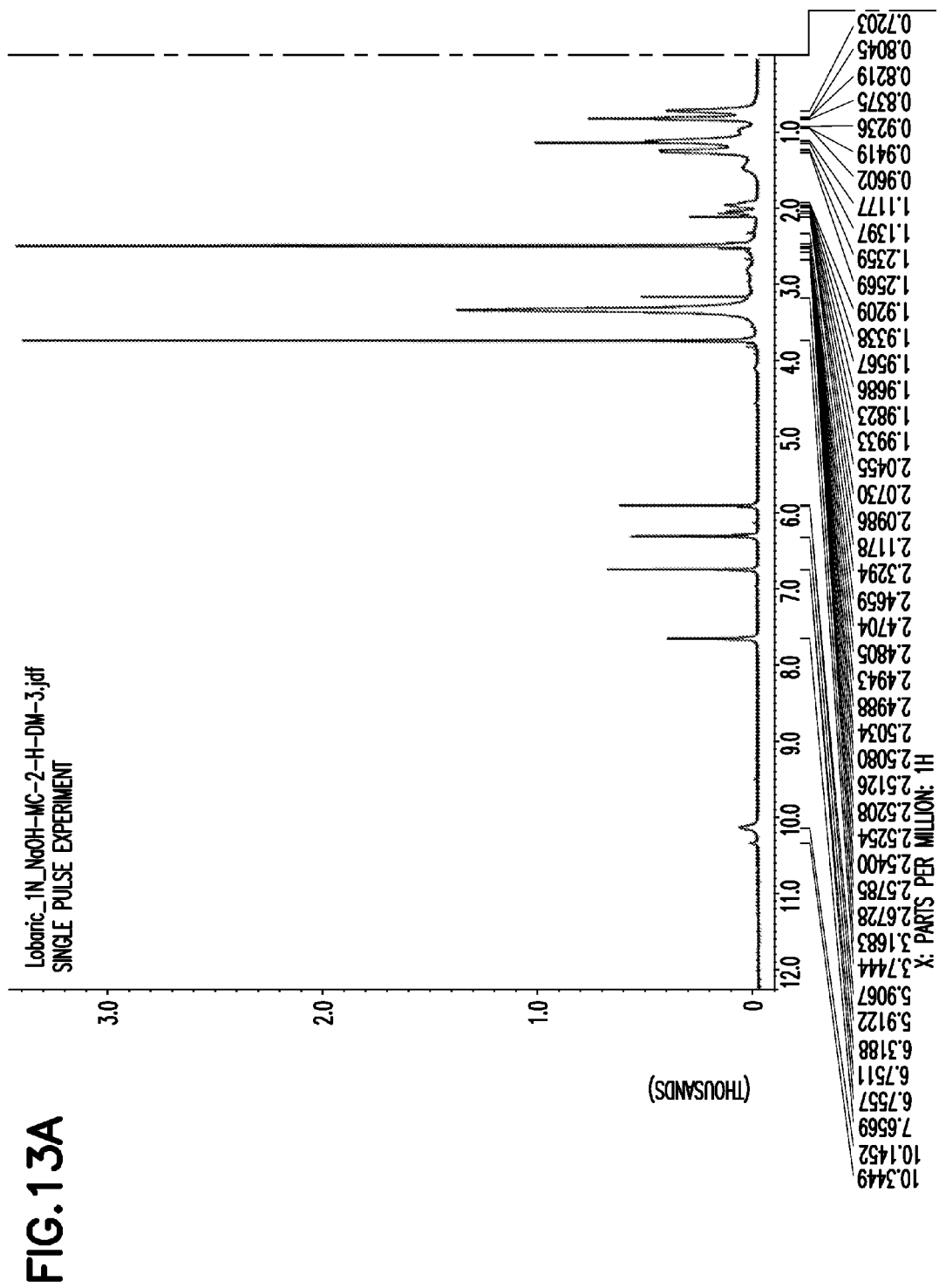
FIG. 13 shows the $^1$H NMR spectrum (400 MHz, DMSO-$d_6$) of Lobarin.
Figure 14A:
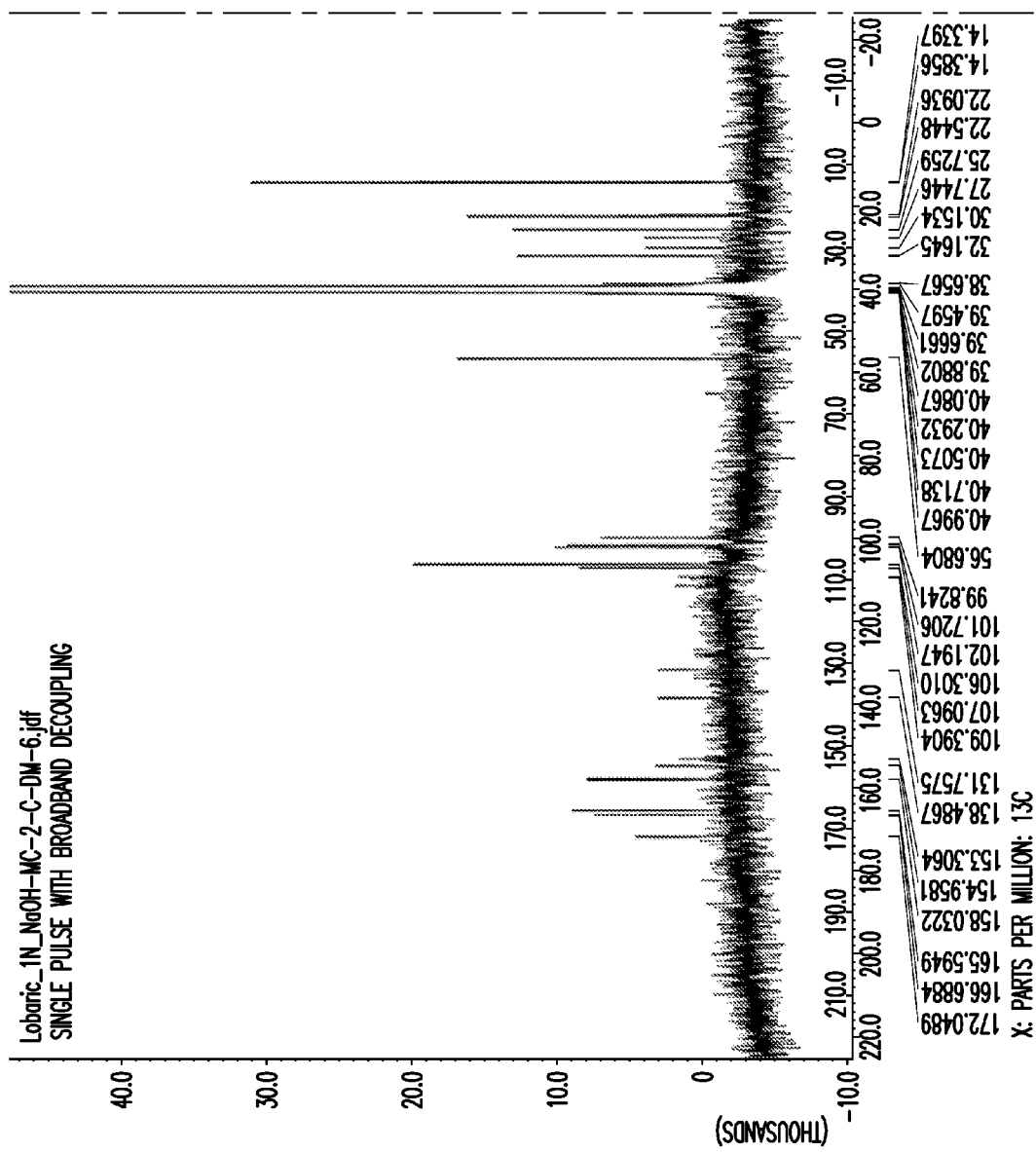
FIG. 14 shows the $^{13}$C NMR spectrum (400 MHz, DMSO-$d_6$) of Lobarin.

As can be seen in the $^1H$ NMR and $^{13}C$ NMR spectra in FIGS. 13 and 14, respectively, the $^1H$ NMR and $^{13}C$ NMR spectra of Lobarin showed patterns very similar to those of lobaric acid. Thus, Lobarin can be supposed to be a compound produced by hydrolysis of lobaric acid considering the fact that the structure of Lobarin was very similar to that of lobaric acid and the difference in molecular weight therebetween was 18 Da. When the NMR data of Lobarin were compared with the NMR data of lobaric acid, the $^{13}C$ peak corresponding to a ketone functional group, observed in the $^{13}C$ NMR spectrum of lobaric acid, disappeared. Instead, the $^{13}C$ peak was observed at 106.3 ppm in the $^{13}C$ NMR spectrum of Lobarin, and a peak (7.65 ppm) corresponding to the proton of an OH functional group was observed in the $^1H$ NMR spectrum of Lobarin. Based on these differences in the NMR data, it is believed that the ketone functional group in lobaric acid as shown in Formula 7 was changed into an oxygen anion by nucleophilic attack of a hydroxyl group, and sequentially adjacent ester groups were degraded by nucleophilic addition, and as a result, the structure of Lobarin was produced. The predicted structure of Lobarin was confirmed by HMQC analysis and HMBC analysis, which are two-dimensional NMR spectrometry methods (see Table 5).

Figure 15A:
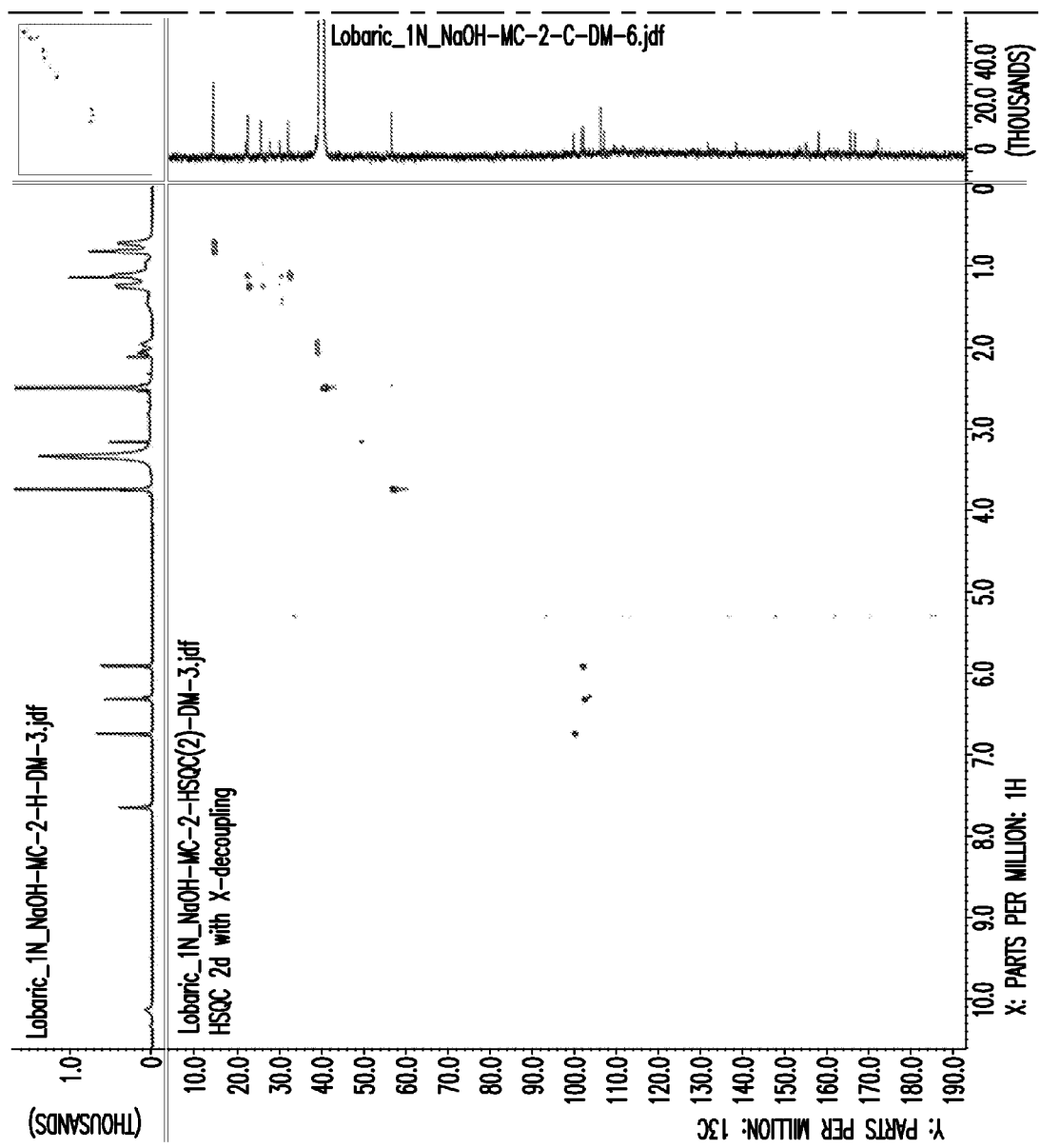
FIG. 15 shows HSQC data (400 MHz, DMSO-$d_6$) for Lobarin.
Figure 16A:
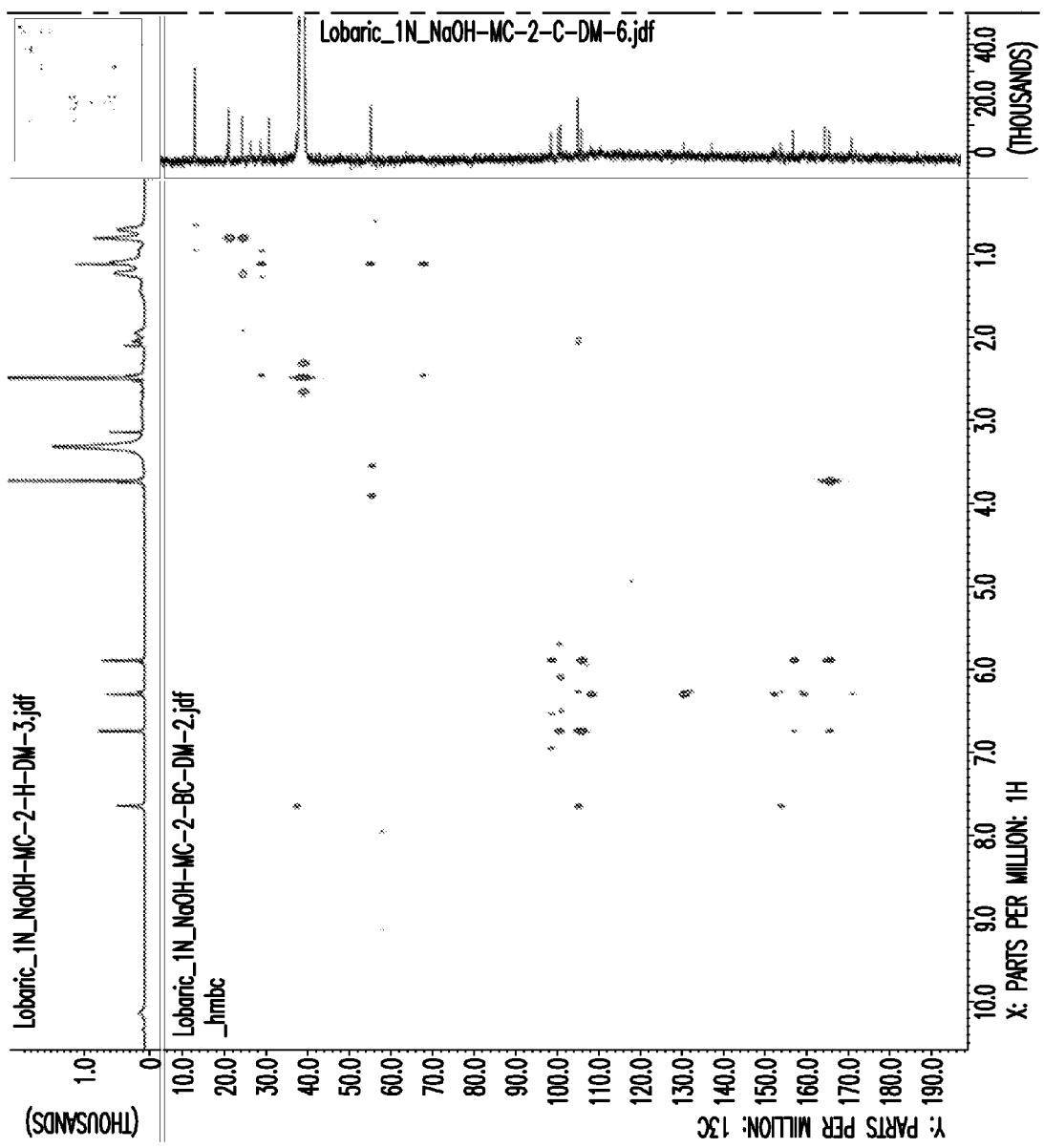
FIG. 16 shows HMBC data (400 MHz, DMSO-$d_6$) for Lobarin.

The positions corresponding to every carbon and hydrogen of Lobarin were identified by analysis of the HMQC data (see FIG. 15) and the HMBC data (see FIG. 16), and such data were similar to the NMR data of lobaric acid. In addition, the HMBC correlations from the peak (7.65 ppm) corresponding to the proton of the OH functional group to the $^{13}C$ NMR peaks corresponding to the C-6, C-7 and C-8 positions provided important information to identify the suggested structure of Lobarin.

TABLE 5

NMR data for Lobarin (400 MHz, DMSO-$d_6$)

| Position | $\delta_C$ | $\delta_H$, mult.(J in Hz) | HMBC[a] |
|---|---|---|---|
| 1 | 107.1 | — | — |
| 2 | 158.0 | — | — |
| 3 | 101.7 | 5.91, d(1.8) | 1, 2, 4, 5 |
| 4 | 166.8 | — | — |
| 5 | 99.8 | 6.75, d(1.8) | 3, 1, 4, 5 |
| 6 | 155.0 | — | — |
| 7 | 165.6 | — | — |
| 8 | 106.3 | — | — |
| 9 | 38.7 | 1.97, m | 8 |
|  |  | 2.07, m |  |
| 10 | 25.7 | 1.14, m | — |
|  |  | 1.25, m |  |
| 11 | 22.5 | 1.12, m | — |
|  |  | 1.38, m |  |
| 12 | 14.3 | 0.82, br t | 10.11 |
| 1' | 109.4 | — | — |
| 2' | 153.3 | — | — |
| 3' | 102.2 | 6.32, s | 1', 5', 2', 4', 7' |
| 4' | 160.7 | — | — |
| 5' | 131.8 | — | — |
| 6' | 138.5 | — | — |
| 7' | 172.0 | — | — |
| 8' | 27.7 | 2,78, m | — |
| 9' | 30.2 | 1.14, m | — |
|  |  | 2.24, m |  |
| 10' | 32.2 | 1.11, m | — |
|  |  | 1.29, m |  |
| 11' | 22.1 | 1.23, m | — |
|  |  | 1.27, m |  |
| 12' | 14.4 | 0.72, br s | — |
| 4-OCH$_3$ | 56.7 | 3.74, s | 4 |
| 8-OH | — | 7.66, s | 9, 8, 6 |

[a]HMBC correlations, optimized for 8 Hz, are from proton(s) stated to the indicated carbon (s).

Example 8

Analysis of PTP-1b Inhibitory Activity of Lobarin

The activity of the enzyme was spectroscopically measured to analyze the protein PTP-1b inhibitory activity of Lobarin.

Specifically, to 0.5 mg/Ml of PTP-1b (Bioneer, Korea) in PTP-1b buffer (20 mM Tris-HCL, pH 8.0, 0.75 mM NaCl, 0.5 mM EDTA, 5 mM β-mercaptoethanol, 50% glycerol), 0, 1, 3, 10, 30, 100, 300, 1000 or 3000 nM Lobarin and the substrate [pTyr1146] insulin receptor (1142-1153, Sigma, USA) were added. Each of the mixtures was allowed to react at room temperature for 10-30 minutes, and malachite green-molybdate dye solution was added thereto and reacted at room temperature for 10 minutes. After completion between PTP-1b, Lobarin and the substrate, the absorbance at 620 nm was measured.

Figure 17:
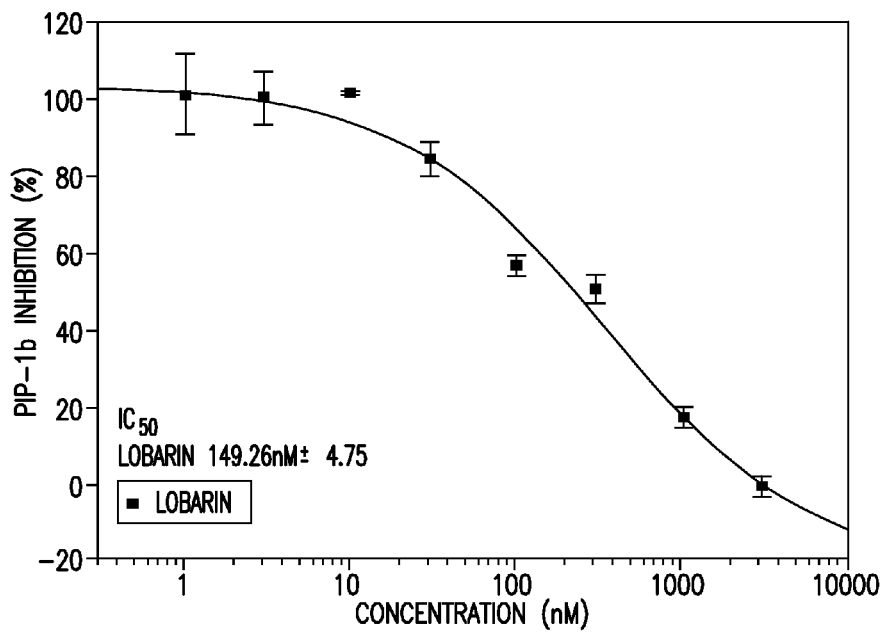
FIG. 17 is a graph showing PTP-1b inhibitory activity for Lobarin.

The inhibitory activity of Lobarin against PTP-1b was analyzed as described above. As a result, Lobarin showed an $IC_{50}$ of 149 nM as can be seen in FIG. 17, suggesting that it has excellent PTP-1b inhibitory effect. In addition, the inhibition (%) of PTP-1b increased as increasing the concentration of Lobarin. Thus, it was confirmed that Lobarin is a pharmaceutical compound capable of preventing or treating diabetes and obesity.

Example 9

Analysis of Selectivity of Lobarin for Protein Tyrosine Phosphatases

In order to examine the selectivity of Lobarin for protein tyrosine phosphatases, the inhibitory activities of Lobarin against PTP-1b, PTPN2, PTPN5, PTPN6, PTPN7 and PTPN13 were examined by spectroscopically measuring the activities of the enzymes.

Specifically, to 0.5 mg/Ml of PTP-1b, PTPN2, PTPN5, PTPN6, PTPN7 or PTPN13 (Bioneer, Korea) in protein tyrosine phosphatase buffer (20 mM Tris-Hcl, pH 8.0, 0.75 mM NaCl, 0.5 mM EDTA, 5 mM β-mercaptoethanol, 50% glycerol), 0, 50, 100 or 200 nM Lobarin and the substrate [pTyr1146] insulin receptor (1142-1153, Sigma, USA) were added. Then, each of the mixtures was allowed to react at room temperature for 10-30 minutes, and then malachite green-molybdate dye solution (Sigma, USA) was added thereto and reacted at room temperature for 10 minutes. After completion of the reaction with the substrate, the absorbance at 620 nm was measured.

Figure 18:
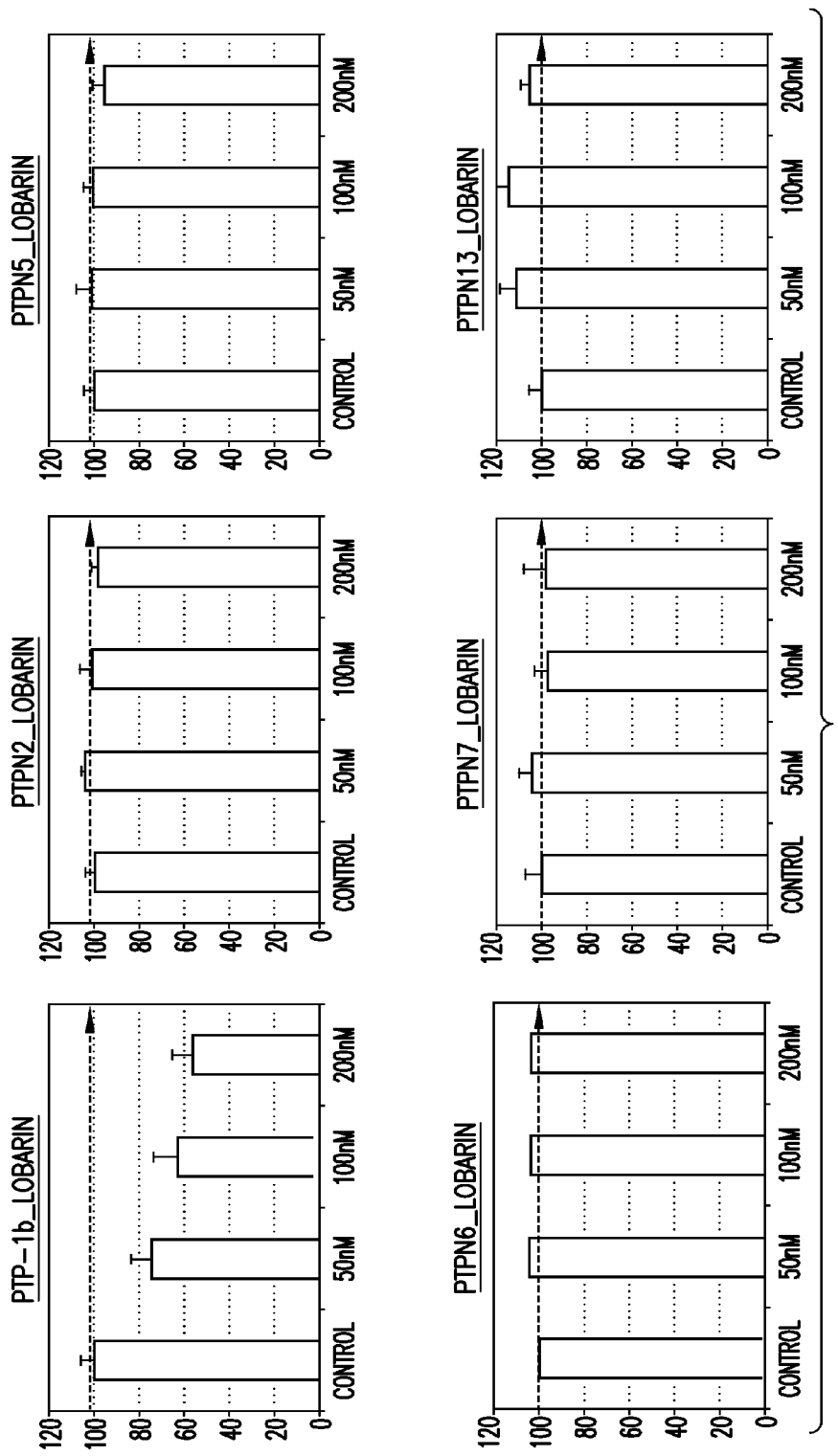
FIG. 18 is a set of graphs showing the inhibitory activities of Lobarin against PTP-1b, PTPN2, PTPN5, PTPN6, PTPN7 and PTPN13, determined by measuring absorbance at 620 nm.

The selectivity of Lobarin for protein tyrosine phosphatases was examined as described above. As a result, Lobarin showed an inhibition rate of 52.2% against PTP-1b at a concentration of 200 uM ($IC_{50}$), and particularly, Lobarin had no inhibitory activity against other protein tyrosine phosphatases, including TC-PTP (PTPN2), as can be seen in FIG. 18.

Accordingly, the above test results indicate that the compound Lobarin according to the present invention acts selectively only on PTP-1b among protein tyrosine phosphatases and that Lobarin is a PTP-1b inhibitor which can be used to treat diabetes.

Example 10

Verification of Effects of Lobarin on Disease Model Animals 10-1: Observation of Change in Blood Glucose Level after Intraperitoneal Administration of Lobarin Based on pre-tests, effectiveness tests and toxicity tests for Lobarin, dose (expressed as test compound amount (mg)/test animal's weight (kg)) was determined. To 7-week-old male db/db mice (type 2 diabetic model animals, C57/BLKS/J-db/db, the Korea Research Institute of Bioscience and Biotechnology), 200 µl of PBS for a control group and 10 mg/kg of Lobarin for a test group was administered, respectively, intraperitoneally daily, and the blood glucose levels of the animals were measured twice a week.

Figure 19:
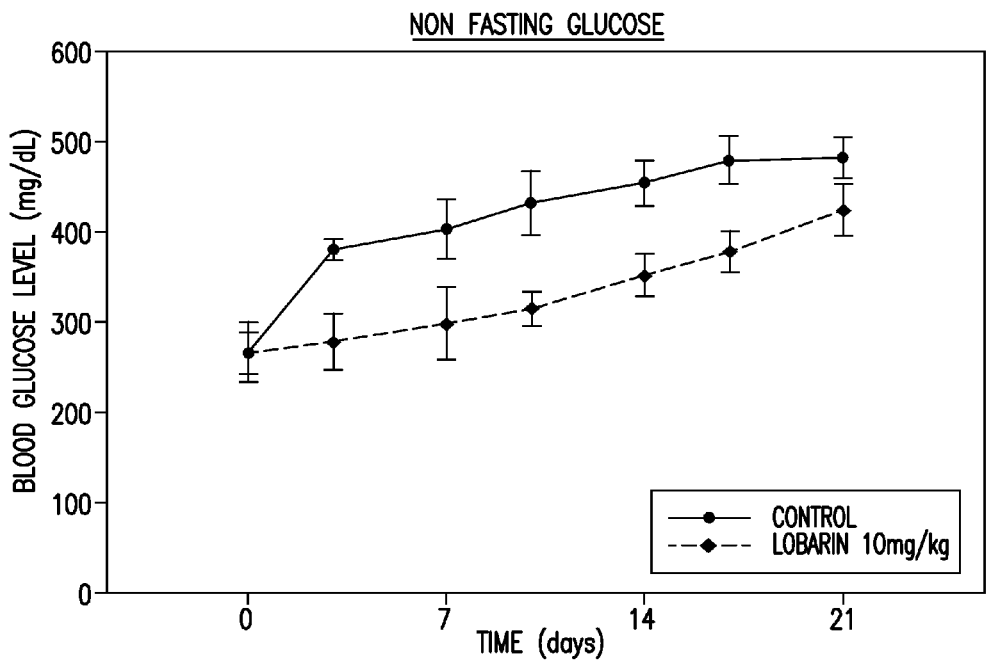
FIG. 19 is a graphic diagram showing the change in the blood glucose level after intraperitoneal administration of Lobarin.

Specifically, Lobarin was administered by intraperitoneal injection to 7-week-old male db/db mice (type 2 diabetic model animals, C57/BLKS/J-db/db, the Korea Research Institute of Bioscience and Biotechnology), and the change in blood glucose level of the animals was measured. As a result, it was found that the average blood glucose level was 268 mg/dL at day 0, 381 mg/dL at day 3, 404 mg/dL at day 7, 432 mg/dL at day 10, 454 mg/dL at day 14, 479 mg/dL at day 17, and 482 mg/dL at day 21 in the control group (n=6) indicating that the blood glucose level increased rapidly, and that, however, the average blood glucose level was 267 mg/dL at day 0, 278 mg/dL at day 3, 298 mg/dL at day 7, 315 mg/dL at day 10, 352 mg/dL at day 14, 379 mg/dL at day 17, and 425 mg/dL at day 21 in the test group (n=6) injected intraperitoneally with 10 mg/kg of Lobarin, and the increase in the blood glucose level was less than that in the control group as can be seen in FIG. 19.

10-2: Observation of Change in Blood Glucose Level Following 6 Hours of Fasting after Intraperitoneal Administration of Lobarin In order to more accurately measure the anti-diabetic effect of Lobarin, 200 µl of PBS for a control group and 10 mg/kg of Lobarin for a test group was administered, respectively, intraperitoneally daily to 7-week-old male db/db mice (type 2 diabetic model animals, C57/BLKS/J-db/db, the Korea Research Institute of Bioscience and Biotechnology), and the blood glucose levels of the animals were measured twice a week. Herein, measurement of the blood glucose levels was performed after 6 hours of fasting after intraperitoneal injection of Lobarin.

Figure 20:
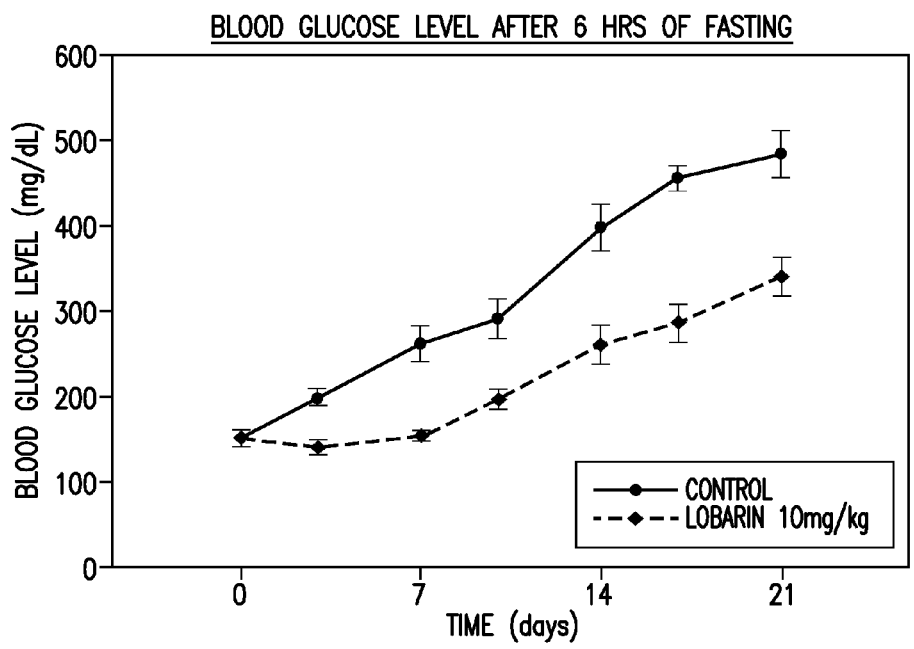
FIG. 20 is a graphic diagram showing the results of measuring the blood glucose level following 6 hours of fasting after intraperitoneal administration of Lobarin.

As a result, as can be seen in FIG. 20, it was found that the average blood glucose level was 151 mg/dL at day 0, 199 mg/dL at day 3, 262 mg/dL at day 7, 291 mg/dL at day 10, 397 mg/dL at day 14, 455 mg/dL at day 17, and 483 mg/dL at day 21 in the control group (n=6), indicating that the blood glucose level increased rapidly, and that, however, the average blood glucose level was 152 mg/dL at day 0, 141 mg/dL at day 3, 155 mg/dL at day 7, 198 mg/dL at day 10, 261 mg/dL at day 14, 287 mg/dL at day 17, and 340 mg/dL at day 21 in the test group (n=6) injected intraperitoneally with 10 mg/kg of Lobarin, and the increase in the blood glucose level was less than that in the control group, as Example 10-1.

10-3: Intraperitoneal Glucose Tolerance Test 28 Days after Intraperitoneal Administration of Lobarin An intraperitoneal glucose tolerance test (IPGTT) in the animal model of Lobarin was performed in the following manner.

To 7-week-old male db/db mice (type 2 diabetic model animals, C57/BLKS/J-db/db, the Korea Research Institute of Bioscience and Biotechnology), 20% DMSO for a control group and 10 mg/kg of Lobarin for a test group was injected, respectively, intraperitoneally every day for 28 days. Then, the animals were fasted for 16 hours without administering 20% DMSO or Lobarin for each group, after which glucose (500 mg/Ml; injection volume of 200 µl) was injected intraperitoneally into the animals. 0, 15, 30, 60, 90 and 120 min after injection of glucose, blood was sampled from the tail vein, and the changes in the blood glucose levels of the samples were measured.

Figure 21:
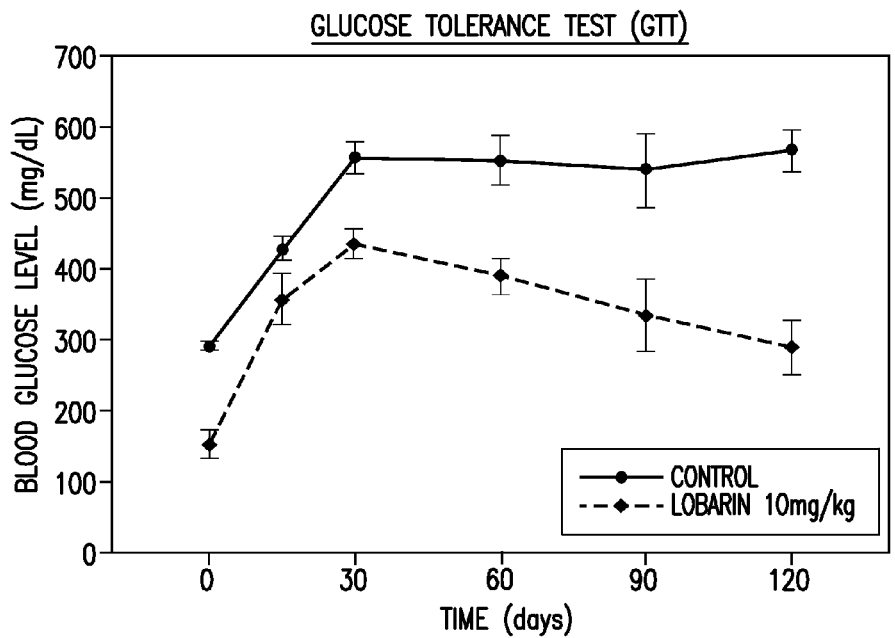
FIG. 21 is a graphic diagram showing the change in the blood glucose level 28 days after intraperitoneal administration of Lobarin.

As described above, the changes in glucose tolerance resulting from intraperitoneal injection of glucose into the type 2 diabetic model animals were measured. As a result, as can be seen in FIG. 21, the blood glucose level after injection of glucose was 293 mg/dL at 0 min, 429 mg/dL at 15 min, 557 mg/dL at 30 min, 553 mg/dL at 60 min, 539 mg/dL at 90 min, and 568 mg/dL at 120 min in the control group (injected intraperitoneally with 20% DMSO), and the increase in the blood glucose levels was very rapid and the decrease in the blood glucose levels was very slow. On the other hand, the blood glucose level after injection of glucose was 153 mg/dL at 0 min, 358 mg/dL at 15 min, 436 mg/dL at 30 min, 390 mg/dL at 60 min, 335 mg/dL at 90 min, and 290 mg/dL at 120 min in the test group administered intraperitoneally with 10 mg/kg of Lobarin which is a PTP-1b activity inhibitory compound, and thus a low increase and a fast decrease in the blood glucose level were observed, suggesting that the blood glucose level was returned to normal.

The results of Examples 10-1 to 10-3 indicate that the novel compound Lobarin according to the present invention has a very excellent anti-diabetic effect.

Example 11

Preparation of Novel Compound Lobarstin from Lobaric Acid 50 mg of the lobaric acid obtained in Example 1-2 was dissolved in 50 mL of acetone, and 50 mL of water was added thereto, followed by stiffing. 0.25 ml of 2 N NaOH was added to the mixture, which was then stirred to react at room temperature for 15 minutes, and 0.5 mL of 1N HCl solution was added to the mixture to stop the reaction. The reaction mixture was concentrated and partitioned between methylene chloride and an aqueous solution (pH=2), and the methylene chloride layer was collected and concentrated, thereby obtaining 50 mg of a novel compound of the following Formula 6. The obtained compound was named "Lobarstin".

[Formula 6]

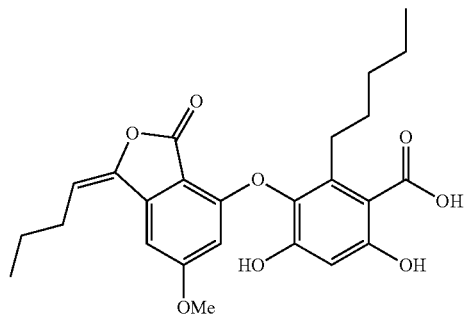

Chemical Formula: $C_{25}H_{28}O_8$
Molecular Weight: 456.49

Figure 22:
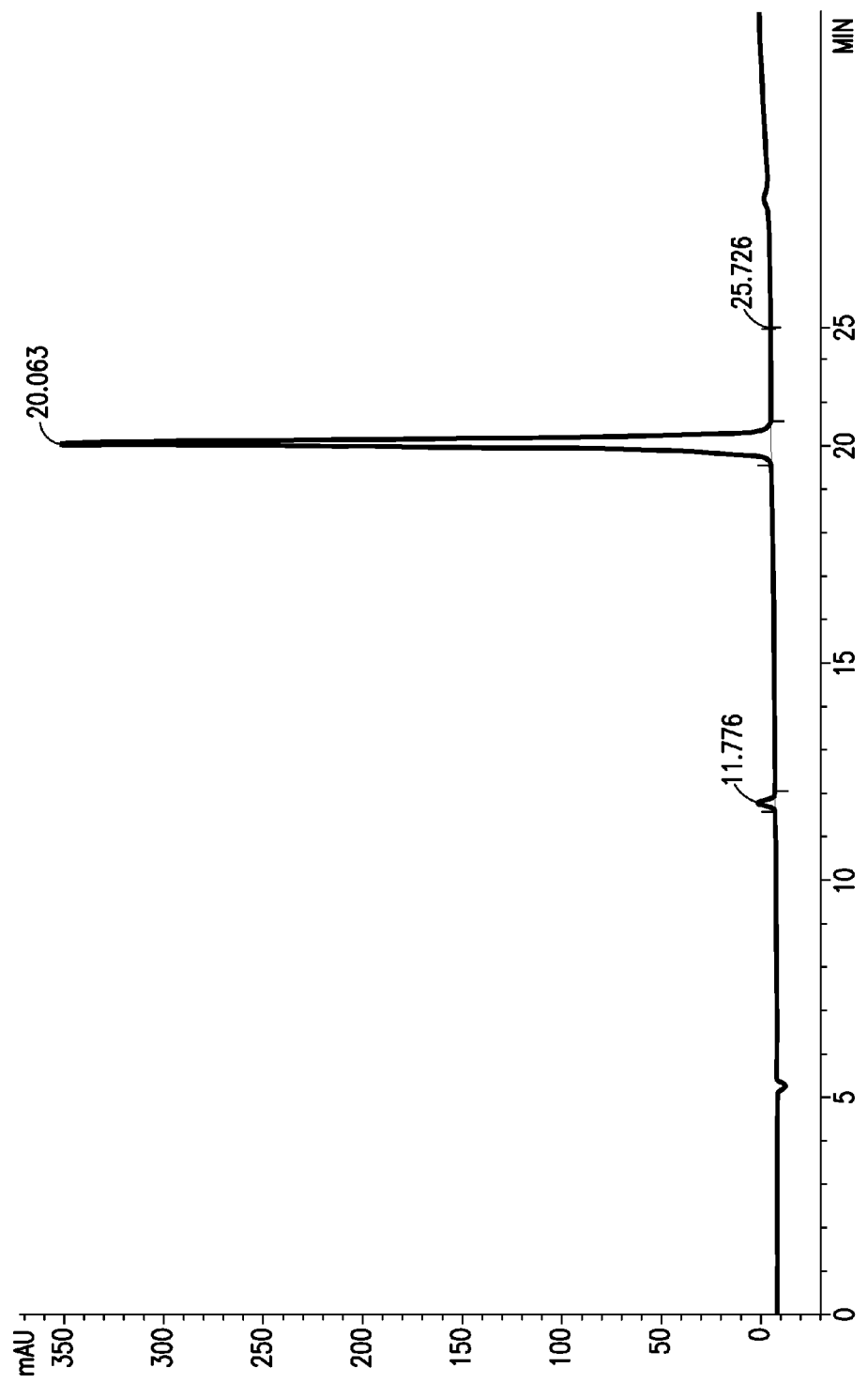
FIG. 22 shows the results of HPLC analysis conducted to examine the purity of Lobarstin.

Meanwhile, in order to increase the purity of the obtained compound, the compound was analyzed by reverse phase HPLC using Agilent Eclipse XDB-C18 column (4.6×150 mm, USA). The solvent system used in the analysis was composed of line A and line B which supplied 0.1% formic acid-containing water and 0.1% formic acid-containing acetonitrile, respectively. The elution conditions were as follows: 40% to 50% acetonitrile for 5 min; 50% to 80% acetonitrile for 15 min; and 80% to 90% acetonitrile for 10 min. The final purity was 96.1% (see FIG. 22).

Example 12

Structural Analysis of Novel Compound Lobarstin

Figure 23:
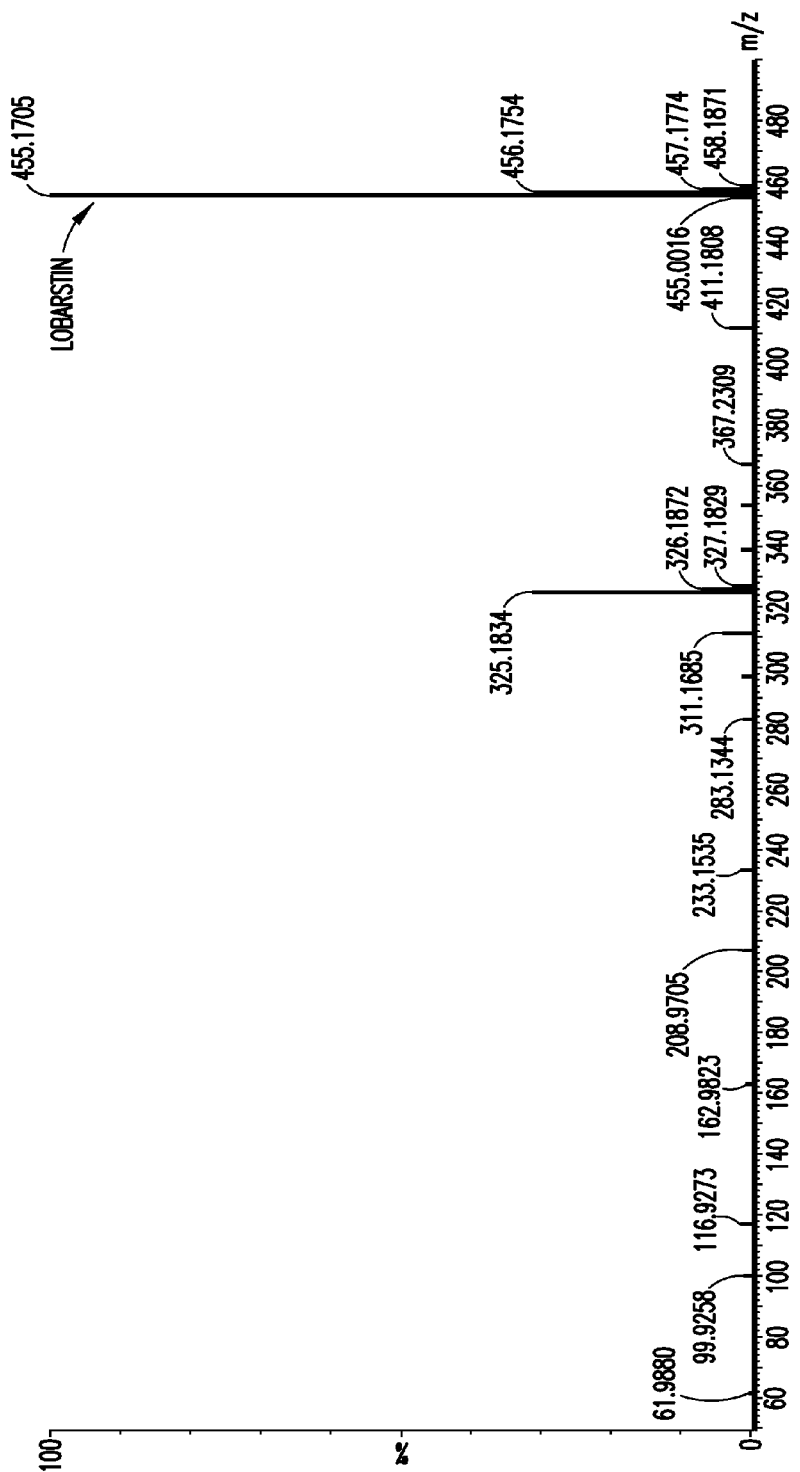
FIG. 23 shows the results of HRESIMS analysis of Lobarstin.

The molecular structure of Lobarstin synthesized in Example 11 was analyzed by high-resolution electrospray ionization mass spectrometry (HRESIMS) and NMR spectrometry. The analysis of anions by HRESIMS was carried out using Q-TOF micro LC-MS/MS instrument (Waters, USA). As can be seen in FIG. 23, Lobarstin showed a molecular ion peak of m/z 455.1708, suggesting that Lorbastin has a molecular formula of $C_{25}H_{28}O_8$.

The NMR spectra of Lobarstin were measured using JEOL ECP-400 spectrometer (JEOL, Japan) after dissolving Lobarstin in DMSO-$d_6$ solvent, and the chemical shift values (δC/δH=40.0/2.50 ppm) of the solvent DMSO-$d_6$ were used as reference points. For HMQC (1H-detected heteronuclear multiple-quantum coherence) analysis, 1JCH was set at 140 Hz, and for HMBC (heteronuclear multiple-bond coherence) analysis, nJCH was set at 8 Hz.

Figure 24A:
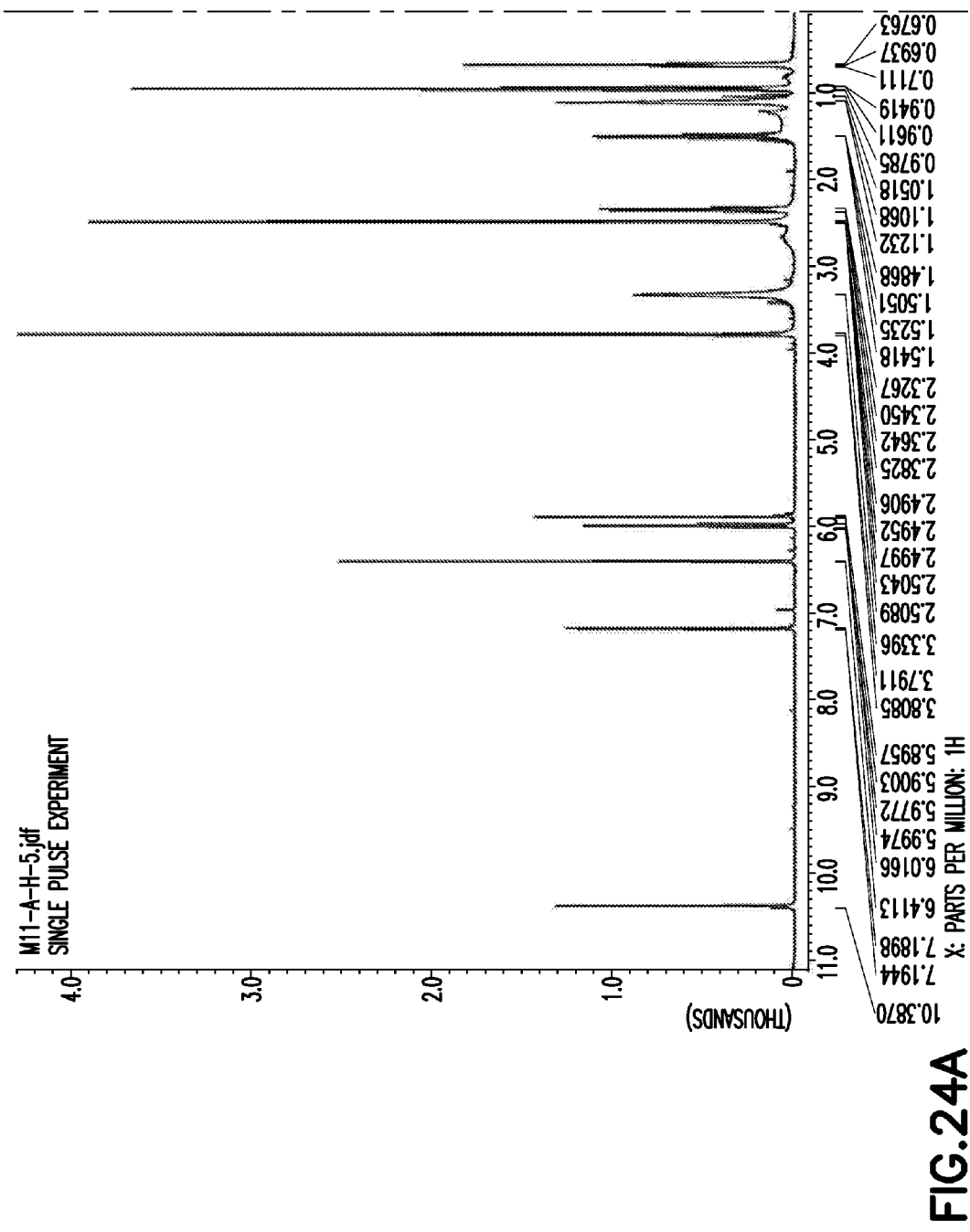
FIG. 24 shows for the $^1$H NMR spectrum (400 MHz, DMSO-$d_6$) of Lobarstin.
Figure 25A:
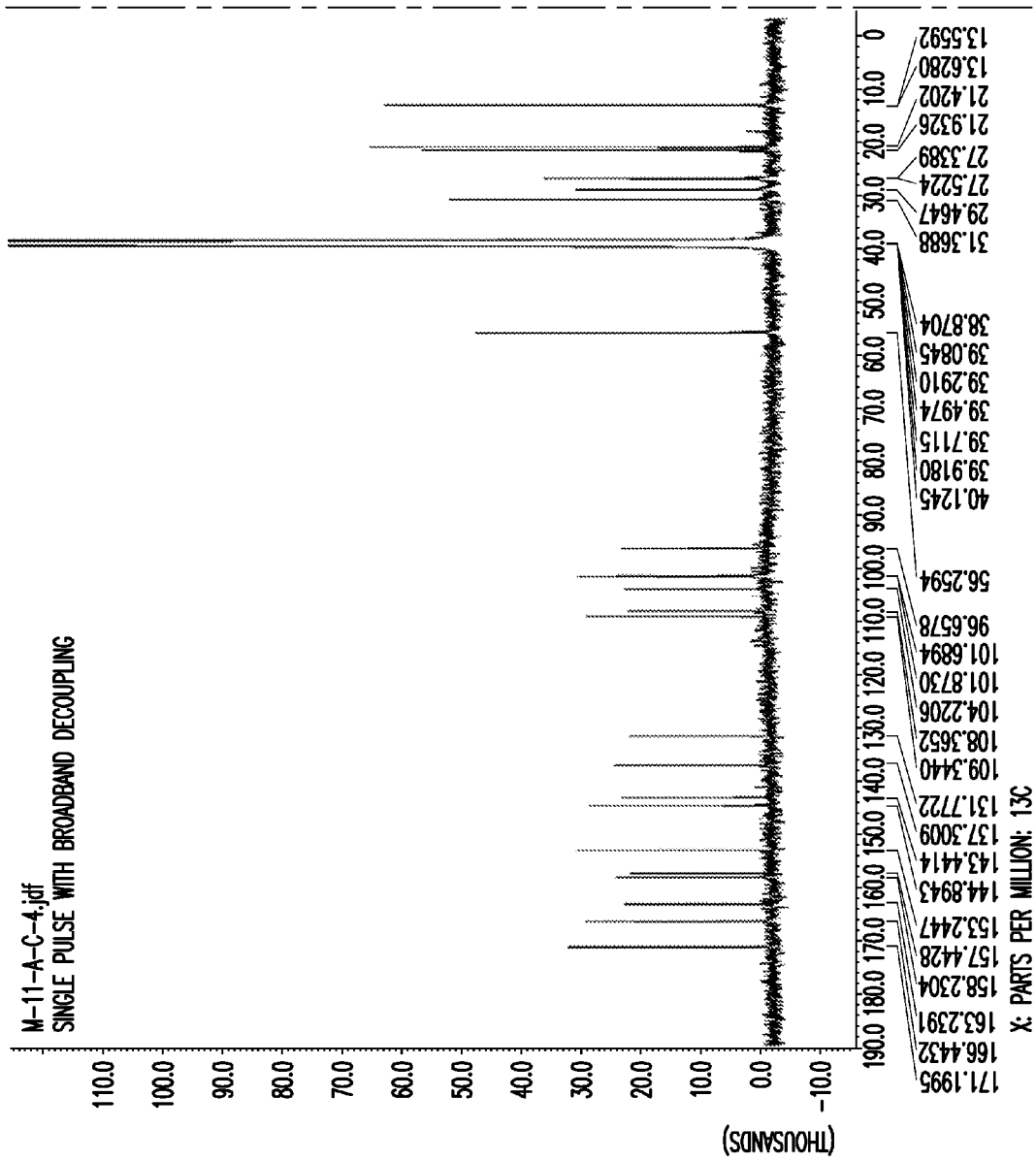
FIG. 25 shows the $^{13}$C NMR spectrum (400 MHz, DMSO-$d_6$) of Lobarstin.

As can be seen in the $^1$H NMR and $^{13}$C NMR spectra in FIGS. 24 and 25, respectively, the $^1$H NMR and $^{13}$C NMR spectra of Lobarstin showed patterns very similar to the NMR spectra of Lobarin of the following Formula 4.

[Formula 4]

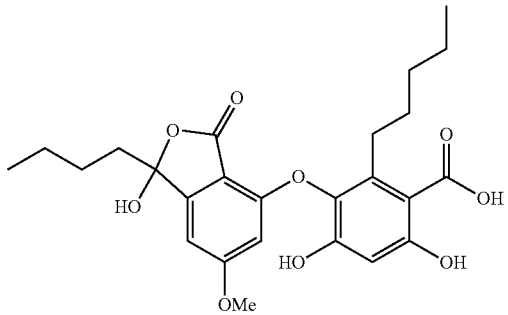

Chemical Formula: $C_{25}H_{30}O_9$
Molecular Weight: 474.5

Figure 26A:
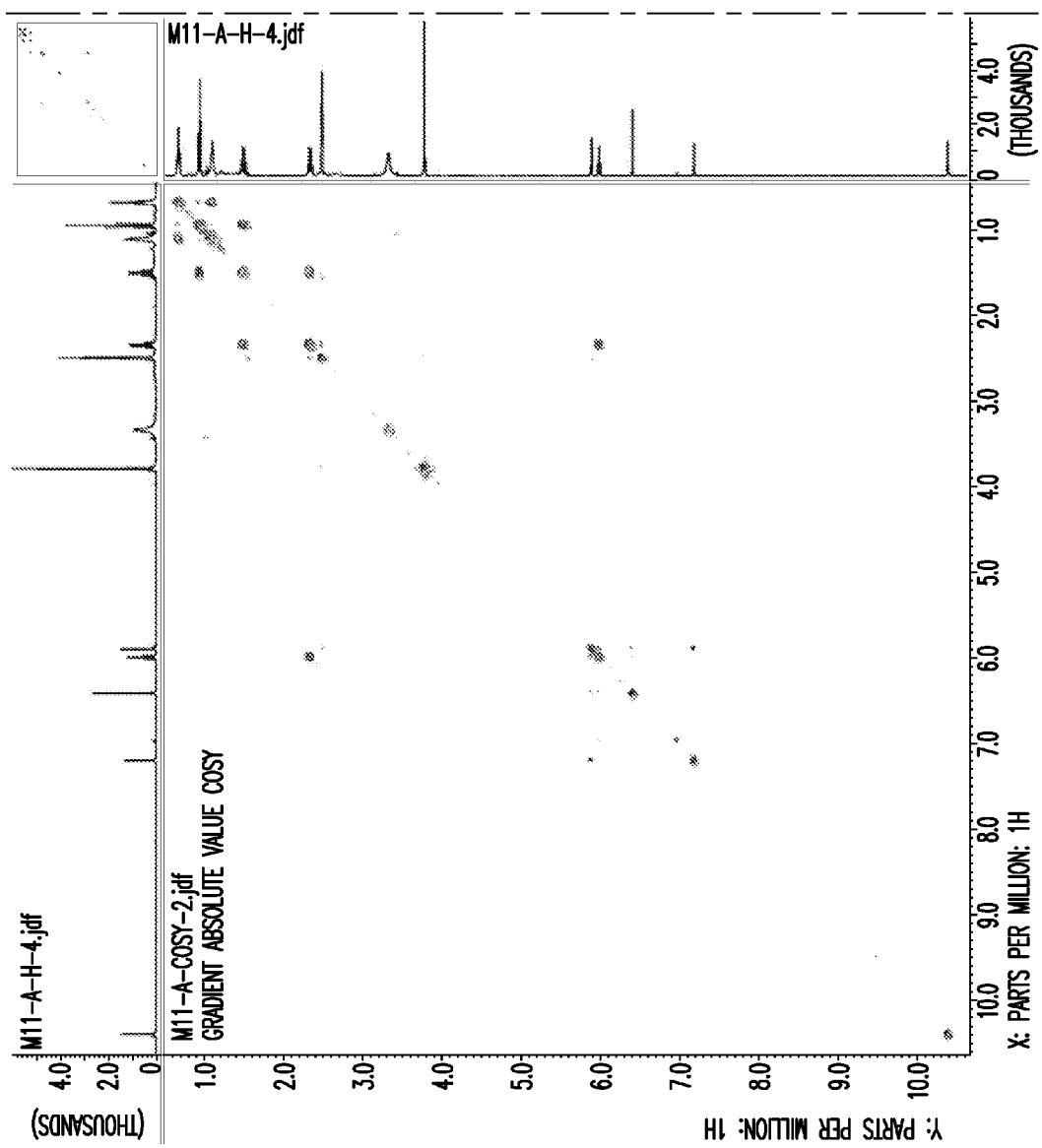
FIG. 26 shows COSY data (400 MHz, DMSO-$d_6$) for Lobarstin.
Figure 27A:
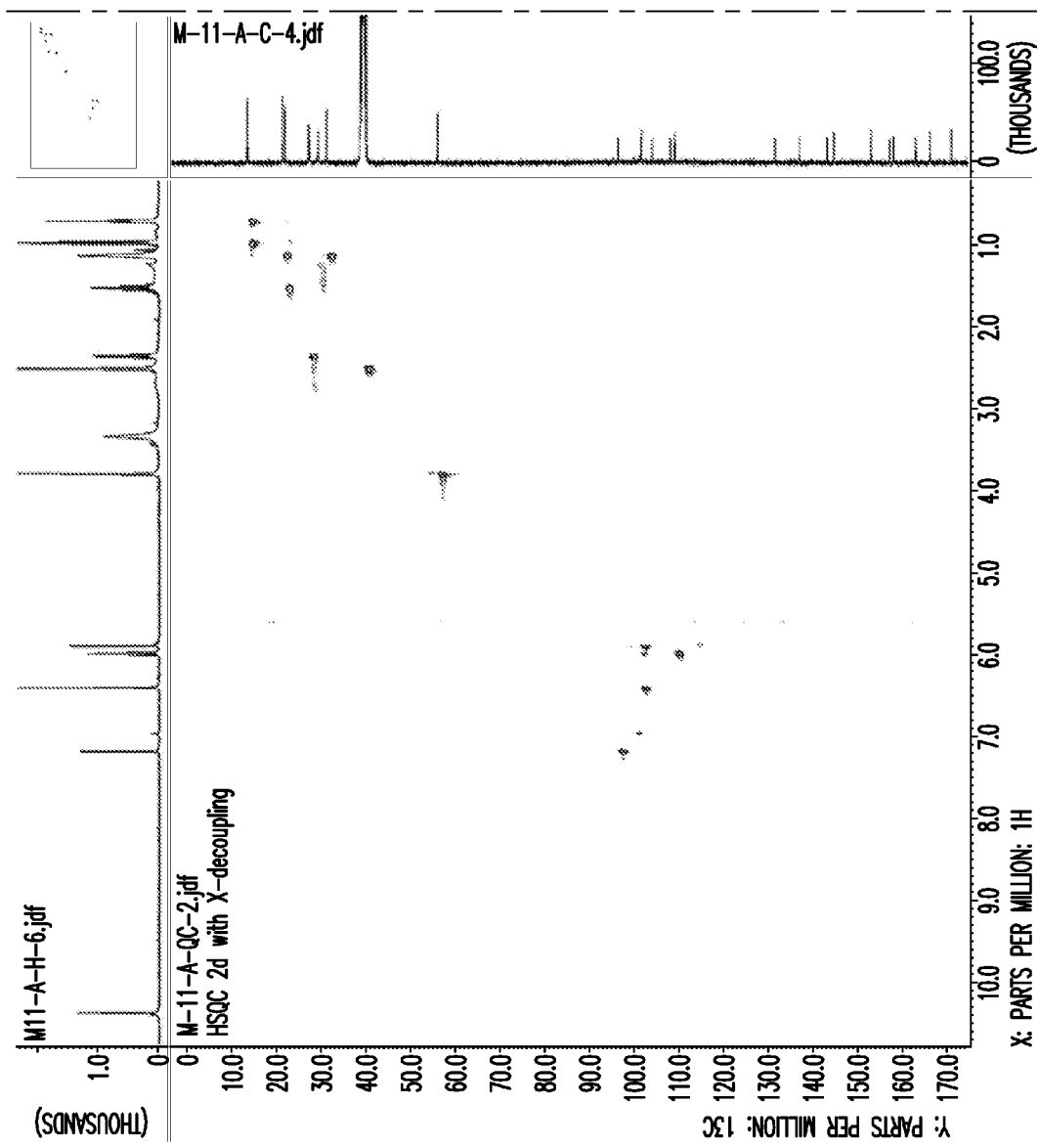
FIG. 27 shows HMQC data (400 MHz, DMSO-$d_6$) for Lobarstin.
Figure 28A:
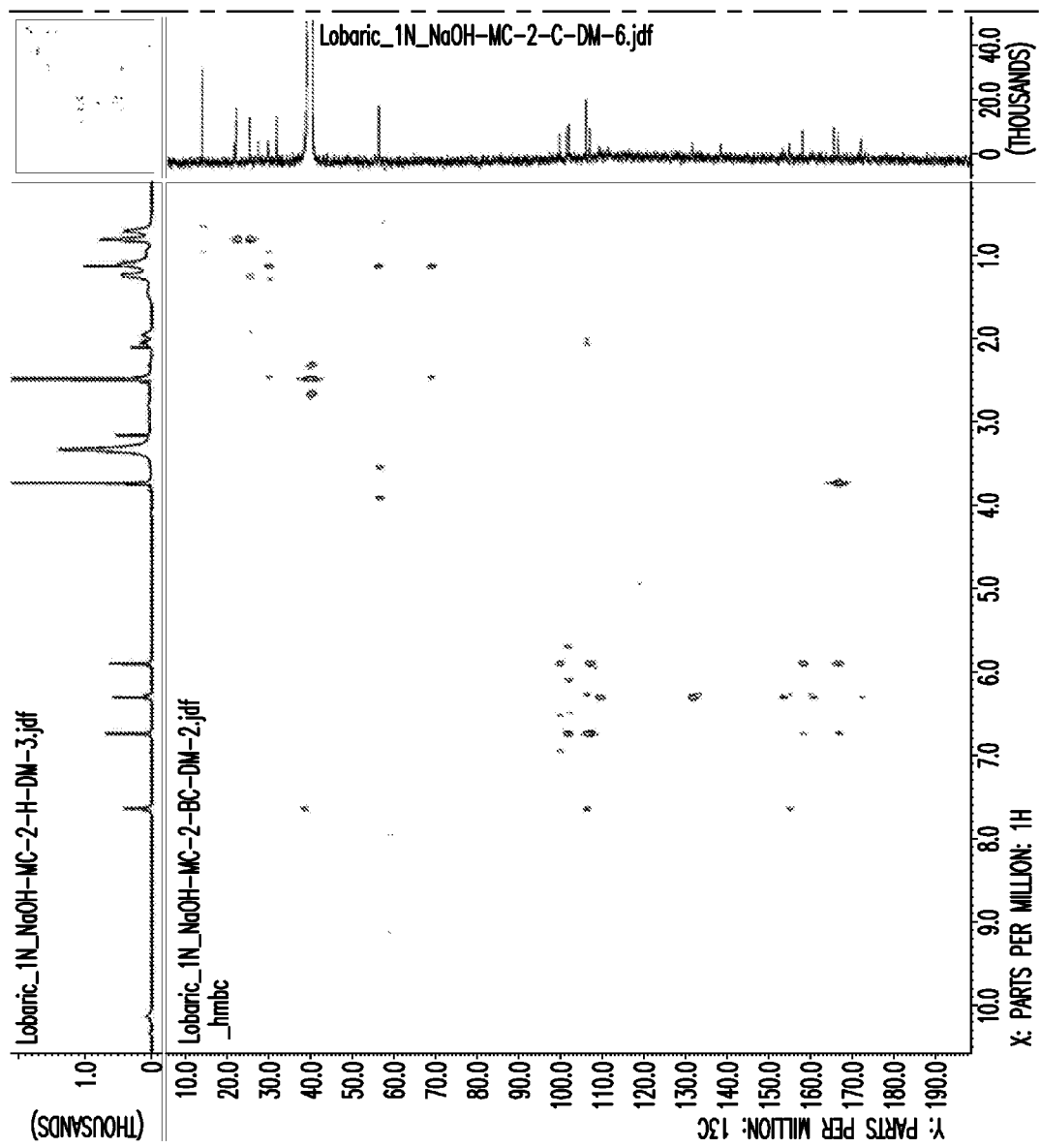
FIG. 28 shows HMBC data (400 MHz, DMSO-$d_6$) for Lobarstin.
Figure 29A:
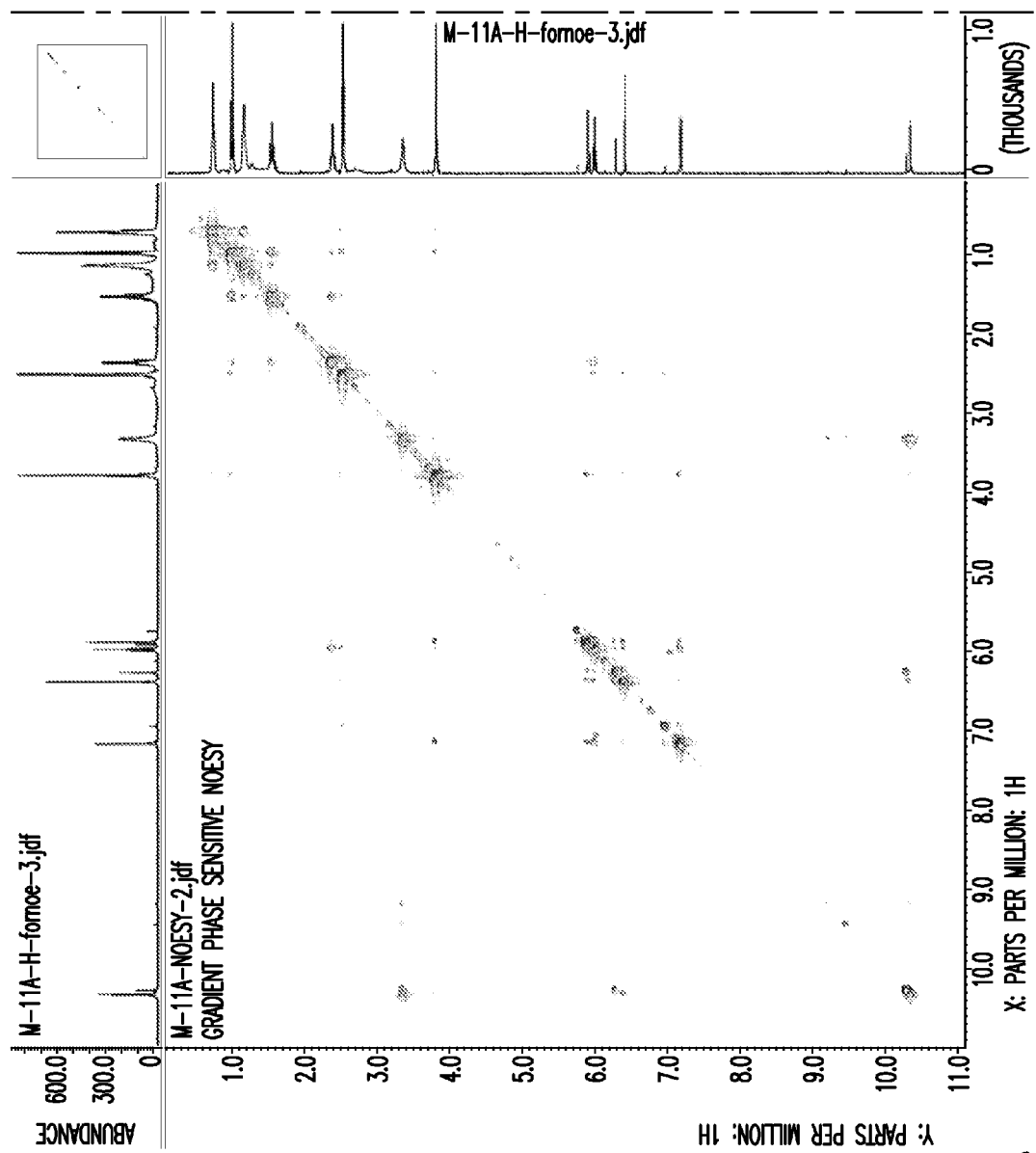
FIG. 29 shows NOESY data (400 MHz, DMSO-$d_6$) for Lobarstin.

Thus, Lobarstin can be supposed to be a compound produced by removal of a water molecule from Lobarin considering the fact that the structure of Lobarstin was very similar to that of Lobarin and the difference in molecular weight therebetween was 18 Da. When the NMR data of Lobarstin were compared with the NMR data of Lobarin, the absorption peak of the $sp^3$ hybridized carbon (C-8 of Lobarin, 106.3 ppm), which was shifted to the down-field region in the $^{13}$C NMR spectrum of Lobarstin, and the absorption peak of aliphatic methylene carbon, disappeared in the $^{13}$C NMR spectrum of Lobarin. Instead, an absorption peak was observed in two double bond regions of the $^{13}$C NMR spectrum of Lobarstin. In addition, it is observed that an absorption peak at the down-field shifted region of 6.00 ppm not present in the $^1$H NMR spectrum of Lobarin, appears in the $^{13}$C NMR spectrum of Lobarstin, and this peak is spin-spin coupled with an aliphatic methylene group as can be seen in the COSY data (see FIG. 26). Thus, it is believed that Lobarstin is a compound in which a double bond was formed at C-8 and C-9 while a tertiary-alcohol group was removed from Lobarin by dehydration. The predicted structure of Lobarstin was confirmed by HMQC analysis and HMBC analysis, which are two-dimensional NMR spectrometry methods (see Table 6). The positions corresponding to every carbon and hydrogen of Lobarstin were identified by analysis of the HMQC data (see FIG. 27) and the HMBC data (see FIG. 28). Particularly, HMBC correlations observed from H-5, 9, 10 and 11 in the structure of Lobarstin provided important information to identify the suggested structure of Lobarstin. In addition, the geometric structure of the double bond formed at C-8 and C-9 was a Z-form (cis-form), as determined based on the observation of NOE correlation between H-5 and H-9 (see FIG. 29).

TABLE 6

NMR data for Lobarstin (400 MHz, DMSO-$d_6$)

| Position | $\delta_C$ | $\delta_H$, mult.(J in Hz) | HMBC[a] |
|---|---|---|---|
| 1 | 104.2 | — | — |
| 2 | 157.4 | — | — |
| 3 | 101.7 | 5.90, d(1.8) | 1, 2, 4, 5, 7 |
| 4 | 166.4 | — | — |
| 5 | 96.7 | 7.19, d(1.8) | 1, 2, 3, 4, 8 |
| 6 | 143.4 | — | — |
| 7 | 163.2 | — | — |
| 8 | 144.9 | — | — |
| 9 | 109.3 | 6.00, t(7,7) | 6, 8 |
| 10 | 27.3 | 2.36, m | 8, 9, 11, 12 |
| 11 | 21.9 | 1.52, m | 9, 10, 12 |
| 12 | 3.63 | 0.96, t(7.0) | 10.11 |
| 1' | 108.4 | — | — |
| 2' | 158.2 | — | — |
| 3' | 101.9 | 6.41, s | 1', 2', 4', 5', 7' |
| 4' | 153.2 | — | — |
| 5' | 131.8 | — | — |
| 6' | 137.3 | — | — |
| 7' | 171.2 | — | — |
| 8' | 27.5 | 2,70, m/2.52, m | — |
| 9' | 29.5 | 1.39, m/1.27, m | — |
| 10' | 31.4 | 1.12, m | — |
| 11' | 21.4 | 1.12, m | — |
| 12' | 13.56 | 0.69, t(7.0) | 10', 11' |
| 4-OCH$_3$ | 56.3 | 3.79, s | 4 |
| 4'-OH | — | 10.39, s | 3', 4', 5' |

[a]HMBC correlations, optimized for 8 Hz, are from proton(s) stated to the indicated carbon(s).

Example 13

Analysis of PTP-1b Inhibitory Activity of Lobarstin

The activity of the enzyme was spectroscopically measured to analyze the protein PTP-1b inhibitory activity of Lobarstin. Specifically, to 0.5 mg/Ml of PTP-1b (Bioneer, Korea) in PTP-1b buffer (20 mM Tris-HCL, pH 8.0, 0.75 mM NaCl, 0.5 mM EDTA, 5 mM β-mercaptoethanol, 50% glycerol), 0, 1, 3, 10, 30, 100, 300, 1000 or 3000 nM Lobarstin and the substrate [pTyr1146] insulin receptor (1142-1153, Sigma, USA) were added. Each of the mixtures was allowed to react at room temperature for 10-30 minutes, and malachite green-molybdate dye solution (1142-1153, Sigma, USA) was added thereto and reacted at room temperature for 10 minutes. After completion between PTP-1b, Lobarstin and the substrate, the absorbance at 620 nm was measured.

Figure 30:
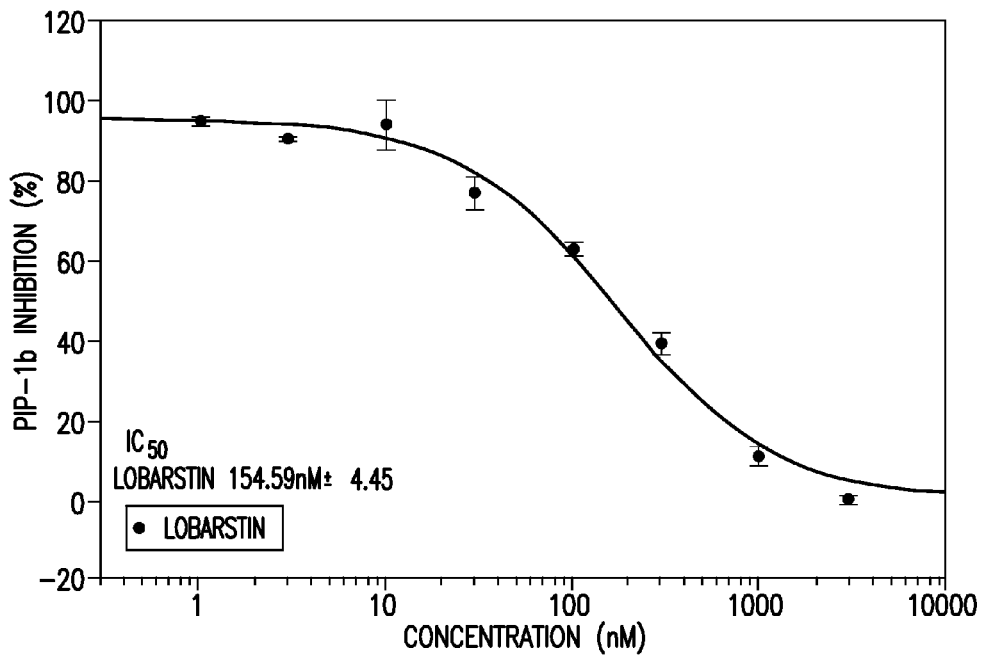
FIG. 30 is a graph showing the PTP-1b inhibitory activity of Lobarstin.

The inhibitory activity of Lobarstin against PTP-1b was analyzed as described above. As a result, Lobarstin showed an IC$_{50}$ of 154.6 nM as can be seen in FIG. 30, suggesting that it has excellent PTP-1b inhibitory effect. In addition, the inhibition (%) of PTP-1b increased as increasing the concentration of Lobarstin. Thus, it was confirmed that Lobarstin is a pharmaceutical compound capable of preventing or treating diabetes and obesity.

Example 14

Analysis of Selectivity of Lobarstin for Protein Tyrosine Phosphatases

In order to examine the selectivity of Lobarstin for protein tyrosine phosphatases, the inhibitory activities of Lobarstin against PTP-1b, PTPN2, PTPN5, PTPN6, PTPN7 and PTPN13 were examined by spectroscopically measuring the activities of the enzymes. Specifically, to 0.5 mg/Ml of PTP-1b, PTPN2, PTPN5, PTPN6, PTPN7 or PTPN13 (Bioneer, Korea) in protein tyrosine phosphatase buffer (20 mM Tris-Hcl, pH 8.0, 0.75 mM NaCl, 0.5 mM EDTA, 5 mM β-mercaptoethanol, 50% glycerol), 0, 50, 100 or 200 nM Lobarstin and the substrate [pTyr1146] insulin receptor (1142-1153, Sigma, USA) were added. Then, each of the mixtures was allowed to react at room temperature for 10-30 minutes, and then malachite green-molybdate dye solution (Sigma, USA) was added thereto and reacted at room temperature for 10 minutes. After completion of the reaction with the substrate, the absorbance at 620 nm was measured.

Figure 31:
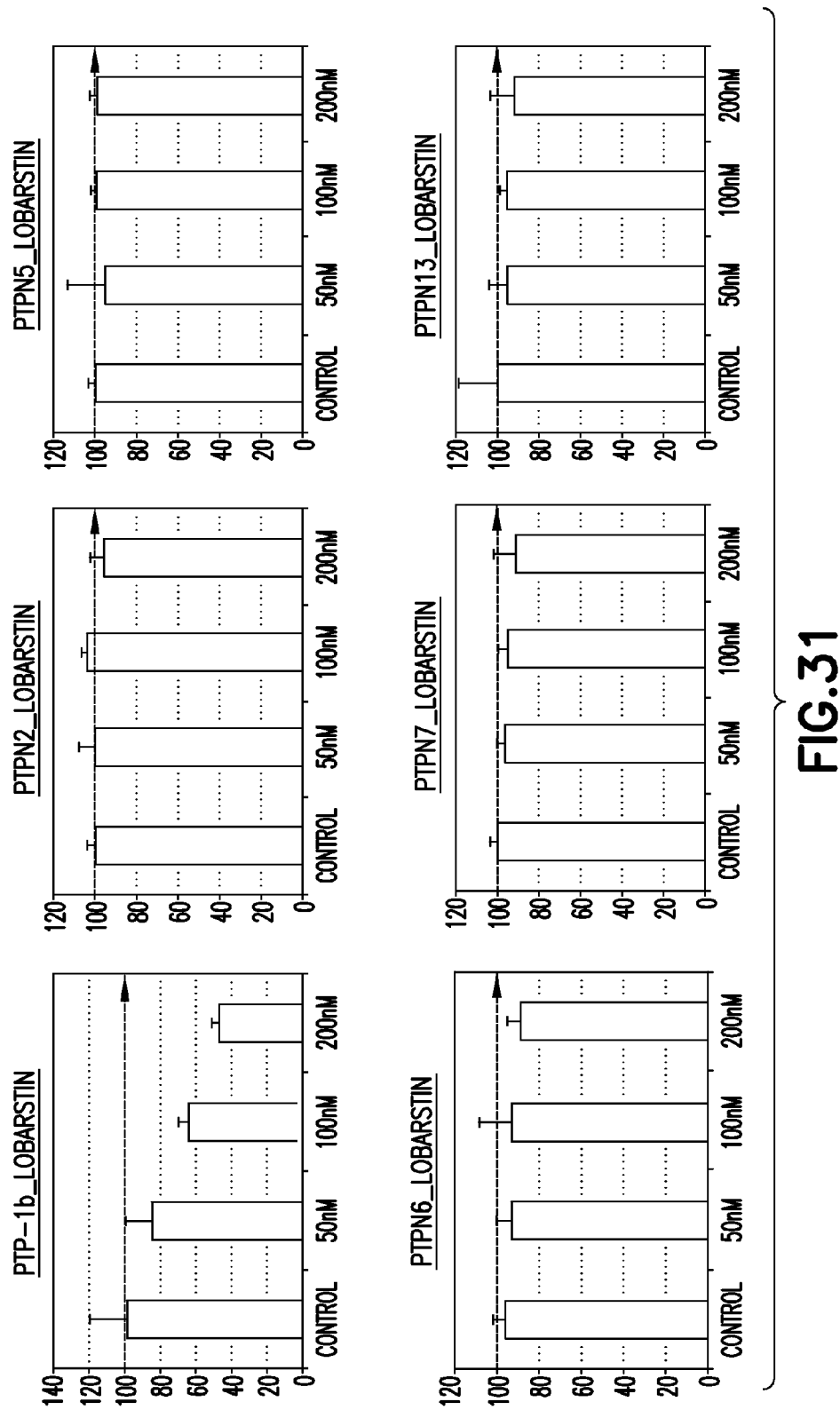
FIG. 31 is a set of graphs showing the inhibitory activities of Lobarstin against PTP-1b, PTPN2, PTPN5, PTPN6, PTPN7 and PTPN13, determined by measuring absorbance at 620 nm.

The selectivity of sodium borate for protein tyrosine phosphatases was examined as described above. As a result, Lobarstin showed an inhibition rate of 47.96% against PTP-1b at a concentration of 200 uM (IC$_{50}$), and particularly, Lobarstin had no inhibitory activity against other protein tyrosine phosphatases, including TC-PTP (PTPN2), as can be seen in FIG. 31.

Accordingly, the above test results indicate that the compound Lobarstin according to the present invention acts selectively only on PTP-1b among protein tyrosine phosphatases and that Lobarstin is a PTP-1b inhibitor which can be used to treat diabetes.

Example 15

Verification of Effects of Lobastin on Disease Model Animals 15-1: Observation of Change in Blood Glucose Level after Intraperitoneal Administration of Lobarstin Based on pre-tests, effectiveness tests and toxicity tests for Lobarstin, dose (expressed as test compound amount (mg)/test animal's weight (kg)) was determined. To 7-week-old male db/db mice (type 2 diabetic model animals, C57/BLKS/J-db/db, the Korea Research Institute of Bioscience and Biotechnology), 200 µl of PBS for a control group and 10 mg/kg of Lobarstin for a test group was administered, respectively, intraperitoneally daily, and the blood glucose levels of the animals were measured twice a week.

Figure 32:
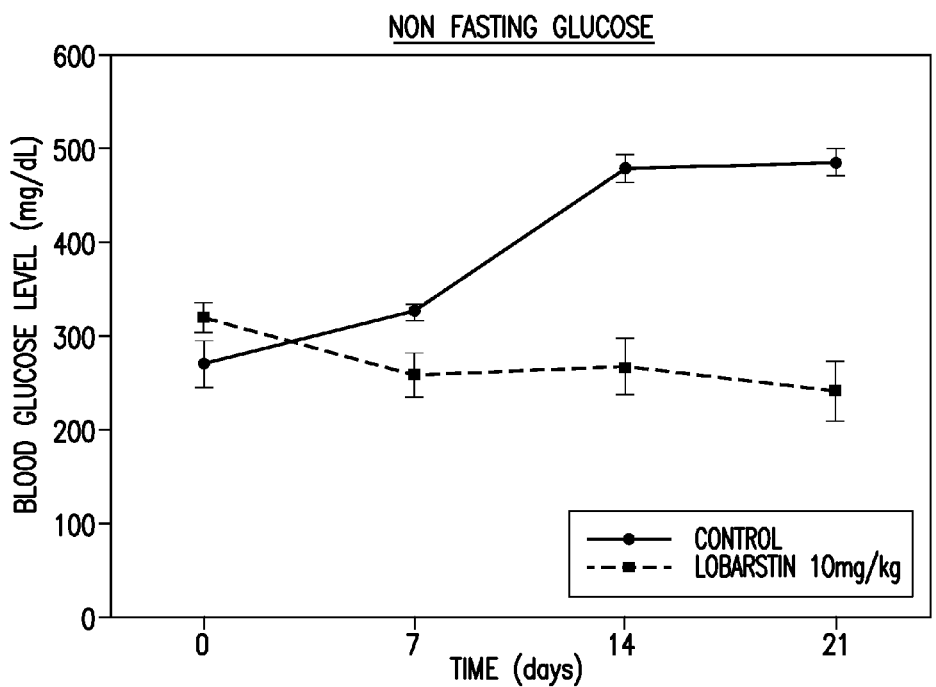
FIG. 32 is a graphic diagram showing the results of measuring the change in the blood glucose levels after intraperitoneal administration of Lobarstin.

Specifically, Lobarstin was administered by intraperitoneal injection to 7-week-old male db/db mice (type 2 diabetic model animals, C57/BLKS/J-db/db, the Korea Research Institute of Bioscience and Biotechnology), and the change in blood glucose level of the animals was measured. As a result, it was found that the average blood glucose level was 271 mg/dL at day 0, 326 mg/dL at day 7, 479 mg/dL at day 14, and 486 mg/dL at day 21 in the control group (n=6), indicating that the blood glucose level increased rapidly, and that, however, the average blood glucose level was 299 mg/dL at day 0, 259 mg/dL at day 7, 267 mg/dL at day 14, and 242 mg/dL at day 21 in the test group (n=6) injected intraperitoneally with 10 mg/kg of Lobarstin, and the increase in the blood glucose level was less than that in the control group as can be seen in FIG. 32.

15-2: Observation of Change in Blood Glucose Level Following 6 Hours of Fasting after Intraperitoneal Administration of Lobarstin In order to more accurately measure the anti-diabetic effect of Lobarstin, 200 µl of PBS for a control group and 10 mg/kg of Lobarstin for a test group was administered intraperitoneally daily to 7-week-old male db/db mice (type 2 diabetic model animals, C57/BLKS/J-db/db, the Korea Research Institute of Bioscience and Biotechnology), and the blood glucose levels of the animals were measured twice a week. Herein, measurement of the blood glucose levels was performed after 6 hours of fasting after intraperitoneal injection of Lobarstin.

Figure 33:
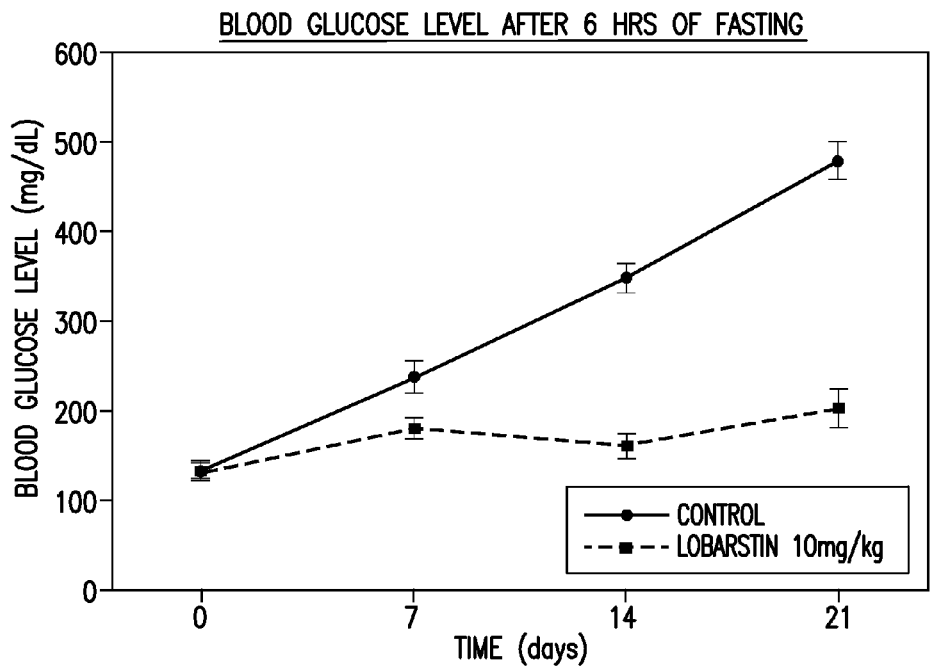
FIG. 33 is a graphic diagram showing the results of measuring the blood glucose level following 6 hours of fasting after intraperitoneal administration of Lobarstin.

As a result, as can be seen in FIG. 33, it was found that the average blood glucose level was 134 mg/dL at day 0, 238 mg/dL at day 7, 350 mg/dL at day 14, and 479 mg/dL at day 21 in the control group (n=6), indicating that the blood glucose level increased rapidly, and that, however, the average blood glucose level was 134 mg/dL at day 0, 182 mg/dL at day 7, 162 mg/dL at day 14, and 204 mg/dL at day 21 in the test group (n=6) injected intraperitoneally with 10 mg/kg of Lobarstin, and the increase in the blood glucose level was less than that in the control group, as Example 15-1.

15-3: Intraperitoneal Glucose Tolerance Test 28 Days after Intraperitoneal Administration of Lobarstin An intraperitoneal glucose tolerance test (IPGTT) in the animal model of Lobarin was performed in the following manner.

To 7-week-old male db/db mice (type 2 diabetic model animals, C57/BLKS/J-db/db, the Korea Research Institute of Bioscience and Biotechnology), 20% DMSO for a control group and 10 mg/kg of Lobarstin for a test group was injected, respectively, intraperitoneally every day for 28 days. Then, the animals were fasted for 16 hours without administering physiological saline and Lobarstin, after which glucose (500 mg/Ml; injection volume of 200 µl) was injected intraperitoneally into the animals. 0, 15, 30, 60, 90 and 120 min after injection of glucose, blood was sampled from the tail vein, and the changes in the blood glucose levels of the samples were measured.

Figure 34:
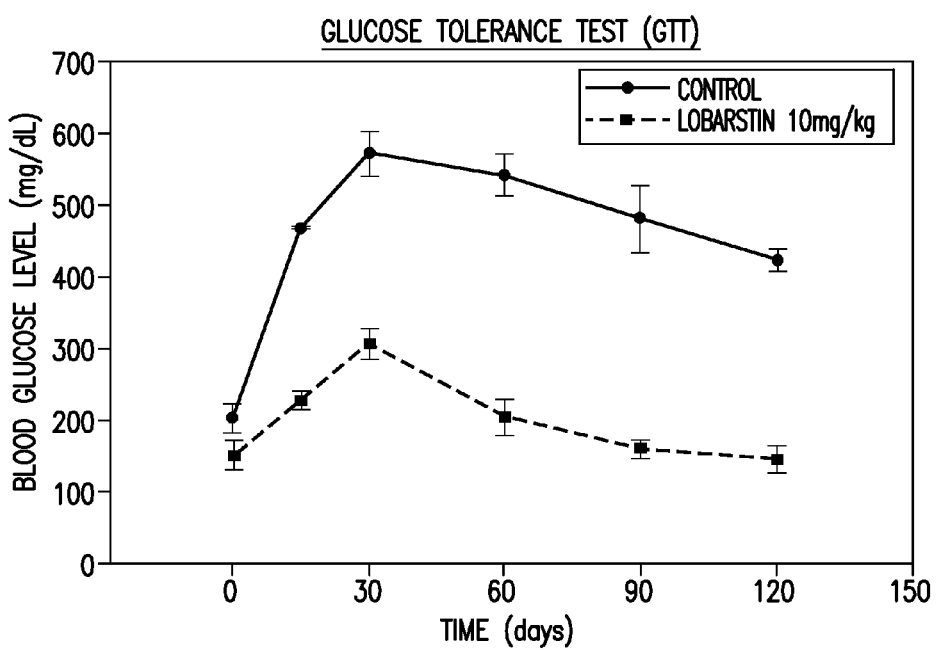
FIG. 34 is a graphic diagram showing the results of a glucose tolerance test carried out 28 days after intraperitoneal administration of Lobarstin.

As described above, the changes in glucose tolerance resulting from intraperitoneal injection of glucose into the type 2 diabetic model animals were measured. As a result, as can be seen in FIG. 34, in the control group (injected intraperitoneally with 20% DMSO), the blood glucose level after injection of glucose was 204 mg/dL at 0 min, 496 mg/dL at 15 min, 572 mg/dL at 30 min, 542 mg/dL at 60 min, 483 mg/dL at 90 min, and 424 mg/dL at 120 min, and the increase in the blood glucose levels was very rapid and the decrease in the blood glucose levels was very slow. On the other hand, in the test group administered intraperitoneally with 10 mg/kg of Lobarstin, the blood glucose level after injection of glucose was 152 mg/dL at 0 min, 229 mg/dL at 15 min, 307 mg/dL at 30 min, 205 mg/dL at 60 min, 162 mg/dL at 90 min, and 147 mg/dL at 120 min, and thus a low increase and a fast decrease in the blood glucose level were observed, suggesting that the blood glucose level was normalized (see FIG. 34). The results of Examples 15-1 to 15-3 indicate that the novel compound Lobarstin according to the present invention has a very excellent anti-diabetic effect.

INDUSTRIAL APPLICABILITY

As described above, the novel compounds of the invention have very excellent PTP-1b (protein tyrosine phosphatase-1b) inhibitory activities, act selectively only on PTP-1b among protein tyrosine phosphatases, and are substantial PTP-1b inhibitors which are effective in preventing or treating diabetes or obesity.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A compound represented by the following Formula 5:

[Formula 5]

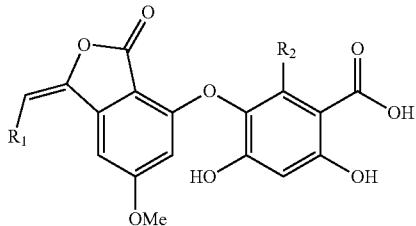

wherein $R_1$ and $R_2$ are independently selected from the group consisting of H, an alkyl group, an aryl group, an allyl group, an arylalkyl group, and an acyl group.

2. The compound of claim 1, wherein the compound is represented by the following Formula 6:

[Formula 6]

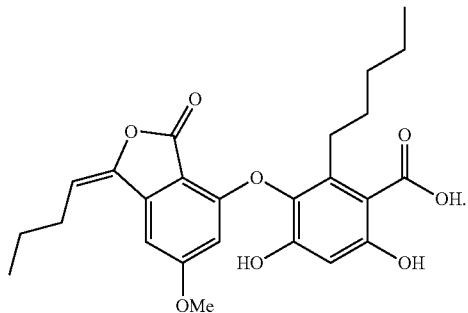

Chemical Formula: $C_{25}H_{28}O_8$
Molecular Weight: 456.49

3. A method for preparing a compound represented by the following Formula 6, the method comprising the steps of:
   (a) extracting *Stereocaulon alpinum* with methanol;
   (b) eluting the *Stereocaulon alpinum* extract, obtained in step (a), with an aqueous solution of methanol or acetonitrile ($CH_3CN$) by column chromatography;
   (c) eluting a fraction, eluted in step (b), with an aqueous solution of acetonitrile ($CH_3CN$) or methanol by reverse-phase high-performance liquid chromatography to obtain a lobaric acid-containing fraction; and
   (d) dissolving the lobaric acid-containing fraction in a solvent, adding water and a base added thereto, stirring the mixture to react, adding an acidic solution to the reaction mixture to stop the reaction, and then collecting the compound of the following Formula 6 from the reaction solution:

[Formula 6]

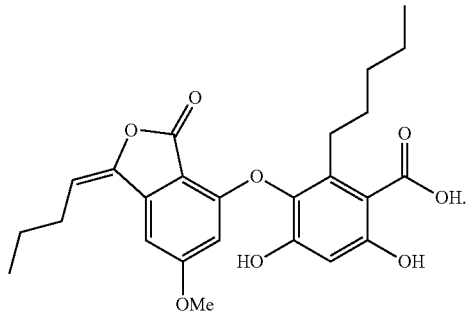

Chemical Formula: $C_{25}H_{28}O_8$
Molecular Weight: 456.49

4. The method of claim 3, wherein in step (d), the solvent is acetone, the base is NaOH or KOH, and the acidic solution is a HCl solution, a $H_2SO_4$ solution or a $HNO_3$ solution.

5. The method of claim 3, wherein in step (d), the compound of the following Formula 6 is collected by concentrating the acidic solution-containing mixture, partitioning the concentrate between methylene chloride, chloroform or ethylene chloride and an aqueous solution to obtain a methylene chloride, chloroform or ethylene chloride layer, and concentrating the obtained layer:

[Formula 6]

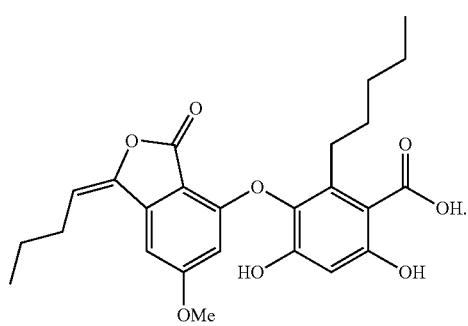

Chemical Formula: $C_{25}H_{28}O_8$
Molecular Weight: 456.49

6. A method for preventing or treating diabetes or obesity in a subject, the method comprising administering to the subject a pharmaceutical composition comprising, as an active ingredient, a compound represented by the following Formula 5 or a pharmaceutically acceptable salt thereof:

[Formula 5]

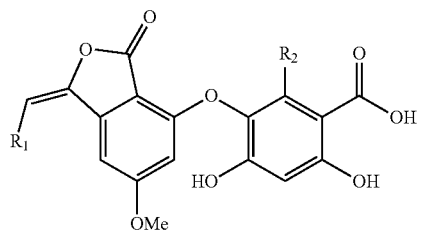

wherein $R_1$ and $R_2$ are independently selected from the group consisting of H, an alkyl group, an aryl group, an allyl group, an arylalkyl group, and an acyl group.

7. The method of claim 6, wherein the compound is represented by the following Formula 6:

[Formula 6]

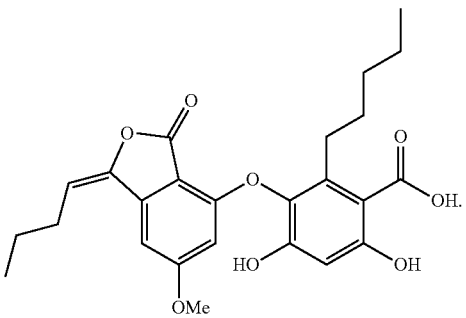

Chemical Formula: $C_{25}H_{28}O_8$
Molecular Weight: 456.49

8. A method for preventing or alleviating diabetes or obesity in a subject, the method comprising feeding the subject with a functional food comprising, as an active ingredient, a compound represented by the following Formula 5:

[Formula 5]

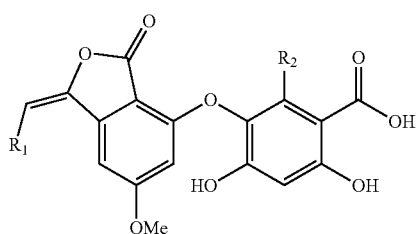

wherein $R_1$ and $R_2$ are independently selected from the group consisting of H, an alkyl group, an aryl group, an allyl group, an arylalkyl group, and an acyl group.

9. The method of claim 8 wherein the compound is represented by the following Formula 6:

[Formula 6]

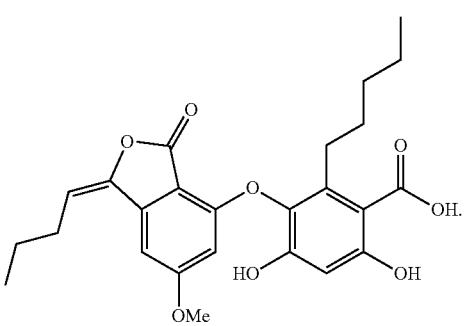

Chemical Formula: $C_{25}H_{28}O_8$
Molecular Weight: 456.49

* * * * *